(12) United States Patent
Bethiel et al.

(10) Patent No.: US 6,949,544 B2
(45) Date of Patent: Sep. 27, 2005

(54) INHIBITORS OF C-JUN N-TERMINAL KINASES (JNK) AND OTHER PROTEIN KINASES

(75) Inventors: Randy S. Bethiel, Arlington, MA (US); John Cochran, North Andover, CA (US); Young-Choon Moon, Lexington, MA (US); Suganthini Nanthakumar, Newton, MA (US)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 53 days.

(21) Appl. No.: 10/109,070

(22) Filed: Mar. 28, 2002

(65) Prior Publication Data

US 2003/0087922 A1 May 8, 2003

Related U.S. Application Data

(60) Provisional application No. 60/279,961, filed on Mar. 29, 2001.

(51) Int. Cl.$^7$ .................. A61K 31/505; C07D 239/42
(52) U.S. Cl. .................. 514/235.8; 514/245; 514/269; 514/274; 514/275; 544/122; 544/212; 544/296; 544/330; 544/331; 544/332
(58) Field of Search ............... 544/122, 212, 544/296, 330, 331, 332, 321, 209; 514/235.8, 245, 269, 274, 275, 272

(56) References Cited

FOREIGN PATENT DOCUMENTS

| WO | WO 95/09847 | 4/1995 |
|---|---|---|
| WO | WO 97/19065 | 5/1997 |
| WO | WO 01/29009 | 4/2001 |
| WO | WO 02/20495 | 3/2002 |
| WO | WO 02/46170 | 6/2002 |
| WO | WO 02/46171 | 6/2002 |

OTHER PUBLICATIONS

CAS printout for Kois et al., Chem Abstract 137:449662 (WO 02/46171).*
CAS printout for Davis et al., Chem Abstract 127:81461 (WO 97/19065).*
CAs printout for Zimmermann et al., Chem Abstract 123:313996 (WO 95/09847).*
* cited by examiner Primary Examiner—Richard L. Raymond
(74) Attorney, Agent, or Firm—Vertex Pharmaceuticals Incorporated; Karen E. Brown

(57) ABSTRACT

The present invention provide a compound of formula I or II:

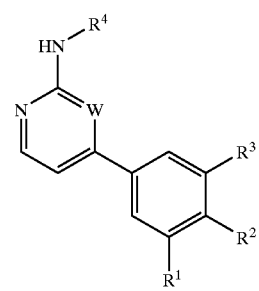

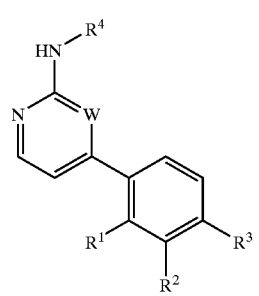

or a pharmaceutically acceptable derivative thereof, wherein $R^1$, $R^2$, $R^3$, and $R^4$ are as described in the specification. These compounds are inhibitors of protein kinase, particularly inhibitors of JNK, a mammalian protein kinase involved cell proliferation, cell death and response to extracellular stimuli; and Src-family kinases, especially Src and Lck kinases. These compounds are also inhibitors of GSK3 and CDK2 kinases. The invention also relates to methods for producing these inhibitors. The invention also provides pharmaceutical compositions comprising the inhibitors of the invention and methods of utilizing those compositions in the treatment and prevention of various disorders.

25 Claims, No Drawings

SEQUENCE LISTING

<160> NUMBER OF SEQ ID NOS: 2

<210> SEQ ID NO 1
<211> LENGTH: 39
<212> TYPE: DNA

-continued

```
<213> ORGANISM: Unknown Organism
<220> FEATURE:
<223> OTHER INFORMATION: Description of Unknown Organism:
      deoxyoligonucleotides

<400> SEQUENCE: 1
gctctagagc tccatgggca gcaaaagcaa agttgacaa                              39

<210> SEQ ID NO 2
<211> LENGTH: 37
<212> TYPE: DNA
<213> ORGANISM: Unknown Organism
<220> FEATURE:
<223> OTHER INFORMATION: Description of Unknown Organism:
      deoxyoligonucleotides

<400> SEQUENCE: 2
tagcggatcc tcattctgaa ttcattactt ccttgta                                37
```

INHIBITORS OF C-JUN N-TERMINAL KINASES (JNK) AND OTHER PROTEIN KINASES

CROSS REFERENCE TO RELATED APPLICATION

This application claims priority to U.S. Provisional Patent Application No. 60/279,961 filed Mar. 29, 2001, the contents of which is incorporated herein by reference.

TECHNICAL FIELD OF INVENTION

The present invention relates to inhibitors of protein kinase, especially c-Jun N-terminal kinases (JNK) and Src-family of kinases, which are members of the mitogen-activated protein (MAP) kinase family. There are a number of different genes and isoforms which encode JNKs. Members of the JNK family regulate signal transduction in response to environmental stress and proinflammatory cytokines and have been implicated in the mediation of a number of different disorders. Members of the Src family are implicated in a number of human diseases. The invention also relates to inhibitors of GSK3 kinase, which is implicated in diabetes and other disorders, and CDK2 kinase which plays a role in the regulation of the cell division cycle. The invention also provides pharmaceutical compositions comprising the inhibitors of the invention and methods of utilizing those compositions in the treatment and prevention of various disorders.

BACKGROUND OF THE INVENTION

Mammalian cells respond to extracellular stimuli by activating signaling cascades that are mediated by members of the mitogen-activated protein (MAP) kinase family, which include the extracellular signal regulated kinases (ERKs), the p38 MAP kinases and the c-Jun N-terminal kinases (JNKs). MAP kinases (MAPKs) are activated by a variety of signals including growth factors, cytokines, UV radiation, and stress-inducing agents. MAPKs are serine/threonine kinases and their activation occurs by dual phosphorylation of threonine and tyrosine at the Thr-X-Tyr segment in the activation loop. MAPKs phosphorylate various substrates including transcription factors, which in turn regulate the expression of specific sets of genes and thus mediate a specific response to the stimulus.

In the c-Jun $NH_2$-terminal protein kinases, also known as JNKs, three distinct genes, JNK1, JNK2, JNK3 have been identified and at least ten different splicing isoforms of JNKs exist in mammalian cells [Gupta et al., *EMBO J.*, 15:2760–70 (1996)]. Members of the JNK family are activated by proinflammatory cytokines, such as tumor necrosis factor-α (TNFα) and interleukin-1 β (IL-1β), as well as by environmental stress, including anisomycin, UV irradiation, hypoxia, and osmotic shock [Minden et al., *Biochemica et Biophysica Acta*, 1333:F85–F104 (1997)].

The down-stream substrates of JNKs include transcription factors c-Jun, ATF-2, Elk1, p53 and a cell death domain protein (DENN) [Zhang et al. *Proc. Natl. Acad. Sci. USA*, 95:2586–91 (1998)]. Each JNK isoform binds to these substrates with different affinities, suggesting a regulation of signaling pathways by substrate specificity of different JNKs in vivo (Gupta et al., supra).

JNKs, along with other MAPKs, have been implicated in the mediation of cellular response to cancer, thrombin-induced platelet aggregation, immunodeficiency disorders, autoimmune diseases, cell death, allergies, osteoporosis and heart disease. The therapeutic conditions related to activation of the JNK pathway include chronic myelogenous leukemia (CML), rheumatoid arthritis, asthma, osteoarthritis, ischemia, cancer and neurodegenerative diseases.

Several reports have detailed the importance of JNK activation associated with liver disease or episodes of hepatic ischemia [*Nat. Genet.* 21:326–9 (1999); *FEBS Lett.* 420:201–4 (1997); *J. Clin. Invest.* 102:1942–50 (1998); *Hepatology* 28:1022–30 (1998)].

A role for JNK in cardiovascular disease such as myocardial infarction or congestive heart failure has also been reported as it has been shown JNK mediates hypertrophic responses to various forms of cardiac stress [*Circ. Res.* 83:167–78 (1998); *Circulation* 97:1731–7 (1998); *J. Biol. Chem.* 272:28050–6 (1997); *Circ. Res.* 79:162–73 (1996); *Circ. Res.* 78:947–53 (1996); *J. Clin. Invest.* 97:508–14 (1996)].

It has been demonstrated that the JNK cascade also plays a role in T-cell activation, including activation of the IL-2 promoter. Thus, inhibitors of JNK have potential therapeutic value in altering pathologic immune responses [*J. Immunol.* 162:3176–87 (1999); *Eur. J. Immunol.* 28:3867–77 (1998); *J. Exp. Med.* 186:941–53 (1997); *Eur. J. Immunol.* 26:989–94 (1996)].

A role for JNK activation in various cancers has also been established, suggesting the potential use of JNK inhibitors in cancer. For example, constitutively activated JNK is associated with HTLV-1 mediated tumorigenesis [*Oncogene* 13:135–42 (1996)]. The proliferative effects of bFGF and OSM on Kaposi's sarcoma (KS) cells are mediated by their activation of the JNK signaling pathway [*J. Clin. Invest.* 99:1798–804 (1997)]. Other proliferative effects of other cytokines implicated in KS proliferation, such as vascular endothelial growth factor (VEGF), IL-6 and TNFα, are also mediated by JNK. In addition, regulation of the c-jun gene in p210 BCR-ABL transformed cells corresponds with activity of JNK, suggesting a role for JNK inhibitors in the treatment for chronic myelogenous leukemia (CML) [*Blood* 92:2450–60 (1998)].

JNK1 and JNK2 are widely expressed in a variety of tissues. In contrast, JNK3, is selectively expressed in the brain and to a lesser extent in the heart and testis [Gupta et al., supra; Mohit et al., *Neuron* 14:67–78 (1995); Martin et al., *Brain Res. Mol. Brain Res.* 35:47–57 (1996)]. JNK3 has been linked to neuronal apoptosis induced by kainic acid, indicating a role of JNK in the pathogenesis of glutamate neurotoxicity. In the adult human brain, JNK3 expression is localized to a subpopulation of pyramidal neurons in the CA1, CA4 and subiculum regions of the hippocampus and layers 3 and 5 of the neocortex [Mohit et al., supra]. The CA1 neurons of patients with acute hypoxia showed strong nuclear JNK3-immunoreactivity compared to minimal, diffuse cytoplasmic staining of the hippocampal neurons from brain tissues of normal patients [Zhang et al., supra]. Thus, JNK3 appears to be involved involved in hypoxic and ischemic damage of CA1 neurons in the hippocampus.

In addition, JNK3 co-localizes immunochemically with neurons vulnerable in Alzheimer's disease [Mohit et al., supra]. Disruption of the JNK3 gene caused resistance of mice to the excitotoxic glutamate receptor agonist kainic acid, including the effects on seizure activity, AP-1 transcriptional activity and apoptosis of hippocampal neurons, indicating that the JNK3 signaling pathway is a critical component in the pathogenesis of glutamate neurotoxicity (Yang et al., *Nature*, 389:865–870 (1997)].

Based on these findings, JNK signaling, especially that of JNK3, has been implicated in the areas of apoptosis-driven neurodegenerative diseases such as Alzheimer's Disease, Parkinson's Disease, ALS (Amyotrophic Lateral Sclerosis), epilepsy and seizures, Huntington's Disease, traumatic brain injuries, as well as ischemic and hemorrhaging stroke.

There is a high unmet medical need to develop JNK specific inhibitors that are useful in treating the various conditions associated with JNK activation, especially considering the currently available, relatively inadequate treatment options for the majority of these conditions.

The Src-family of kinases are implicated in cancer, immune system dysfunction, and bone remodeling diseases. For general reviews, see Thomas and Brugge, *Annu. Rev. Cell Dev. Biol.* (1997) 13, 513; Lawrence and Niu, *Pharmacol. Ther.* (1998) 77, 81; Tatosyan and Mizenina, *Biochemistry* (Moscow) (2000) δ 5, 49; Boschelli et al., *Drugs of the Future* 2000, 25(7), 717, (2000).

Members of the Src family include the following eight kinases in mammals: Src, Fyn, Yes, Fgr, Lyn, Hck, Lck, Blk and Yrc. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. *Biochemistry* (Moscow) 65, 49–58 (2000).

Based on published studies, Src kinases are considered as potential therapeutic targets for various human diseases. Mice that are deficient in Src develop osteopetrosis, or bone build-up, because of depressed bone resorption by osteoclasts. This suggests that osteoporosis resulting from abnormally high bone resorption can be treated by inhibiting Src. Soriano et al., *Cell*, 69, 551 (1992) and Soriano et al., *Cell*, 64, 693 (1991).

Suppression of arthritic bone destruction has been achieved by the overexpression of CSK in rheumatoid synoviocytes and osteoclasts. Takayanagi et al., *J. Clin. Invest.*, 104, 137 (1999). CSK, or C-terminal Src kinase, phosphorylates and thereby inhibits Src catalytic activity. This implies that Src inhibition may prevent joint destruction that is characteristic in patients suffering from rheumatoid arthritis. Boschelli et al., *Drugs of the Future* 2000, 25(7), 717, (2000).

Src also plays a role in the replication of hepatitis B virus. The virally encoded transcription factor HBx activates Src in a step required for propagation of the virus. Klein et al., *EMBO J.*, 18, 5019, (1999) and Klein et al., *Mol. Cell. Biol.*, 17, 6427 (1997).

A number of studies have linked Src expression to cancers such as colon, breast, hepatic and pancreatic cancer, certain B-cell leukemias and lymphomas. Talamonti et al., *J. Clin. Invest.*, 91, 53 (1993); Lutz et al., *Biochem. Biophys. Res.* 243, 503 (1998); Rosen et al., *J. Biol. Chem.*, 261, 13754 (1986); Bolen et al., *Proc. Natl. Acad. Sci. USA*, 84, 2251 (1987); Masaki et al., *Hepatology*, 27, 1257 (1998); Biscardi et al., *Adv. Cancer Res.*, 76, 61 (1999); Lynch et al., *Leukemia*, 7, 1416 (1993); Furthermore, antisense Src expressed in ovarian and colon tumor cells has been shown to inhibit tumor growth. Wiener et al 1., *Clin. Cancer Res.*, 5, 2164 (1999); Staley et al., *Cell Growth Diff.*, 8, 269 (1997).

Other Src family kinases are also potential therapeutic targets. Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis. Molina et al., *Nature*, 357, 161 (1992). Hck, Fgr and Lyn have been identified as important mediators of integrin signaling in myeloid leukocytes. Lowell et al., *J. Leukoc. Biol.*, 65, 313 (1999). Inhibition of these kinase mediators may therefore be useful for treating inflammation. Boschelli et al., *Drugs of the Future* 2000, 25(7), 717, (2000).

Glycogen synthase kinase-3 (GSK-3) is a serine/threonine protein kinase comprised of α and β isoforms that are each encoded by distinct genes [Coghlan et al., *Chemistry & Biology*, 7, 793–803 (2000); Kim and Kimmel, *Curr. Opinion Genetics Dev.*, 10, 508–514 (2000)]. GSK-3 has been implicated in various diseases including diabetes, Alzheimer's disease, CNS disorders such as manic depressive disorder and neurodegenerative diseases, and cardiomyocete hypertrophy [WO 99/65897; WO 00/38675; and Haq et al., *J. Cell Biol.* (2000) 151, 117]. These diseases may be caused by, or result in, the abnormal operation of certain cell signaling pathways in which GSK-3 plays a role. GSK-3 has been found to phosphorylate and modulate the activity of a number of regulatory proteins. These include glycogen synthase which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-Myc, c-Myb, CREB, and CEPBα. These diverse targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS*, 93, 8455–9 (1996); Cross et al., *Biochem. J.*, 303, 21–26 (1994); Cohen, *Biochem. Soc. Trans.*, 21, 555–567 (1993); Massillon et al., *Biochem J.* 299, 123–128 (1994)]. However, in a diabetic patient where the insulin response is impaired, glycogen synthesis and glucose uptake fail to increase despite the presence of relatively high blood levels of insulin. This leads to abnormally high blood levels of glucose with acute and long term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [WO 00/38675]. Therapeutic inhibitors of GSK-3 are therefore potentially useful for treating diabetic patients suffering from an impaired response to insulin.

GSK-3 activity has also been associated with Alzheimer's disease. This disease is characterized by the well-known β-amyloid peptide and the formation of intracellular neurofibrillary tangles. The neurofibrillary tangles contain hyperphosphorylated Tau protein where Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Current Biology* 4, 1077–86 (1994); Brownlees et al., *Neuroreport* 8, 3251–55 (1997)]. Therefore, it is believed that GSK-3 activity may promote generation of the neurofibrillary tangles and the progression of Alzheimer's disease.

Another substrate of GSK-3 is β-catenin which is degradated after phosphorylation by GSK-3. Reduced levels of β-catenin have been reported in schizophrenic patients and have also been associated with other diseases related to increase in neuronal cell death [Zhong et al., *Nature*, 395, 698–702 (1998); Takashima et al., *PNAS*, 90, 7789–93 (1993); Pei et al., *J. Neuropathol. Exp*, 56, 70–78 (1997)].

Cyclin-dependent kinases (CDKs) are serine/threonine protein kinases consisting of a β-sheet rich amino-terminal lobe and a larger carboxy-terminal lobe which is largely α-helical. The CDKs display the 11 subdomains shared by all protein kinases and range in molecular mass from 33 to 44 kD. This family of kinases, which includes CDK1, CKD2, CDK4, and CDK6, requires phosphorylation at the residue corresponding to CDK2 Thr160 in order to be fully active [Meijer, L., *Drug Resistance Updates*, 3, 83–88 (2000)].

Each CDK complex is formed from a regulatory cyclin subunit (e.g., cyclin A, B1, B2, D1, D2, D3, and E) and a catalytic kinase subunit (e.g., CDK1, CDK2, CDK4, CDK5, and CDK6). Each different kinase/cyclin pair functions to regulate the different and specific phases of the cell cycle known as the G1, S, G2, and M phases [Nigg, E., *Nature Reviews*, 2, 21–32 (2001); Flatt, P., Pietenpol, J., *Drug Metabolism Reviews*, 32, 283–305 (2000)].

The CDKs have been implicated in cell proliferation disorders, particularly in cancer. Cell proliferation is a result of the direct or indirect deregulation of the cell division cycle and the CDKs play a critical role in the regulation of the various phases of this cycle. For example, the overexpression of cyclin D1 is commonly associated with numerous human cancers including breast, colon, hepatocellular carcinomas and gliomas [Flatt, P., Pietenpol, J., *Drug Metabolism Reviews*, 32, 283–305 (2000)]. The CDK2/cyclin E complex plays a key role in the progression from the early $G_1$ to S phases of the cell cycle and the overexpression of cyclin E has been associated with various solid tumors. Therefore, inhibitors of cyclins D1, E, or their associated CDKs are useful targets for cancer therapy [Kaubisch, A., Schwartz, G., *The Cancer Journal*, 6, 192–212 (2000)].

CDKs, especially CDK2, also play a role in apoptosis and T-cell development. CDK2 has been identified as a key regulator of thymocyte apoptosis [Williams, O., et al, *European Journal of Immunology*, 709–713 (2000)]. Stimulation of CDK2 kinase activity is associated with the progression of apoptosis in thymocytes, in response to specific stimuli. Inhibition of CDK2 kinase activity blocks this apoptosis resulting in the protection of thymocytes.

In addition to regulating the cell cycle and apoptosis, the CDKs are directly involved in the process of transcription. Numerous viruses require CDKs for their replication process. Examples where CDK inhibitors restrain viral replication include human cytomegakovirus, herpes virus, and varicella-zoster virus [Meijer, L., *Drug Resistance Updates*, 3, 83–88 (2000)].

Inhibition of CDK is also useful for the treatment of neurodegenerative disorders such as Alzheimer's disease. The appearance of Paired Helical Filaments (PHF), associated with Alzheimer's disease, is caused by the hyperphosphorylation of Tau protein by CDK5/p25 [Meijer, L., *Drug Resistance Updates*, 3, 83–88 (2000)].

As a result of the biological importance of protein kinases, there is current interest in therapeutically effective protein kinase inhbitors. Certain aryl substituted 2-aminopyrimidines are known as protein kinase inhibitors. See [U.S. Pat. Nos. 5,958,935, 5,863,924, 5,612,340, and PCT publication WO 01/29009].

Accordingly, there is still a great need to develop potent inhibitors of JNKs and Src family kinases, including JNK3, Src, and Lck inhibitors, and of GSK3 and CDK2 inhibitors that are useful in treating various diseases or conditions associated with JNK3, Src, Lck, GSK3, and CDK2 activation.

SUMMARY OF THE INVENTION

It has now been found that compounds of this invention and pharmaceutical compositions thereof are effective as inhibitors of c-Jun N-terminal kinases (JNK), Src, Lck, GSK3, and CDK2. These compounds have the general formulae I and II:

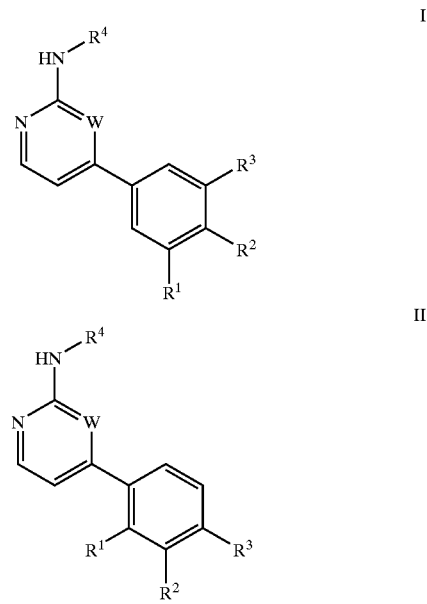

or a pharmaceutically acceptable derivative thereof, wherein W is nitrogen or CH and $R^1$, $R^2$, $R^3$, and $R^4$ are as described below.

These compounds and pharmaceutical compositions thereof are useful for treating or preventing a variety of disorders, such as heart disease, diabetes, Alzheimer's disease, immunodeficiency disorders, inflammatory diseases, allergic diseases, autoimmune diseases, destructive bone disorders such as osteoporosis, proliferative disorders, infectious diseases and viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. The compositions are especially useful for disorders such as chronic myelogenous leukemia (CML), rheumatoid arthritis, asthma, osteoarthritis, ischemia, cancer, liver disease including hepatic ischemia, heart disease such as myocardial infarction and congestive heart failure, pathologic immune conditions involving T cell activation and neurodegenerative disorders.

DETAILED DESCRIPTION OF THE INVENTION

The present invention relates to a compound of formula I or II:

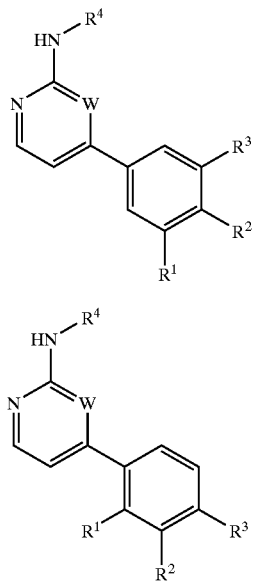

or a pharmaceutically acceptable derivative thereof, wherein:

each W is independently selected from nitrogen or CH;
each $R^1$, $R^2$, and $R^3$ is independently selected from halogen, QR, $Q_{(n)}$CN, $Q_{(n)}NO_2$, or $Q_{(n)}Ar^2$; wherein:
  $R^1$ and $R^2$ or $R^2$ and $R^3$ are optionally taken together to form a 4–8 membered saturated, partially unsaturated, or fully unsaturated ring having 0–3 heteroatoms independently selected from nitrogen, oxygen, or sulfur;
n is zero or one;
Q is a $C_{1-4}$ alkylidene chain wherein one methylene unit of Q is optionally replaced by O, S, NR, NRCO, NRCONR, $NRCO_2$, CO, $CO_2$, CONR, OC(O)NR, $SO_2$, $SO_2NR$, $NRSO_2$, $NRSO_2NR$, C(O)C(O), or $C(O)CH_2C(O)$;
each R is independently selected from hydrogen or an optionally substituted $C_1$–$C_4$ aliphatic, wherein:
  two R bound to the same nitrogen atom are optionally taken together with the nitrogen atom to form a 3–7 membered saturated, partially unsaturated, or fully unsaturated ring having 1–2 additional heteroatoms independently selected from nitrogen, oxygen, or sulfur;
$R^4$ is $Ar^1$, $T$-$Ar^2$, or $T_{(n)}$-$Ar^3$;
T is a $C_{1-2}$ alkylidene chain wherein one methylene unit of T is optionally replaced by O, NR, NRCO, NRCONR, $NRCO_2$, CO, $CO_2$, CONR, OC(O)NR, $SO_2$, $SO_2NR$, $NRSO_2$, $NRSO_2NR$, C(O)C(O), or $C(O)CH_2C(O)$;
$Ar^1$ is a 5–6 membered monocyclic or 8–10 membered bicyclic saturated, partially unsaturated, or fully unsaturated ring system; wherein:
  $Ar^1$ is optionally substituted with up to five substituents, wherein the first substituent is selected from $R^x$ or $R^5$ and wherein any additional substituents are independently selected from $R^5$;
each $R^x$ is independently selected from a 5–6 membered aryl ring having 0–3 heteroatoms selected from nitrogen, oxygen, or sulfur, wherein:
  $R^x$ is optionally substituted with 1–3 $R^5$;
each $R^5$ is independently selected from R, halogen, $NO_2$, CN, OR, SR, $N(R)_2$, NRC(O)R, $NRC(O)N(R)_2$, $NRCO_2R$, C(O)R, $CO_2R$, $C(O)N(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$;
$Ar^2$ is a 5–6 membered saturated, partially unsaturated, or fully unsaturated monocyclic ring having 0–3 heteroatoms independently selected from nitrogen, oxygen, or sulfur, or an 8–10 membered saturated, partially unsaturated, or fully unsaturated bicyclic ring system having 0–5 heteroatoms independently selected from nitrogen, oxygen, or sulfur; wherein:
  $Ar^2$ is optionally substituted with up to five substituents, wherein the first substituent is selected from $R^x$ or $R^5$ and wherein any additional substituents are independently selected from $R^5$;
$Ar^3$ is a 6-membered aryl ring having 0–2 nitrogens, wherein:
  $Ar^3$ is substituted with one Z-$R^6$ group and optionally substituted with 1–3 $R^5$;
Z is a $C_1$–$C_6$ alkylidene chain wherein up to two non-adjacent methylene units of Z are optionally replaced by Co, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and
$R^6$ is selected from $Ar^2$, R, halogen, $NO_2$, CN, OR, SR, $N(R)_2$, NRC(O)R, $NRC(O)N(R)_2$, $NRCO_2R$, C(O)R, $CO_2R$, OC(O)R, $C(O)N(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$;
provided that:
(i) when $R^4$ is phenyl substituted with two OR, wherein R is not hydrogen, the two OR occupy positions on the phenyl ring other than simultaneously meta and para; and
(ii) said compound is other than a compound of formula III

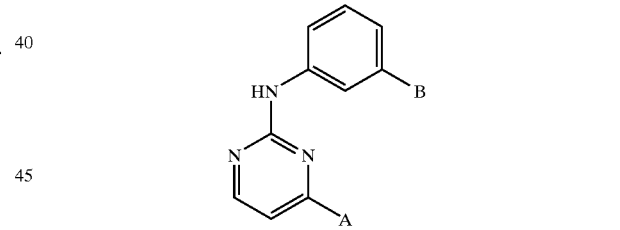

wherein:
A is a phenyl ring substituted with one or more groups selected from halogen, CN, $OC(O)NH_2$, $CO_2R^{10}$, $COR^{10}$, $SO_2N(R^{10})_2$, $N(R^{10})_2$, $OR^{10}$, or fluoro-alkyl, wherein
each $R^{10}$ is independently selected from hydrogen or a $C_1$–$C_7$ alkyl group optionally substituted with $NH_2$, NH($C_1$–$C_7$ alkyl), or N($C_1$–$C_7$ alkyl)$_2$; and
B is selected from halogen, CN, $OC(O)NH_2$, $CO_2R^{10}$, $COR^{10}$, $SO_2N(R^{10})_2$, $N(R^{10})_2$, $OR^{10}$, or fluoro-($C_1$–$C_7$ alkyl).

As used herein, the following definitions shall apply unless otherwise indicated.

The phrase "optionally substituted" is used interchangeably with the phrase "substituted or unsubstituted". Unless otherwise indicated, an optionally substituted group may have a substituent at each substitutable position of the group, and each substitution is independent of the other.

The term "aliphatic" or "aliphatic group" as used herein means a straight-chain or branched $C_1$–$C_{12}$ hydrocarbon chain that is completely saturated or that contains one or more units of unsaturation, or a monocyclic $C_3$–$C_8$ hydrocarbon or bicyclic $C_8$–$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3–7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0–3 heteroatoms selected from oxygen, sulfur or nitrogen, the nitrogen may be N (as in 3,4-dihydro-2H-pyrrolyl), NH (as in pyrrolidinyl) or NR$^+$ (as in N-substituted pyrrolidinyl).

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aliphatic group or a non-aromatic heterocyclic ring may contain one or more substituents. Suitable substituents on the saturated carbon of an aliphatic group or of a non-aromatic heterocyclic ring are selected from halogen, oxo, —R°, —OR°, —SR°, 1,2-methylene-dioxy, 1,2-ethylenedioxy, phenyl (Ph) optionally substituted with R°, —O(Ph) optionally substituted with R°, —CH$_2$(Ph) optionally substituted with R°, —CH$_2$CH$_2$(Ph), optionally substituted with R°, —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O) R°, —C(O)CH$_2$C(O)R°, —CO$_2$R°, —C(O)R°, —C(O)N (R°)$_2$, —OC(O)N(R°)$_2$, —S(O)$_2$R°, —SO$_2$N(R°)$_2$, —S(O) R°, —NR°SO$_2$N(R°)$_2$, —NR°SO$_2$R°, —C(=S)N(R°)$_2$, —C(=NH)—N(R°)$_2$, =S, =NNHR°, =NN(R°)$_2$, =NNHC(O)R°, =NNHCO$_2$(alkyl), =NNHSO$_2$(alkyl), =NR° or —(CH$_2$)$_y$NHC(O)R°, wherein each R° is independently selected from hydrogen, optionally substituted $C_{1-6}$ aliphatic, an unsubstituted 5–6 membered heteroaryl or heterocyclic ring, phenyl, —O(Ph), or —CH$_2$(Ph). Optional substituents on the aliphatic group of R° are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo C$_{1-4}$ aliphatic.

The term "alkylidene chain" refers to a straight or branched carbon chain that may be fully saturated or have one or more units of unsaturation.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Preferred R$^1$, R$^2$, and R$^3$ groups of formulae I and II are selected from halogen, QR or QAr$^2$, wherein Q is a $C_{1-3}$ alkylidene chain wherein one methylene unit of Q is optionally replaced by —O—, —S—, —NHCO—, or —NR—, and Ar$^2$ is an optionally substituted 5–6 membered saturated, partially unsaturated, or fully unsaturated ring having 0–2 heteroatoms independently selected from nitrogen, oxygen, or sulfur. Most preferred R$^1$, R$^2$, and R$^3$ groups are selected from OH, OCH$_3$, OCH$_2$CH$_3$, NHCOMe, NH$_2$, NH(C$_{1-4}$ aliphatic), N(C$_{1-4}$ aliphatic)$_2$, O(CH$_2$)$_2$morpholin-4-yl, O(CH$_2$)$_2$NH$_2$, O(CH$_2$)$_2$NH(C$_{1-4}$ aliphatic), O(CH$_2$)$_2$N(C$_{1-4}$ aliphatic)$_2$, bromo, chloro, or fluoro. Other preferred compounds of formulae I and II are those where either R$^1$ and R$^2$, or R$^2$ and R$^3$ are taken together to form

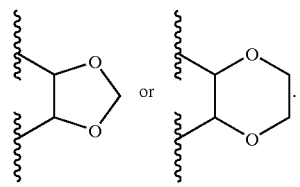

Most preferred Ar$^2$ groups are morpholin-4-yl, pyrrolidin-1-yl, piperidin-1-yl, thiomorpholin-4-yl, pyrazol-1-yl, or imidazol-1-yl.

Preferred R$^4$ groups of formulae I and II are selected from a 6-membered saturated, partially unsaturated, or aryl ring having 0–3 nitrogens, a 9–10 membered bicyclic aryl ring having 0–2 nitrogens, or a 5 membered heteroaryl ring having 2–3 heteroatoms independently selected from nitrogen, oxygen, or sulfur, wherein each ring is optionally substituted. More preferred $R^4$ groups of formulae I and II are substituted rings selected from phenyl, cyclohexyl, naphthyl, pyridyl, pyrimidinyl, triazinyl, thiazolyl, thiadiazolyl, pyrazolyl, isoxazolyl, indazolyl, or benzimidazolyl.

Preferred substituents on $R^4$ are independently selected from R, halogen, $NO_2$, OR, $N(R)_2$, $R^x$, or $Z-R^6$, wherein R is hydrogen or optionally substituted $C_{1-4}$ aliphatic. Preferred Z groups of formulae I and II are selected from a $C_{1-4}$ alkylidene chain wherein one methylene unit of Z is optionally replaced by —O—, —S—, —$SO_2$—, or —NH—. Preferred $R^6$ groups are selected from optionally substituted phenyl, pyridyl, and pyrimidinyl. Preferred $R^x$ substituents on $R^4$ are selected from phenyl, pyridyl, and pyrimidinyl wherein $R^x$ is optionally substituted with 1–2 $R^5$. More preferred substituents on $R^4$ are selected from chloro, fluoro, bromo, methyl, ethyl, t-butyl, isopropyl, cyclopropyl, nitro, OMe, OEt, $CF_3$, $NH_2$, benzyl, benzyloxy, OH, methylene dioxy, $SO_2NH_2$, phenoxy, O-pyridinyl, $SO_2$phenyl, nitrophenoxy, aminophenoxy, S-dimethylpyrimidine, NHphenyl, NH-methoxyphenyl, pyridinyl, aminophenyl, phenol, chloro-fluoro-phenyl, dimethylaminophenyl, $CF_3$-phenyl, dimethylphenyl, chlorophenyl, fluorophenyl, methoxyphenoxy, chlorophenoxy, ethoxyphenoxy, and fluorophenoxy. Most preferred $R^4$ groups of formulae I and II are those depicted in Tables 1, 2, and 3.

A preferred embodiment relates to a compound of formula I-a or II-a:

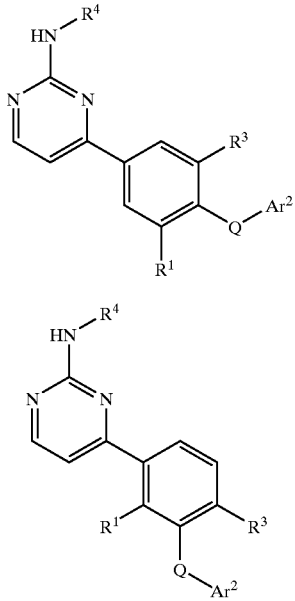

or a pharmaceutically acceptable derivative thereof, wherein $R^1$, $R^3$, $R^4$, Q, and $Ar^2$ are as defined above.

Preferred $R^1$, $R^3$, $R^4$, $Ar^2$, and Q are as described above for compounds of formulae I and II.

Most preferred compounds of I-a and II-a are those of formula I-a' and II-a':

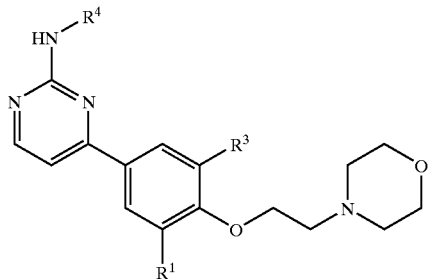

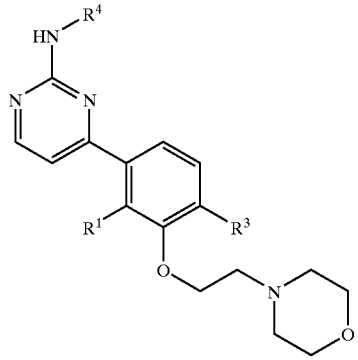

or a pharmaceutically acceptable derivative thereof, wherein $R^1$, $R^3$, and $R^4$ are as defined above.

Preferred $R^1$, $R^3$, and $R^4$ groups of formulae I-a' and II-a' are those described above for compounds of formulae I and II.

Another preferred embodiment relates to a compound of formula I-b or II-b:

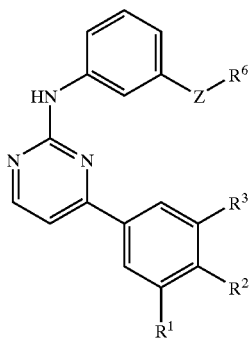

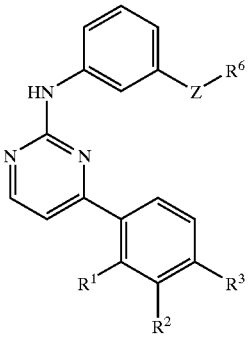

or a pharmaceutically acceptable derivative thereof, wherein $R^1$, $R^2$, $R^3$, Z, and $R^6$ are as defined above.

Preferred $R^1$, $R^2$, $R^3$, Z, and $R^6$ are as described above for compounds of formulae I and II.

Exemplary structures of formula I, wherein W is nitrogen, are set forth in Table 1 below.

TABLE 1
Compounds of Formula I
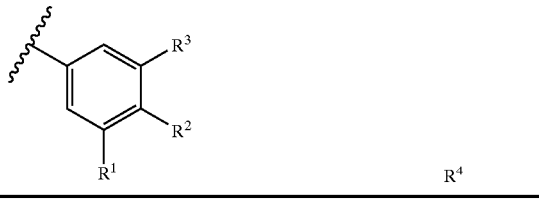
| No. | R¹, R², R³ | R⁴ |
|---|---|---|
| I-1 | 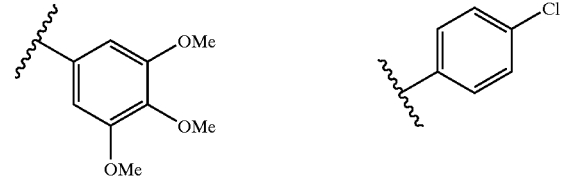 | 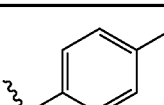 |
| I-2 | 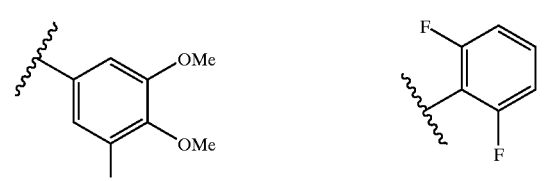 | 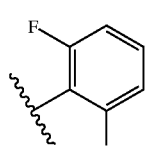 |
| I-3 | 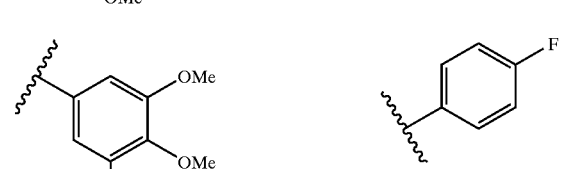 | 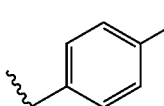 |
| I-4 | 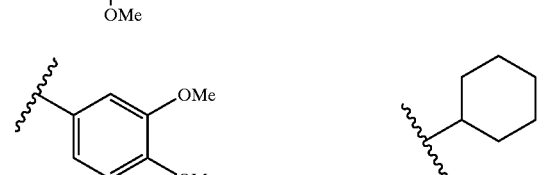 | 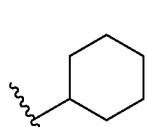 |
| I-5 |  | 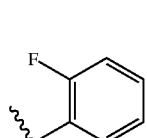 |
| I-6 | 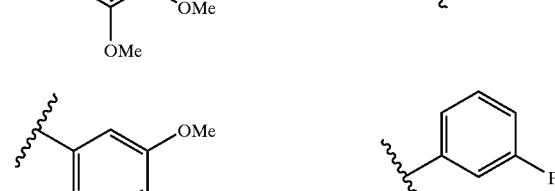 |  |
| I-7 | 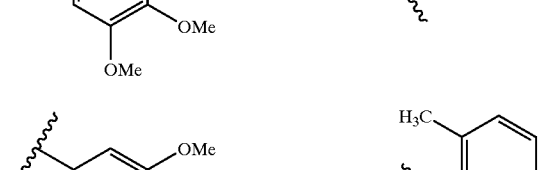 | 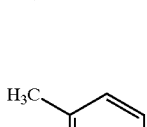 |

TABLE 1-continued

Compounds of Formula I

| No. | (aryl with R¹, R², R³) | R⁴ |
|---|---|---|
| I-8 | 3,4,5-tri-OMe phenyl | 2,6-dimethylphenyl |
| I-9 | 3,4,5-tri-OMe phenyl | 4-chlorophenyl |
| I-10 | 3,4,5-tri-OMe phenyl | 4-methylthiazol-2-yl |
| I-11 | 3,4,5-tri-OMe phenyl | 4-nitrophenyl |
| I-12 | 3,4,5-tri-OMe phenyl | 3,5-dimethoxyphenyl |
| I-13 | 3,4,5-tri-OMe phenyl | 2,3-difluorophenyl |

TABLE 1-continued
Compounds of Formula I
| No. | R¹/R²/R³ aryl | R⁴ |
|---|---|---|
| I-14 | 3,4,5-tri-OMe phenyl 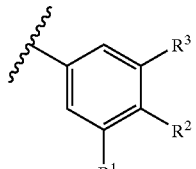 | 4-F phenyl 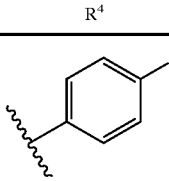 |
| I-15 | 3,4,5-tri-OMe phenyl 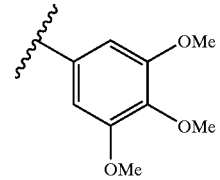 | phenyl 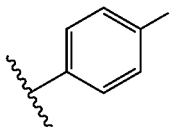 |
| I-16 | 3,4,5-tri-OMe phenyl 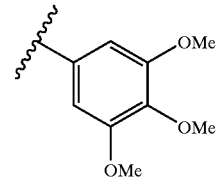 | 2-CH₃ phenyl 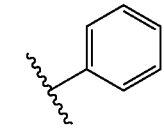 |
| I-17 | 3,4,5-tri-OMe phenyl 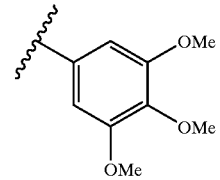 | 4-CH₃ phenyl 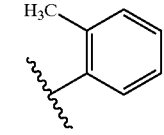 |
| I-18 | 3,4,5-tri-OMe phenyl 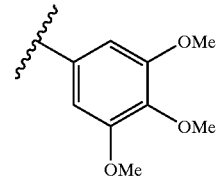 | 3-Cl phenyl 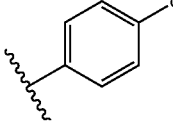 |
| I-19 | 3,4,5-tri-OMe phenyl 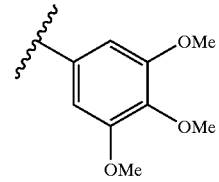 | 3-CF₃ phenyl 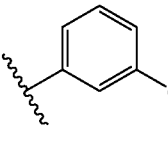 |
| I-20 | 3,4,5-tri-OMe phenyl 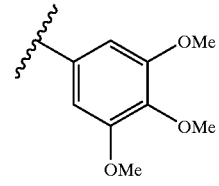 | 3-OCH₃ phenyl 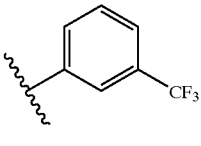 |

TABLE 1-continued
Compounds of Formula I
| No. | | $R^4$ |
|---|---|---|
| I-21 | 3,4,5-triOMe phenyl | 4-OCH₃ phenyl |
| I-22 | 3,4,5-triOMe phenyl | 3,4,5-triF phenyl |
| I-23 | 3,4,5-triOMe phenyl | 3,5-diCl phenyl |
| I-24 | 3,4,5-triOMe phenyl | 3,5-diCH₃ phenyl |
| I-25 | 3,4,5-triOMe phenyl | 3,4-diCH₃ phenyl |
| I-26 | 4-OMe-benzodioxole | phenyl |
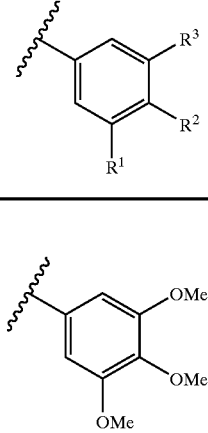
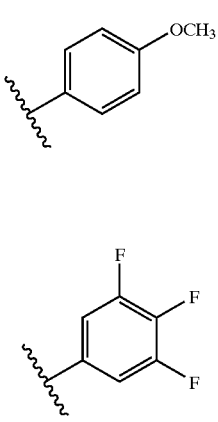
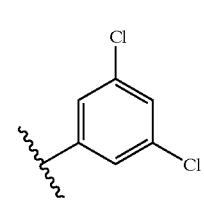
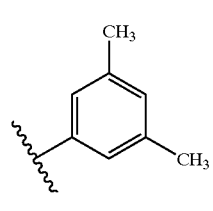
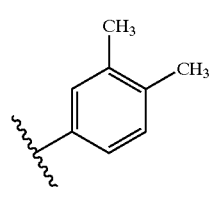
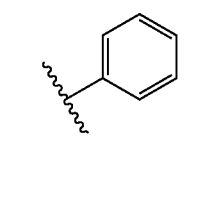

TABLE 1-continued
Compounds of Formula I
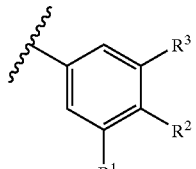
| No. | R¹ (structure) | R⁴ |
|-----|----------------|-----|
| I-27 | 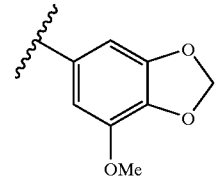 | 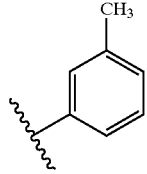 |
| I-28 | 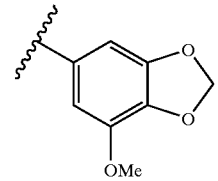 | 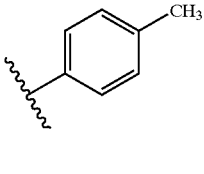 |
| I-29 | 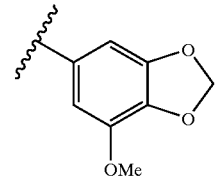 | 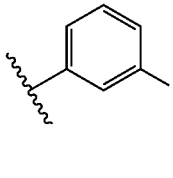 |
| I-30 | 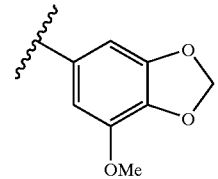 | 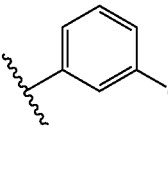 |
| I-31 | 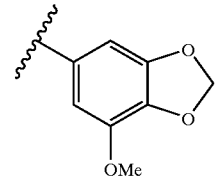 | 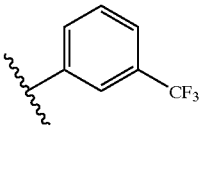 |
| I-32 | 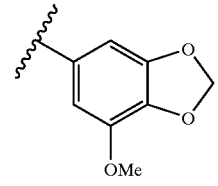 | 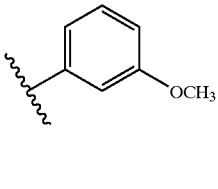 |
| I-33 | 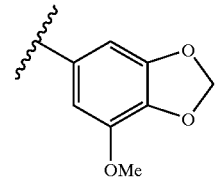 | 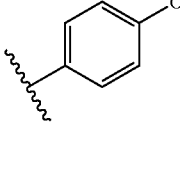 |

TABLE 1-continued

Compounds of Formula I

| No. | (Ar with R¹, R², R³) | R⁴ |
|---|---|---|
| I-34 | 3,4,5-triOMe phenyl | 4-NH₂ phenyl |
| I-35 | 3,4,5-triOMe phenyl | 4-OCH₃, 3-Cl phenyl |
| I-36 | 3,4,5-triOMe phenyl | 3-NO₂ phenyl |
| I-37 | 3,4,5-triOMe phenyl | benzyl (-CH₂-phenyl) |
| I-38 | 3,4,5-triOMe phenyl | 3-(OCH₂Ph) phenyl |
| I-39 | 3,5-diOMe-4-(O-CH₂CH₂-morpholino) phenyl | 3-Cl phenyl |

TABLE 1-continued
Compounds of Formula I
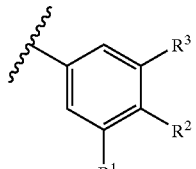
| No. | R¹, R², R³ | R⁴ |
|---|---|---|
| I-40 |  | 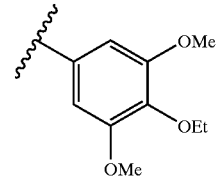 |
| I-41 | 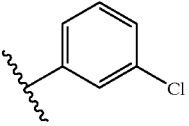 | 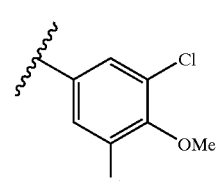 |
| I-42 | 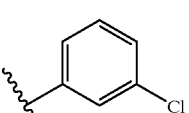 | 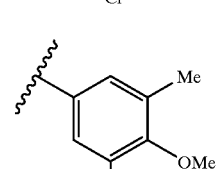 |
| I-43 | 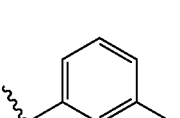 | 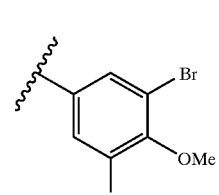 |
| I-44 | 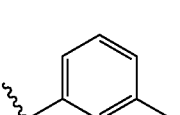 | 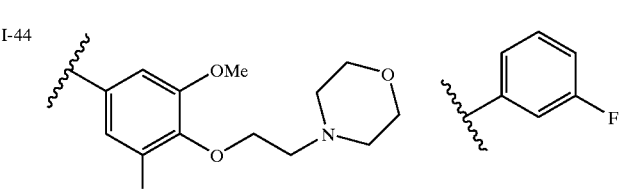 |
| I-45 | 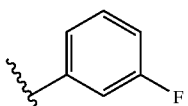 | 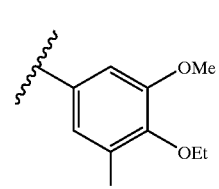 |
| I-46 | 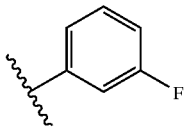 | 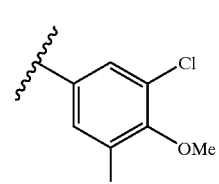 |

TABLE 1-continued

Compounds of Formula I

| No. | | $R^4$ |
|---|---|---|
| I-47 | 3,5-diMe-4-OMe phenyl | 3-F phenyl |
| I-48 | 3,5-diBr-4-OMe phenyl | 3-F phenyl |
| I-49 | 3,5-diOMe-4-(O-CH$_2$CH$_2$-morpholine) phenyl | 3-OCH$_3$ phenyl |
| I-50 | 3,5-diOMe-4-OEt phenyl | 3-OCH$_3$ phenyl |
| I-51 | 3,5-diCl-4-OMe phenyl | 3-OCH$_3$ phenyl |
| I-52 | 3,5-diMe-4-OMe phenyl | 3-OCH$_3$ phenyl |

US 6,949,544 B2

TABLE 1-continued

Compounds of Formula I

| No. | R¹, R², R³ group | R⁴ |
|---|---|---|
| I-53 | 3,5-di-OMe, 4-O(CH₂)₂-morpholine phenyl | 3-methylphenyl |
| I-54 | 3,5-di-OMe, 4-OEt phenyl | 3-methylphenyl |
| I-55 | 3,5-di-Cl, 4-OMe phenyl | 3-methylphenyl |
| I-56 | 3,4,5-tri-OMe phenyl | 3-benzyloxyphenyl |
| I-57 | 3,4,5-tri-OMe phenyl | 3-aminophenyl |
| I-58 | 3,4,5-tri-OMe phenyl | 3-hydroxyphenyl |
| I-59 | 3,4,5-tri-OMe phenyl | 3-bromophenyl |

TABLE 1-continued

Compounds of Formula I

| No. | | R⁴ |
|---|---|---|
| I-60 | 3,4,5-triOMe phenyl | 3-fluorophenyl (2-F) |
| I-61 | 3,4,5-triOMe phenyl | 6-chloropyridin-3-yl |
| I-62 | 3,4,5-triOMe phenyl | naphthalen-2-yl |
| I-63 | 3,4,5-triOMe phenyl | benzo[1,3]dioxol-5-yl |
| I-64 | 3,4,5-triOMe phenyl | 3,4-dimethoxyphenyl |
| I-65 | 3,4,5-triOMe phenyl | 1H-benzimidazol-2-yl |

TABLE 1-continued
Compounds of Formula I
| No. | 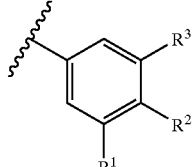 | R⁴ |
|---|---|---|
| I-66 | | |
| I-67 | | |
| I-68 | | |
| I-69 | | |
| I-70 | | |
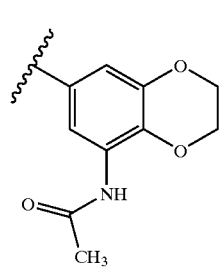

TABLE 1-continued
Compounds of Formula I
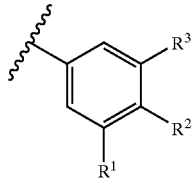
| No. | R¹/R²/R³ | R⁴ |
|---|---|---|
| I-71 |  | 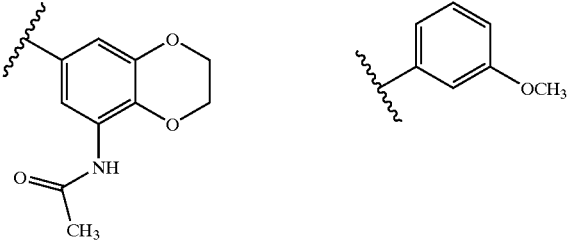 |
| I-72 | 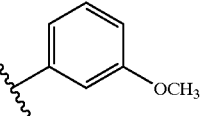 | 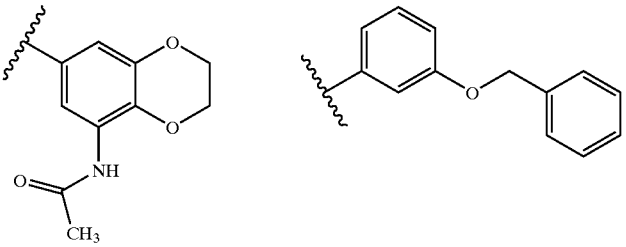 |
| I-73 | 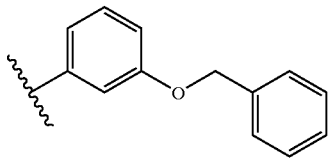 | 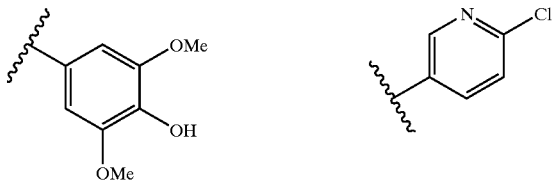 |
| I-74 | 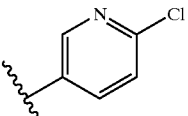 | 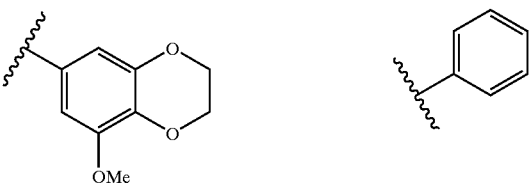 |
| I-75 | 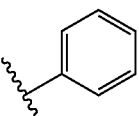 | 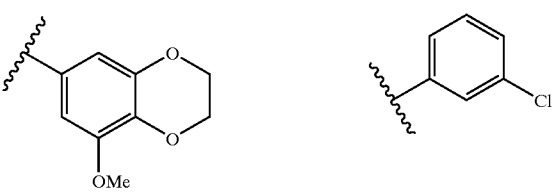 |
| I-76 | 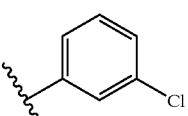 | 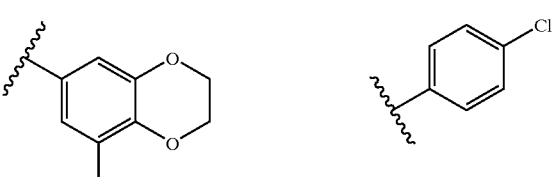 |

TABLE 1-continued
Compounds of Formula I
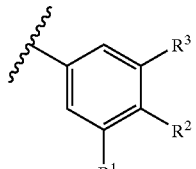
| No. | | R⁴ |
|---|---|---|
| I-77 | 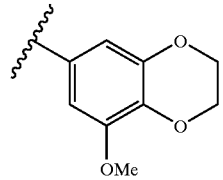 | 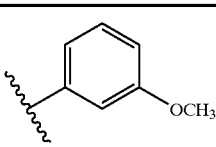 |
| I-78 | 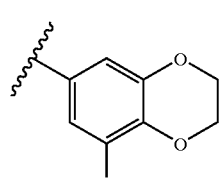 | 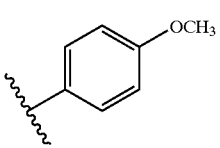 |
| I-79 | 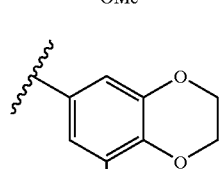 | 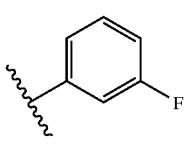 |
| I-80 | 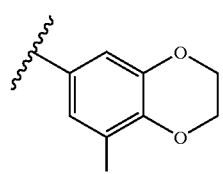 | 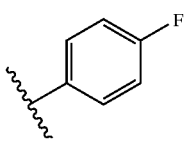 |
| I-81 | 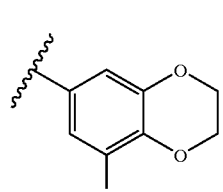 | 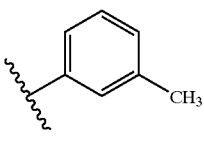 |
| I-82 | 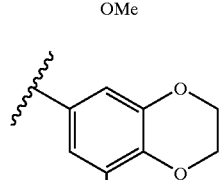 | 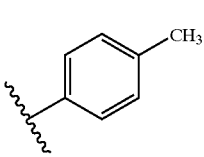 |
| I-83 | 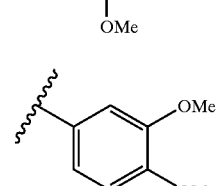 | 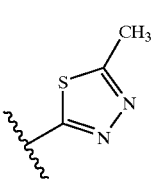 |

TABLE 1-continued

Compounds of Formula I

| No. | (aryl with R¹, R², R³) | R⁴ |
|---|---|---|
| I-84 | 3,4,5-tri-OMe phenyl | 5-ethyl-1,3,4-thiadiazol-2-yl |
| I-85 | 3,4,5-tri-OMe phenyl | thiazol-2-yl |
| I-86 | 3,4,5-tri-OMe phenyl | 1-ethyl-1H-pyrazol-3-yl (NH tautomer shown) |
| I-87 | 3,4,5-tri-OMe phenyl | 3,4-dimethylisoxazol-5-yl |
| I-88 | 3,4,5-tri-OMe phenyl | 3-methyl-1H-pyrazol-5-yl |
| I-89 | 3,4,5-tri-OMe phenyl | 3-(N,N-dimethylamino)phenyl |

TABLE 1-continued
Compounds of Formula I
| No. | | $R^4$ |
|---|---|---|
| I-90 | 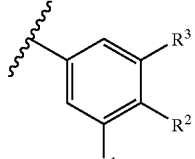 3,5-diCl, 4-OMe phenyl | 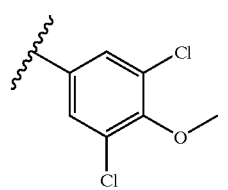 3,5-dimethylphenyl |
| I-91 | 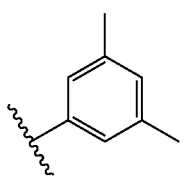 3,5-diOMe, 4-OEt phenyl | 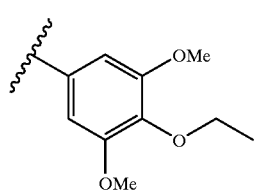 3,5-dimethylphenyl |
| I-92 | 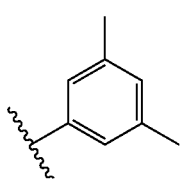 3,5-diCl, 4-OMe phenyl | 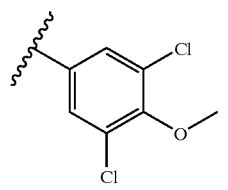 3,5-diOMe phenyl |
| I-93 | 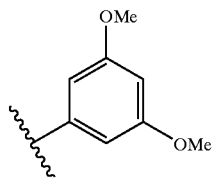 3,5-diOMe, 4-OEt phenyl | 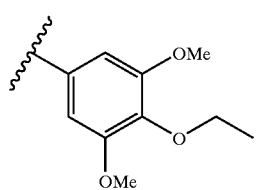 3,5-diOMe phenyl |
| I-94 | 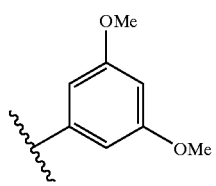 3,4,5-triOMe phenyl | 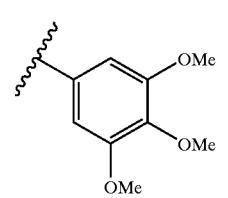 3-SO$_2$NH$_2$ phenyl |

Exemplary structures of formula I, wherein W is CH, are set forth in Table 2 below.

TABLE 2

Compounds of Formula I

| No. | (R¹, R², R³ substituted phenyl) | R⁴ |
|---|---|---|
| I-96 | 3,4,5-tri-OMe phenyl | 4-OMe phenyl |
| I-97 | 3,4,5-tri-OMe phenyl | 3-Me phenyl |
| I-98 | 3,4,5-tri-OMe phenyl | 4-Me phenyl |
| I-99 | 3,4,5-tri-OMe phenyl | 4-NH₂ phenyl |
| I-100 | 3,4,5-tri-OMe phenyl | 2-F phenyl |
| I-101 | 3,4,5-tri-OMe phenyl | 3-F phenyl |

TABLE 2-continued

Compounds of Formula I

| No. | R¹, R², R³ | R⁴ |
|---|---|---|
| I-102 | 3,4,5-tri-OMe phenyl | 4-F phenyl |
| I-103 | 3,4,5-tri-OMe phenyl | 3,4-di-F phenyl |
| I-104 | 3,4,5-tri-OMe phenyl | 2,6-di-F phenyl |
| I-105 | 3,4,5-tri-OMe phenyl | 3,5-di-OMe phenyl |
| I-106 | 3,4,5-tri-OMe phenyl | 3-Cl phenyl |
| I-107 | 3,4,5-tri-OMe phenyl | 3-OMe phenyl |
| I-108 | 3,4,5-tri-OMe phenyl | 3,4-di-Me phenyl |

TABLE 2-continued

Compounds of Formula I

| No. | | R⁴ |
|---|---|---|
| I-109 | 3,4,5-tri-OMe phenyl | 3,5-di-Me phenyl |
| I-110 | 3,4,5-tri-OMe phenyl | 2,6-di-Me phenyl |
| I-111 | 3,4,5-tri-OMe phenyl | 3,5-di-Cl phenyl |
| I-112 | 3,4,5-tri-OMe phenyl | 3-Cl-4-OMe phenyl |
| I-113 | 3,4,5-tri-OMe phenyl | 3-NH₂ phenyl |
| I-114 | 3,5-di-Me-4-OMe phenyl | 3-Me phenyl |

TABLE 2-continued
Compounds of Formula I
| No. | 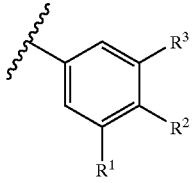 | R⁴ |
|---|---|---|
| I-115 |  | 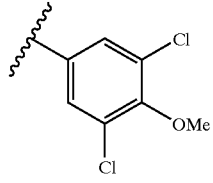 |
| I-116 | 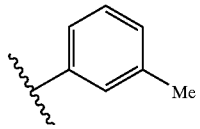 | 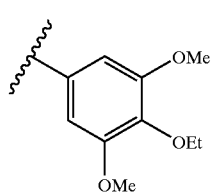 |
| I-117 | 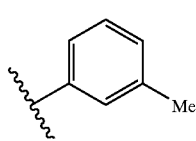 | 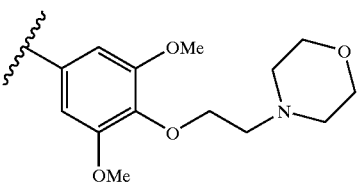 |
| I-118 | 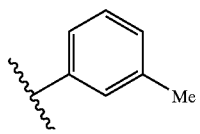 | 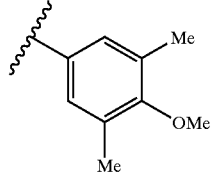 |
| I-119 | 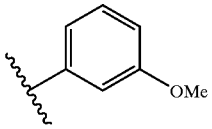 | 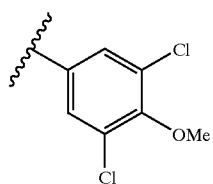 |
| I-120 | 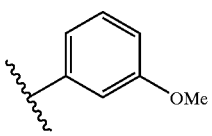 | 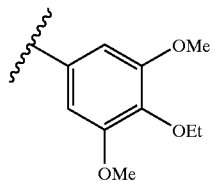 |
| I-121 | 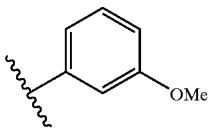 | 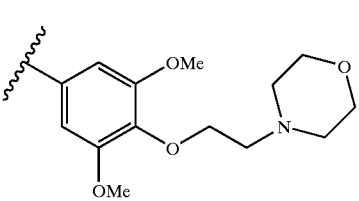 |

TABLE 2-continued
Compounds of Formula I
| No. | | R⁴ |
|---|---|---|
| I-122 | 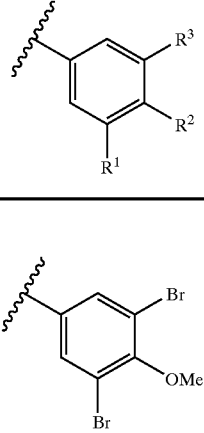 | 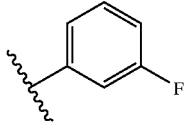 |
| I-123 | 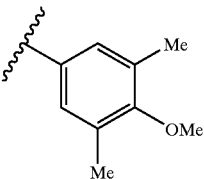 | 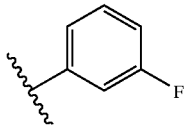 |
| I-124 | 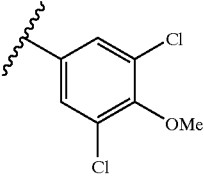 | 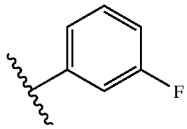 |
| I-125 | 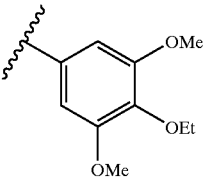 | 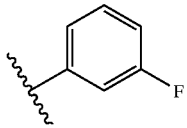 |
| I-126 | 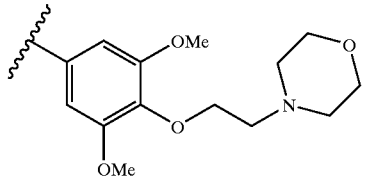 | 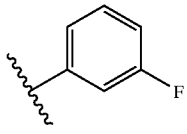 |
| I-127 | 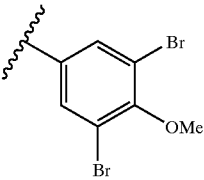 | 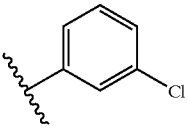 |

US 6,949,544 B2

TABLE 2-continued

Compounds of Formula I

| No. | R¹, R², R³ | R⁴ |
|---|---|---|
| I-128 | 3,5-diMe-4-OMe phenyl | 3-Cl phenyl |
| I-129 | 3,5-diCl-4-OMe phenyl | 3-Cl phenyl |
| I-130 | 3,5-diOMe-4-OEt phenyl | 3-Cl phenyl |
| I-131 | 3,5-diOMe-4-(O-CH₂CH₂-morpholino) phenyl | 3-Cl phenyl |
| I-132 | 3,4,5-triOMe phenyl | 4-NO₂ phenyl |
| I-133 | 3,4,5-triOMe phenyl | 4-NH₂ phenyl |
| I-134 | 4-OMe-benzo[1,3]dioxol-5-yl | 4-OMe phenyl |

TABLE 2-continued

Compounds of Formula I

| No. | | $R^4$ |
|---|---|---|
| I-135 | 3,4-methylenedioxy-7-OMe benzo | 3-OMe phenyl |
| I-136 | 3,4-methylenedioxy-7-OMe benzo | 3-F phenyl |
| I-137 | 3,4-methylenedioxy-7-OMe benzo | 4-Me phenyl |
| I-138 | 3,4,5-tri-OMe phenyl | 3,4,5-tri-F phenyl |
| I-139 | 3,4,5-tri-OMe phenyl | 3-CF$_3$ phenyl |
| I-140 | 3,4,5-tri-OMe phenyl | 4-Cl phenyl |

TABLE 2-continued

Compounds of Formula I

| No. | R¹/R²/R³ (aryl substitution pattern) | R⁴ |
|---|---|---|
| I-141 | 3,4,5-tri-OMe phenyl | 2-Me phenyl |
| I-142 | 3,4,5-tri-OMe phenyl | 4-hydroxycyclohexyl |
| I-143 | 3,4,5-tri-OMe phenyl | 2,6-diCl phenyl |
| I-144 | 3,4,5-tri-OMe phenyl | 2,3-diF phenyl |
| I-145 | 3,4,5-tri-OMe phenyl | 3-ethyl phenyl |
| I-146 | 3,4,5-tri-OMe phenyl | 3-Cl phenyl |
| I-147 | 3,4,5-tri-OMe phenyl | 2-Cl phenyl |

TABLE 2-continued
Compounds of Formula I
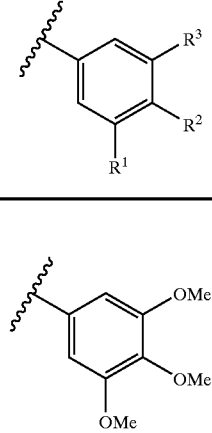
| No. | | R⁴ |
|---|---|---|
| I-148 | 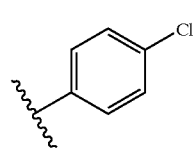 | 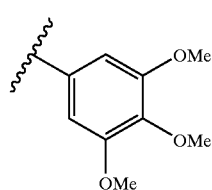 |
| I-149 | 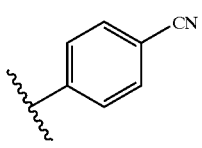 | 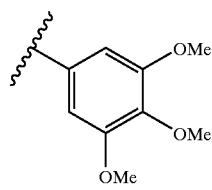 |
| I-150 | 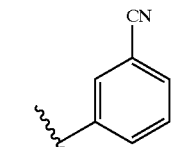 | 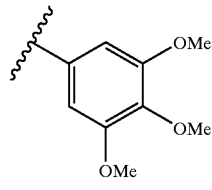 |
| I-151 | 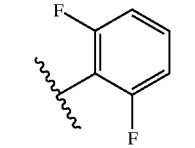 | 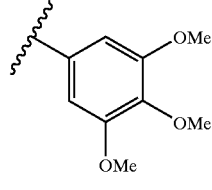 |
| I-152 | 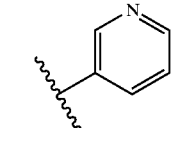 | 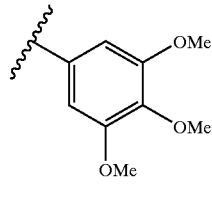 |
| I-153 | 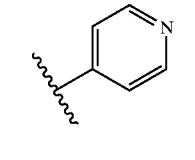 | |

TABLE 2-continued

Compounds of Formula I

| No. | (aryl with R¹, R², R³) | R⁴ |
|---|---|---|
| I-154 | 3,4,5-tri-OMe phenyl | 3-fluorophenyl |
| I-155 | 3,4,5-tri-OMe phenyl | phenyl |
| I-156 | 3,4,5-tri-OMe phenyl | 4-methylthiazol-2-yl |
| I-157 | 3,4,5-tri-OMe phenyl | 1-ethyl-3-methyl-1H-pyrazol-5-yl |
| I-158 | 3,4,5-tri-OMe phenyl | 4-ethylphenyl |
| I-159 | 3,4,5-tri-OMe phenyl | 2,4-difluorophenyl |

TABLE 2-continued
Compounds of Formula I
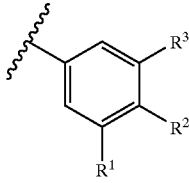
| No. | R¹ | R⁴ |
|---|---|---|
| I-160 | 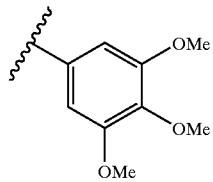 | 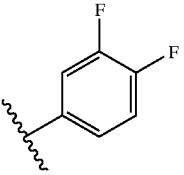 |
Exemplary structures of formula II, wherein W is nitrogen, are set forth in Table 3 below.
TABLE 3
Compounds of Formula II
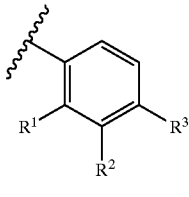
| No. | R² | TR⁴ |
|---|---|---|
| II-1 | 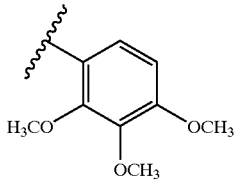 | 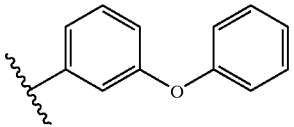 |
| II-2 | 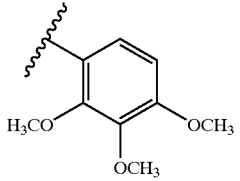 | 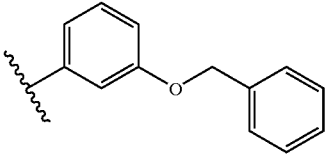 |
| II-3 | 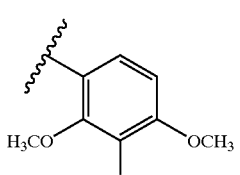 | 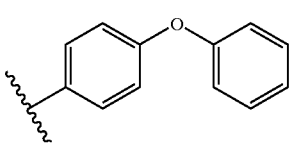 |

TABLE 3-continued

Compounds of Formula II

| No. | (R¹, R², R³ aryl) | TR⁴ |
|---|---|---|
| II-4 | 2,3,4-tri-OCH₃ phenyl | 4-NO₂ phenyl |
| II-5 | 2,3,4-tri-OCH₃ phenyl | 3-F phenyl |
| II-6 | 2,3,4-tri-OCH₃ phenyl | 3-OCH₃ phenyl |
| II-7 | 2,3,4-tri-OCH₃ phenyl | 4-F phenyl |
| II-8 | 2,3,4-tri-OCH₃ phenyl | 4-Cl phenyl |
| II-9 | 2,3,4-tri-OCH₃ phenyl | 3,4-di-F phenyl |
| II-10 | 2,3,4-tri-OCH₃ phenyl | 3-CH₃ phenyl |

TABLE 3-continued

Compounds of Formula II

| No. | (Ar with R¹, R², R³) | TR⁴ |
|-----|---------------------|-----|
| II-11 | R¹=OCH₃, R²=OCH₃, R³=OCH₃ | 4-methylphenyl |
| II-12 | R¹=OCH₃, R²=OCH₃, R³=OCH₃ | 4-methoxyphenyl |
| II-13 | R¹=OCH₃, R²=OCH₃, R³=OCH₃ | 4-(benzyloxy)phenyl |
| II-14 | R¹=OCH₃, R²=OCH₃, R³=OCH₃ | 3,5-dimethylphenyl |
| II-15 | 8-methoxy-2,3-dihydro-1,4-benzodioxin-5-yl | 3-phenoxyphenyl |
| II-16 | 8-methoxy-2,3-dihydro-1,4-benzodioxin-5-yl | 3-(benzyloxy)phenyl |

TABLE 3-continued

Compounds of Formula II

| No. | | TR⁴ |
|---|---|---|
| II-17 | | |
| II-18 | | |
| II-19 | | |
| II-20 | | |
| II-21 | | |

TABLE 3-continued

Compounds of Formula II

| No. | (R¹, R², R³ substituted phenyl) | TR⁴ |
|---|---|---|
| II-22 | 3-OCH₃, 2-OCH₃, and O-CH₂CH₂-morpholine substituted phenyl | 3-(benzyloxy)phenyl |
| II-23 | 2,3,4-trimethoxyphenyl | 3-(pyridin-4-yloxy)phenyl |
| II-24 | 2,3,4-trimethoxyphenyl | 3-(phenylsulfonyl)phenyl |
| II-25 | 2,3,4-trimethoxyphenyl | 3-(3-nitrophenoxy)phenyl |
| II-26 | 2,3,4-trimethoxyphenyl | 3-(3-aminophenoxy)phenyl |
| II-27 | 2,3,4-trimethoxyphenyl | 3-benzylphenyl |

TABLE 3-continued

Compounds of Formula II

| No. | (R¹, R², R³ aryl) | TR⁴ |
|---|---|---|
| II-28 | 2,3-di-OCH₃, 4-OCH₃ phenyl (H₃CO, OCH₃, OCH₃) | 3-(4,6-dimethylpyrimidin-2-ylthio)phenyl |
| II-29 | 2,3-di-OCH₃, 4-OCH₃ phenyl | 4-methyl-2-phenoxypyrimidin-6-yl |
| II-30 | 2,3-di-OCH₃, 4-OCH₃ phenyl | 4-[3-methyl-5-(pyridin-2-ylthio)phenylthio]pyrimidin-2-yl |
| II-31 | 2,3-di-OCH₃, 4-OCH₃ phenyl | 2-methoxy-5-phenoxyphenyl |
| II-32 | 2,3-di-OCH₃, 4-OCH₃ phenyl | 4-(phenylamino)-1,3,5-triazin-2-yl |
| II-33 | 2,3-di-OCH₃, 4-OCH₃ phenyl | 4-(3-methoxyphenylamino)-1,3,5-triazin-2-yl |
| II-34 | 2,3-di-OCH₃, 4-OCH₃ phenyl | 4-methoxy-6-phenoxypyrimidin-2-yl |

TABLE 3-continued

Compounds of Formula II

| No. | (R¹, R², R³ on phenyl) | TR⁴ |
|---|---|---|
| II-35 | 2-OCH₃, 3-OCH₃, 4-OCH₃ phenyl | 3-(2-fluorophenyl)phenyl |
| II-36 | 2-OCH₃, 3-OCH₃, 4-OCH₃ phenyl | 3-(3-fluorophenyl)phenyl |
| II-37 | 2-OCH₃, 3-OCH₃, 4-OCH₃ phenyl | 3-(4-fluorophenyl)phenyl |
| II-38 | 2-OCH₃, 3-OCH₃, 4-OCH₃ phenyl | 3-(2-chlorophenyl)phenyl |
| II-39 | 2-OCH₃, 3-OCH₃, 4-OCH₃ phenyl | 3-(3-chlorophenyl)phenyl |
| II-40 | 2-OCH₃, 3-OCH₃, 4-OCH₃ phenyl | 3-(4-chlorophenyl)phenyl |

TABLE 3-continued

Compounds of Formula II

| No. | (aryl with R¹, R², R³) | TR⁴ |
|---|---|---|
| II-41 | R¹=OCH₃, R²=OCH₃, R³=OCH₃ | 2'-methoxy-biphenyl-3-yl |
| II-42 | R¹=OCH₃, R²=OCH₃, R³=OCH₃ | 3'-methoxy-biphenyl-3-yl |
| II-43 | R¹=OCH₃, R²=OCH₃, R³=OCH₃ | 4'-methoxy-biphenyl-3-yl |
| II-44 | R¹=OCH₃, R²=OCH₃, R³=OCH₃ | 4-methyl-4'-methoxy-biphenyl-3-yl |
| II-45 | R¹=OCH₃, R²=OCH₃, R³=OCH₃ | 4-methyl-3'-fluoro-biphenyl-3-yl |
| II-46 | R¹=OCH₃, R²=OCH₃, R³=OCH₃ | 4-methyl-3'-amino-biphenyl-3-yl |
| II-47 | R¹=OCH₃, R²=OCH₃, R³=OCH₃ | 4-methyl-3'-hydroxy-biphenyl-3-yl |

TABLE 3-continued

Compounds of Formula II

| No. | (R¹, R², R³ on phenyl) | TR⁴ |
|---|---|---|
| II-48 | 2,3,4-tri-OCH₃ phenyl | 4-methoxy-3-(pyridin-?)-phenyl (biphenyl with OCH₃ and pyridine) |
| II-49 | 2,3,4-tri-OCH₃ phenyl | 4'-(hydroxymethyl)biphenyl-3-yl |
| II-50 | 2,3,4-tri-OCH₃ phenyl | 3'-chloro-4'-fluorobiphenyl-3-yl |
| II-51 | 2,3,4-tri-OCH₃ phenyl | 3'-aminobiphenyl-3-yl |
| II-52 | 2,3,4-tri-OCH₃ phenyl | 4'-(dimethylamino)biphenyl-3-yl |
| II-53 | 2,3,4-tri-OCH₃ phenyl | 3-(pyridin-3-yl)phenyl |

TABLE 3-continued

Compounds of Formula II

| No. | ![structure with R1, R2, R3] | TR4 |
|---|---|---|
| II-54 | 2,3,4-tri(OCH3)phenyl (H3CO, OCH3, OCH3) | 4-methyl-3'-chlorobiphenyl-3-yl |
| II-55 | 2,3,4-tri(OCH3)phenyl | 4-methyl-4'-(N,N-dimethylamino)biphenyl-3-yl |
| II-56 | 2,3,4-tri(OCH3)phenyl | 1H-indazol-3-yl |
| II-57 | 2,3,4-tri(OCH3)phenyl | 4-methyl-3'-(trifluoromethyl)biphenyl-3-yl |
| II-58 | 2,3,4-tri(OCH3)phenyl | 4-methyl-2',5'-dimethylbiphenyl-3-yl |
| II-59 | 2,3,4-tri(OCH3)phenyl | 4-methyl-3'-ethoxybiphenyl-3-yl |

TABLE 3-continued

Compounds of Formula II

| No. | | TR⁴ |
|---|---|---|
| II-60 | 2,3,4-tri-OCH₃ phenyl | 4-Me-3-(pyridin-3-yl)phenyl |
| II-61 | 2,3,4-tri-OCH₃ phenyl | 4-Me-3-(hydroxymethyl)phenyl |
| II-62 | 2,3,4-tri-OCH₃ phenyl | 2'-methyl-biphenyl-3-yl |
| II-63 | 2,3,4-tri-OCH₃ phenyl | 4'-methyl-biphenyl-3-yl |
| II-64 | 2,3,4-tri-OCH₃ phenyl | 4-methoxy-3'-fluoro-biphenyl-3-yl |
| II-65 | 2,3,4-tri-OCH₃ phenyl | 4-methoxy-3'-chloro-biphenyl-3-yl |
| II-66 | 2,3,4-tri-OCH₃ phenyl | 4-fluoro-3'-chloro-biphenyl-3-yl |

TABLE 3-continued
Compounds of Formula II
| No. | | TR⁴ |
|---|---|---|
| II-67 | 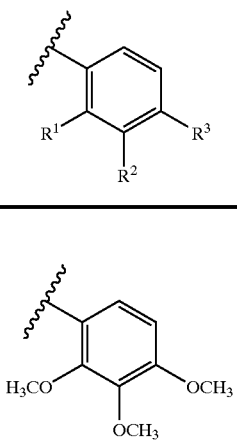 | 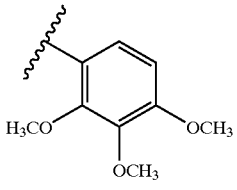 |
| II-68 | | |
| II-69 | | |
| II-70 | | 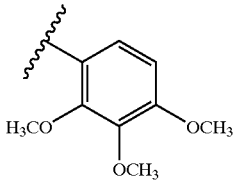 |
| II-71 | | 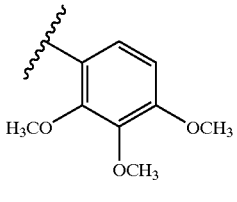 |
| II-72 | | |

TABLE 3-continued
Compounds of Formula II
| No. | 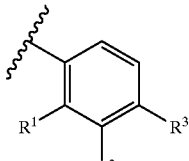 | TR⁴ |
|---|---|---|
| II-73 | 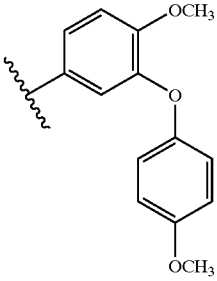 | 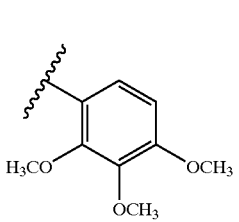 |
| II-74 | | 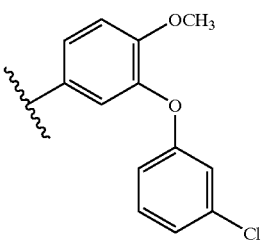 |
| II-75 | 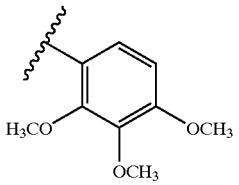 | 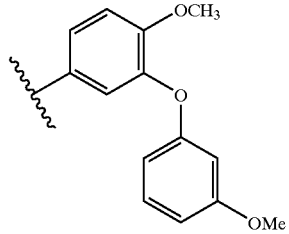 |
| II-76 | 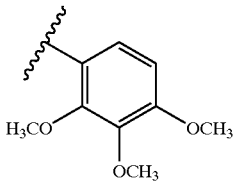 | 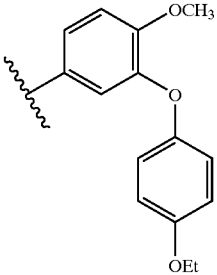 |
| II-77 | 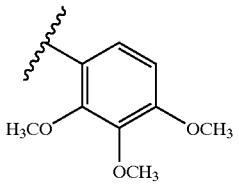 | 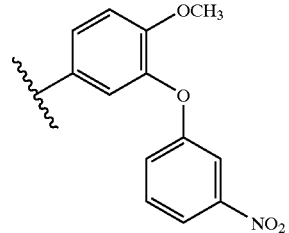 |

TABLE 3-continued
Compounds of Formula II
| No. | 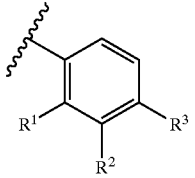 | TR⁴ |
|---|---|---|
| II-78 | 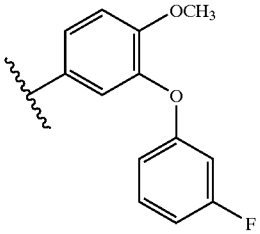 | 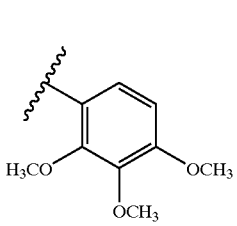 |
| II-79 | 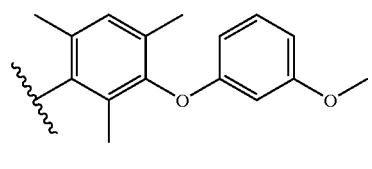 | 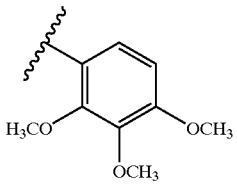 |
| II-80 | 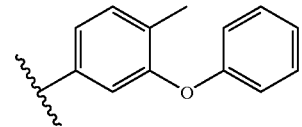 | 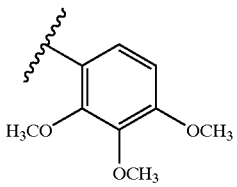 |
| II-81 | 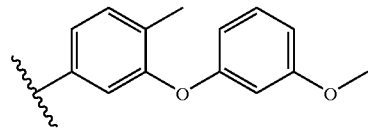 | 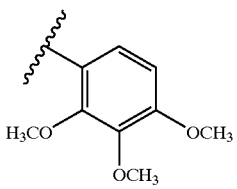 |
| II-82 | 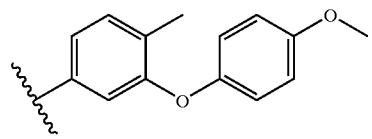 | 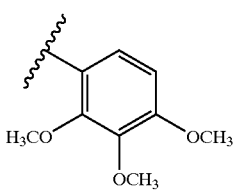 |
| II-83 | 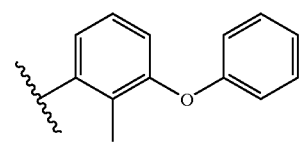 | |

TABLE 3-continued

Compounds of Formula II

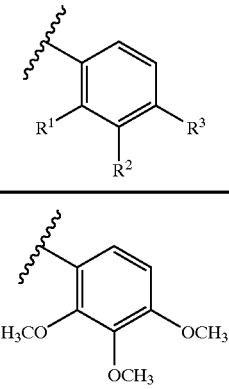

| No. | | TR⁴ |
|---|---|---|
| II-84 | | |

The present compounds may be prepared in general by methods known to those skilled in the art for analogous compounds, as illustrated by the general Schemes I through IV, and the synthetic examples shown below.

Scheme I

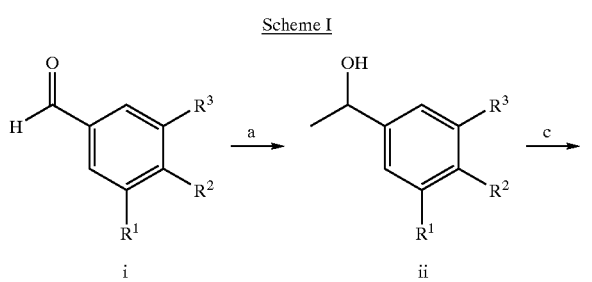

-continued

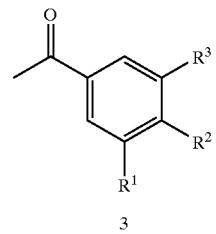

Reagents and conditions: (a) MeMgCl, THF, −78° C.; (b) MnO₂, CH₂Cl₂, reflux;

Scheme I above shows a general synthetic route used for preparing the intermediate compound 3. To a solution of aldehyde (i) in THF, at −78° C., is added a solution of methyl magnesium chloride in THF. The reaction is quenched with cold HCl (1N), then aqueous work-up followed by chromatography affords alcohol (ii).

Manganese dioxide is added to a solution of ii in CH₂Cl₂ and the resulting mixture is heated to reflux. After 3 hours, the suspension is filtered through Celite® and the filtrate concentrated in vacuo to afford ketone (3).

Scheme II

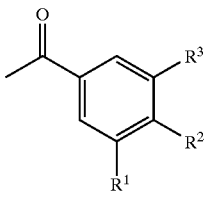

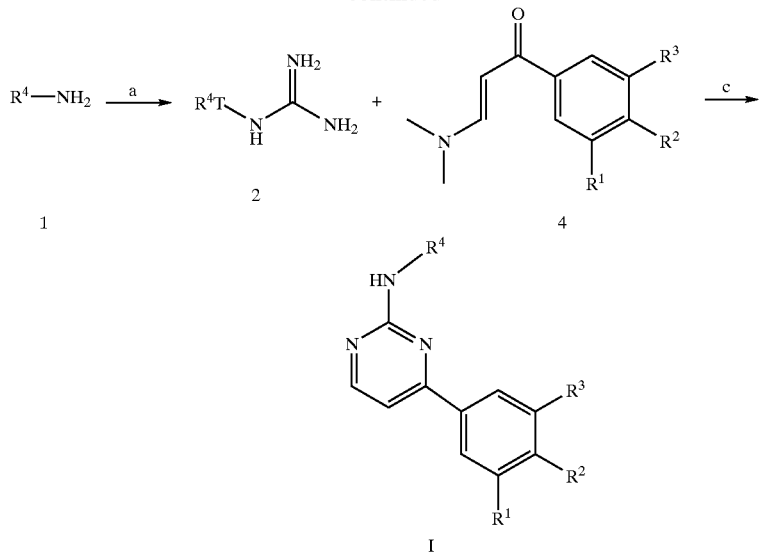

Reagents and conditions: (a) NH₂NCN, HCl, 1,4-dioxane; (b) DMF-DMa, 80° C., 12–18 hours; (c) acetonitrile, reflux.

Scheme II above shows a general synthetic route used for preparing compounds of formula I. Aniline 1 is combined with cyanamide, HCl (4N in 1,4-dioxane), and 1,4-dioxane in sealed tube and the resulting mixture heated at 60° C. After 12–18 hours, aqueous work-up affords the desired guanidine derivative (2).

Intermediate 4 is prepared from dissolving 3 in N,N-dimethylformamide dimethylacetal (DMF-DMA) and heating the resulting solution at 80° C. The reaction is concentrated in vacuo and the crude product recrystallized to afford enaminone 4.

Enaminone 4 was combined with guanidine 2 and acetonitrile and the resulting mixture heated at 80° C. After aqueous work-up, the crude product is purified by chromatography to afford I in 50–95% yield, depending upon the guanidine derivative used.

A variety of $R^1$, $R^2$, $R^3$, and $R^4$ are amenable to the reaction conditions described above for Scheme II, including those listed above in Table 1.

Scheme III

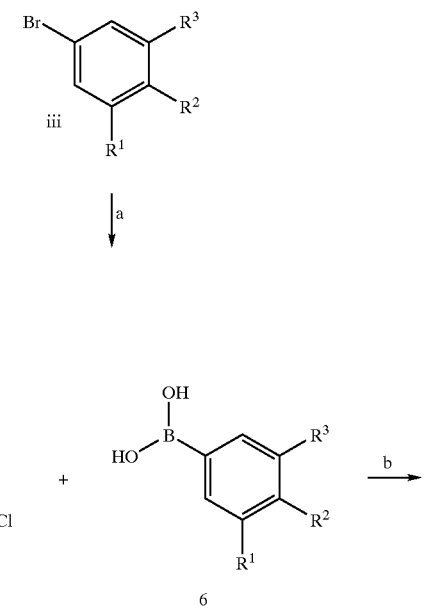

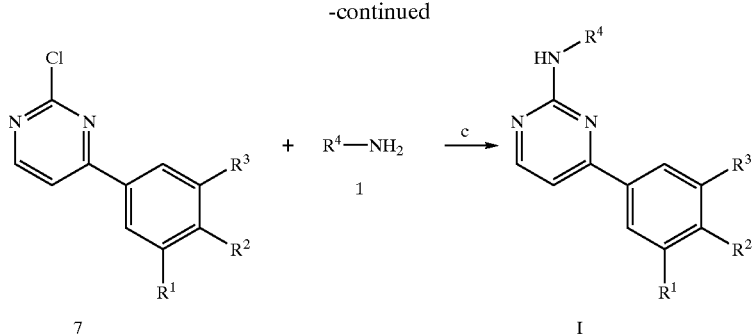

Reagents and conditions: (a) Mg, I$_2$, THF, trimethylborate; room temperature, 12–18 hours; (b) Na$_2$CO$_3$, Pd(PPh$_3$)$_4$, toluene:methanol (4:1), reflux, 24 hours;(c) NaH (60% dispersion in mineral oil), Pd(PPh$_3$)$_4$, THF, reflux, 3 hours.

Scheme III above shows an alternate method for preparing compounds of formula I. The aryl boronic acid (6) is prepared from treating the bromide iii with magnesium turnings, and a catalytic amount of iodine, in THF at reflux for 12–18 hours. The reaction is cooled to 0° C. then trimethyl borate is added and the resulting mixture stirred at room temperature for 12–18 hours. The reaction is hydrolyzed with HCl (6N, aqueous) at 60° C. then aqueous work-up afforded the desired boronic acid 6.

The boronic acid 6 is combined with the dichloropyrimidine (5), Na$_2$CO$_3$, and Pd(PPh$_3$)$_4$ in a solution of toluene:methanol (4:1). The resulting mixture is heated at reflux for 24 hours then filtered through silica gel. The crude product is purified by flash chromatography to afford chloropyrimidine 7.

The chloropyrimidine 7 is combined with the aniline 1, NaH (60% dispersion in mineral oil), and Pd(PPh$_3$)$_4$ in THF and the resulting mixture heated at reflux for 3 hours. The reaction is cooled then poured into water. Aqueous work-up, followed by flash chromatography affords I. A variety of R$^1$, R$^2$, R$^3$, and R$^4$ are amenable to the reaction conditions described above for Scheme III, including those listed above in Table 1.

Compounds of formula I wherein W is CH may also be synthesized by methods essentially similar to those described above at Scheme III, by methods shown in Scheme IV below, and by methods known to one of skill in the art.

Scheme IV

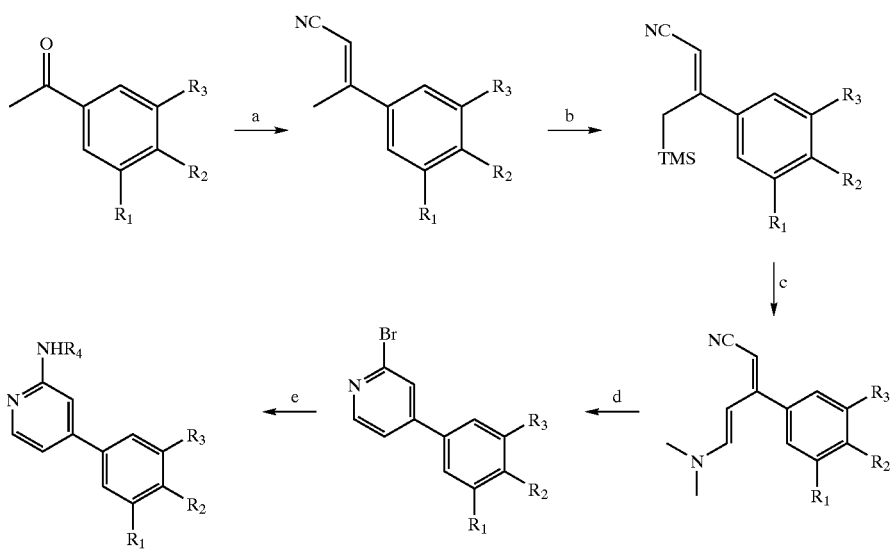

Reagents and conditions: (a) NCCH$_2$P(O)(OEt)$_2$, NaH, THF; (b) lithium hexamethyldisilazide, THF then trimethylsilyl chloride;(c) dimethylformamide dimethylacetal; (d) gaseous HBr, CHCl$_3$; e) R$^4$NH$_2$, NaH, dimethylformamide, 80° C.

The details of the conditions used for producing these compounds are set forth in the Examples. One having ordinary skill in the art may synthesize other compounds of this invention following the teachings of the specification using reagents that are readily synthesized or commercially available.

The activity of a compound utilized in this invention as an inhibitor of JNK3, GSK-3, CDK2, Lck, or Src, may be assayed in vitro, in vivo or in a cell line. In vitro assays include assays that determine inhibition of either the phosphorylation activity or ATPase activity of activated JNK3, GSK-3, CDK2, Lck, or Src. Alternate in vitro assays quantitate the ability of the inhibitor to bind to JNK3, GSK-3, CDK2, Lck, or Src. Inhibitor binding may be measured by radiolabelling the inhibitor prior to binding, isolating the inhibitor/JNK3, inhibitor/GSK-3, inhibitor/CDK2, inhibitor/Lck, or inhibitor/Src complex and determining the amount of radiolabel bound. Alternatively, inhibitor binding may be determined by running a competition experiment where new inhibitors are incubated with JNK3, GSK-3, CDK2, Lck, or Src bound to known radioligands.

According to another embodiment, the invention provides a composition comprising a compound of this invention or a pharmaceutically acceptable salt thereof and a pharmaceutically acceptable carrier, adjuvant, or vehicle. The amount of compound in the compositions of this invention is such that is effective to detectably inhibit a protein kinase, particularly JNK3, GSK-3, CDK2, Lck, or Src in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in JNK3, GSK-3, CDK2, Lck, or Src activity between a sample comprising said composition and a JNK3, GSK-3, CDK2, Lck, or Src kinase and an equivalent sample comprising JNK3, GSK-3, CDK2, Lck, or Src kinase in the absence of said composition.

A "pharmaceutically acceptable salt" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+$ $(C_{1-4}$ alkyl$)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention.

For example, chemotherapeutic agents or other antiproliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the compounds of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguamides, and insulin sensitizers; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the invention relates to a method of inhibiting JNK3, GSK-3, CDK2, Lck, or Src kinase activity in a biological sample comprising the step of contacting said biological sample with a compound of this invention, or composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of JNK3, GSK-3, CDK2, Lck, or Src kinase activity in a biological sample is useful for a variety of purposes which are known to one of skill in the art. Examples of such purposes include, but are not limited to, blood transfusion, organ-transplantation, biological specimen storage, and biological assays.

According to another embodiment, the invention provides a method for treating or lessening the severity of a JNK3-, GSK-3-, CDK2-, Lck-, or Src-mediated disease or condition in a patient comprising the step of administering to said patient a composition according to the present invention.

According to another embodiment, the present invention relates to a method of treating cancer comprising the step of blocking the transition of cancer cells into their proliferative phase by inhibiting CDK2 with a compound according to the present invention, or a pharmaceutcially acceptable composition comprising said compound.

The term "JNK-mediated disease", as used herein means any disease or other deleterious condition in which JNK is known to play a role. Such conditions include, without limitation, inflammatory diseases, autoimmune diseases, destructive bone disorders, proliferative disorders, cancer, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

Inflammatory diseases which may be treated or prevented by the compounds of this invention include, but are not limited to, acute pancreatitis, chronic pancreatitis, asthma, allergies, and adult respiratory distress syndrome.

Autoimmune diseases which may be treated or prevented by the compounds of this invention include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented by the compounds of this invention include, but are not limited to, osteoporosis, osteoarthritis and multiple myeloma-related bone disorder.

Proliferative diseases which may be treated or prevented by the compounds of this invention include, but are not limited to, acute myelogenous leukemia, chronic myelogenous leukemia, metastatic melanoma, Kaposi's sarcoma, multiple myeloma and HTLV-1 mediated tumorigenesis.

Angiogenic disorders which may be treated or prevented by the compounds of this invention include solid tumors, ocular neovasculization, infantile haemangiomas. Infectious diseases which may be treated or prevented by the compounds of this invention include, but are not limited to, sepsis, septic shock, and Shigellosis.

Viral diseases which may be treated or prevented by the compounds of this invention include, but are not limited to, acute hepatitis infection (including hepatitis A, hepatitis B and hepatitis C), HIV infection and CMV retinitis.

Neurodegenerative diseases which may be treated or prevented by the compounds of this invention include, but are not limited to, Alzheimer's disease, Parkinson's disease, amyotrophic lateral sclerosis (ALS), epilepsy, seizures, Huntington's disease, traumatic brain injury, ischemic and hemorrhaging stroke, cerebral ischemias or neurodegenerative disease, including apoptosis-driven neurodegenerative disease, caused by traumatic injury, acute hypoxia, ischemia or glutamate neurotoxicity.

"JNK-mediated diseases" also include ischemia/reperfusion in stroke, heart attacks, myocardial ischemia, organ hypoxia, vascular hyperplasia, cardiac hypertrophy, hepatic ischemia, liver disease, congestive heart failure, pathologic immune responses such as that caused by T cell activation and thrombin-induced platelet aggregation.

In addition, compounds of the instant invention may be capable of inhibiting the expression of inducible pro-inflammatory proteins. Therefore, other "JNK-mediated conditions" which may be treated by the compounds of this invention include edema, analgesia, fever and pain, such as neuromuscular pain, headache, cancer pain, dental pain and arthritis pain.

The compounds of this invention are also useful as inhibitors of Src-family kinases, especially Src and Lck. For a general review of these kinases see Thomas and Brugge, Annu. Rev. Cell Dev. Biol. (1997) 13, 513; Lawrence and Niu, Pharmacol. Ther. (1998) 77, 81; Tatosyan and Mizenina, Biochemistry (Moscow) (2000) 65, 49. The term "Src-mediated or Lck-mediated disease", as used herein means any disease or other deleterious condition in which Src or Lck is known to play a role. Accordingly, these compounds are useful for treating diseases or conditions that are known to be affected by the activity of one or more Src-family kinases. Such diseases or conditions include hypercalcemia, restenosis, osteoporosis, osteoarthritis, symptomatic treatment of bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obtructive pulmonary disorder, contact dermatitis, cancer, Paget's disease, asthma, ischemic or reperfusion injury, allergic disease, atopic dermatitis, and allergic rhinitis. Diseases that are affected by Src activity, in particular, include hypercalcemia, osteoporosis, osteoarthritis, cancer, symptomatic treatment of bone metastasis, and Paget's disease. Diseases that are affected by Lck activity, in particular, include autoimmune diseases, allergies, rheumatoid arthritis, and leukemia.

The term "GSK3-mediated disease", as used herein means any disease or other deleterious condition in which GSK3 is known to play a role. Accordingly, these compounds are useful for treating diseases or conditions that are known to be affected by the activity of GSK3 kinase. Such diseases or conditions include diabetes, Alzheimer's disease, Huntington's, Parkinson's, AIDS associated dementia, amyotrophic lateral sclerosis (AML), multiple sclerosis (MS), schizophrenia, cardiomycete hypertrophy, and baldness.

The term "CDK2-mediated disease", as used herein means any disease or other deleterious condition in which CDK2 is known to play a role. Accordingly, these compounds are useful for treating diseases or conditions that are known to be affected by the activity of CDK2 kinase. Such diseases or conditions include viral infections, neurodegenerative disorders, disorders associated with thymocyte apoptosis, or proliferative disorders resulting from the deregulation of the cell cycle, especially of the progression from $G_1$ to S phase.

A preferred embodiment relates to the method used to treat or prevent a JNK-mediated disease selected from inflammatory diseases, autoimmune diseases, destructive bone disorders, neurodegenerative diseases, allergies, reperfusion/ischemia in stroke, heart attacks, angiogenic disorders, organ hypoxia, vascular hyperplasia, cardiac hypertrophy, or thrombin-induced platelet aggregation.

Another preferred embodiment relates to the method used to treat or prevent a Src- or Lck-mediated disease selected from hypercalcemia, osteoperosis, osteoarthritis, or sympomatic treatment of bone metastasis.

Another preferred embodiment relates to the method used to treat or prevent a GSK3-mediated disease selected from diabetes, Alzheimer's disease, Huntington's disease, Parkinson's disease, multiple sclerosis (MS), or amyotrophic lateral sclerosis (AML).

According to another preferred embodiment, the method is used to treat or prevent a CDK2-mediated disease selected from viral infections, neurodegenerative disorders, or disorders associated with thymocyte apoptosis.

In addition to the compounds of this invention, pharmaceutically acceptable derivatives the compounds of this invention may also be employed in compositions to treat or prevent the above-identified disorders.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutical compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

EXAMPLES

Example 1

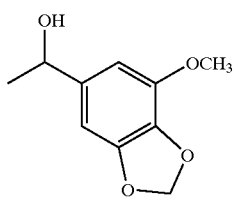

2

1-(7-Methoxy-benzo[1,3]dioxol-5-yl)-ethanol (2): A solution of 7-Methoxy-benzo[1,3]dioxole-5-carbaldehyde (I) (1.8 g, 10 mmol) in THF (20 mL) was cooled to −78° C. A solution of methylmagnesium chloride in THF (5.0 mL of 3M, 15 mmol) was added to the solution of i in THF in a dropwise fashion. The reaction was quenched by the addition of HCl (1N, aqueous) and extracted with ethyl acetate. The organic layer was washed with brine, dried over Na$_2$SO$_4$ and concentrated in vacuo. The crude product was purified by flash chromatography (silica gel; 40%–60% ethyl acetate in hexanes) to afford 2 (0.89 g, 45%).

Example 2

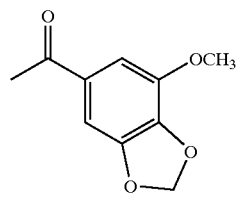

3

1-(7-Methoxy-benzo[1,3]dioxol-5-yl)-ethanone (3): Manganese dioxide (5 g, molar excess) was added to a solution of 2 (0.89 g, 4.5 mmol) in dichloromethane (10 mL). The resulting mixture was heated at reflux for 3 hours then filtered through Celite®. The filtrate was concentrated in vacuo to afford 3 as a tan solid.

Example 3

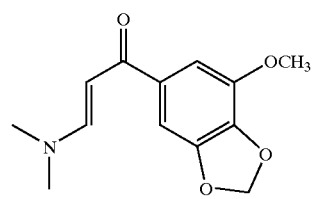

4

3-Dimthylamino-1-(7-methoxy-benzo[1,3]dioxol-5-yl)-propenone (4): A solution of 3 (0.89 g, 4.5 mmol) in N,N-dimethylformamide dimethylacetal (3.5 g, molar excess) was heated at 80° C. overnight. The reaction mixture was then concentrated in vacuo and the crude product recrystallized from ethyl acetate/hexanes to afford 4 (1.0 g, 89%).

Example 4

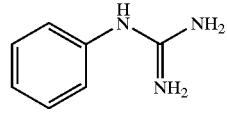

N-Phenyl-guanidine: A mixture of aniline (11 mmol), cyanamide (420 mg, 10 mmol), and HCl (3 mL of 4N in dioxane, 12 mmol) in 1,4-dioxane (10 mL) was heated in a sealed tube at 60° C. overnight. The reaction was concentrated in vacuo and the residue partitioned between NaOH (2N) and dichloromethane. The organic layer was dried over Na$_2$SO$_4$ and concentrated in vacuo to afford N-phenyl-guanidine.

Example 5

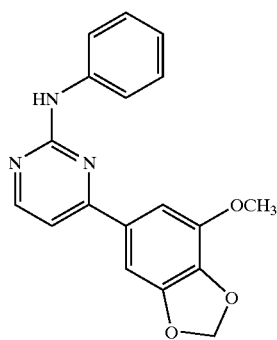

I-26

[4-(7-Methoxy-benzo[1,3]dioxol-5-yl)-pyrimidin-2-yl]-phenyl-amine (I-26): In a sealed tube, N-phenyl-guanidine (40 mg, excess) was combined with 4 (50 mg, 0.2 mmol) in acetonitrile and the mixture heated to 80° C. overnight. The reaction mixture was then partitioned between water and ethyl acetate. The organic layer was washed with brine, dried over $Na_2SO_4$ and concentrated in vacuo. The crude product was purified by flash chromatography (silica gel, 40% ethyl acetate in hexanes) to afford I-26. $^1$H-NMR (CDCl$_3$, 500 MHz) δ 8.40 (d, 1H), 7.69 (d, 2H), 7.43 (s, 1H), 7.35 (t, 2H), 7.21 (s, 1H), 7.05 (m, 2H), 6.07 (s, 2H), 3.99 (s, 3H).

Example 6

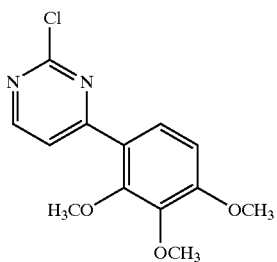

5

2-Chloro-4-(2,3,4-trimethoxyphenyl)pyrimidine (5): In a 250 mL round-bottomed flask, 1.49 grams (10 mmol) of 2,4-dichloropyrimidine was combined with 2,3,4-trimethoxyphenylboronic acid (2.12 g, 10 mmol), sodium carbonate (2.12 g, 2 equivalents), and 1.15 g (0.1 equivalents) of tetrakis-triphenylphosphinepalladium. Toluene (50 mL) and water (5 mL) were added. The reaction was allowed to reflux under nitrogen overnight. The reaction was diluted with toluene and water and the organic layer was separated, washed with brine, dried (Na$_2$SO$_4$), filtered, and concentrated to afford the crude pyrimidine 5. The compound was purified on silica gel using an eluent of 30% acetone/hexane to afford 2.08 g (74%) of the product 5 as a white solid.

Example 7

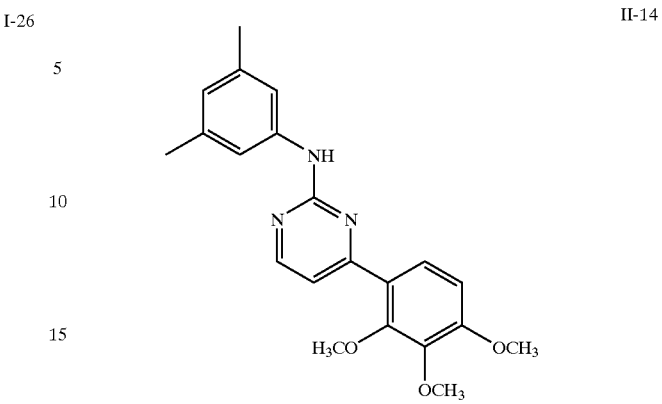

II-14

(3,5-Dimethylphenyl)-[4-(2,3,4-trimethoxyphenyl)-pyrimid-2-yl]-amine (II-14): In a vial was placed 28 mg (100 μmol) of chloropyrimidine 5, 3,5 dimethylaniline (24 mg, 200 μmol), 60% NaH (6 mg, excess), and tetrakis (triphenylphospine)palladium (6 mg, catalytic). Tetrahydrofuran (2 mL) was added and the vial was sealed and heated to reflux for two hours. The reaction was diluted with diethyl ether and washed with 1N hydrochloric acid. The organic layer was separated, washed with 1N NaOH solution, water, and brine. The organic extract was dried (MgSO$_4$), filtered, and evaporated in vacuo to afford the crude product. The compound was purified on silica gel using an eluent of 20% acetone/hexane to afford the pure product II-14 as a white solid. $^1$H-NMR (CDCl$_3$, 500 MHz) δ 8.41 (d, 1H), 7.78 (d, 1H), 7.35 (d, 1H), 7.31 (s, 1H), 7.08 (s, 1H), 6.82 (d, 1H), 6.68 (s, 1H), 3.94 (s, 3H), 3.91 (s, 3H), 3.83 (s, 3H), 2.34 (s, 6H).

Example 8

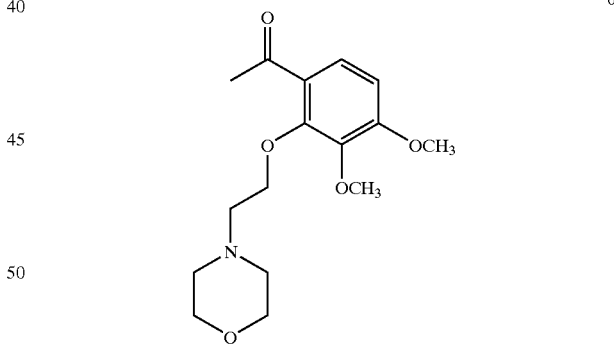

6

1-[3,4-Dimethoxy-2-(2-morpholin-4-yl-ethoxy)phenyl]-ethanone (6): In a 500 mL round-bottomed flask, 2,3-dihydroxy-4-methoxyacetophenone (3.39 grams, 17.2 mmol) was combined with 4-(2-chloroethyl)morpholine hydrochloride (3.53 grams, 19.0 mmol), 4 grams of K$_2$CO$_3$, and 50 mL of anhydrous DMF. The reaction was heated to 60° C. overnight, diluted with diethyl ether, and washed with 1N sodium hydroxide solution. The organic layer was washed with separated, washed with brine, dried (Na$_2$SO$_4$), filtered, and concentrated in vacuo. The crude product was purified by flash chromatography on silica gel using an eluent of 5% MeOH—CH$_2$Cl$_2$ to afford the pure acetophenone 6.

Example 9

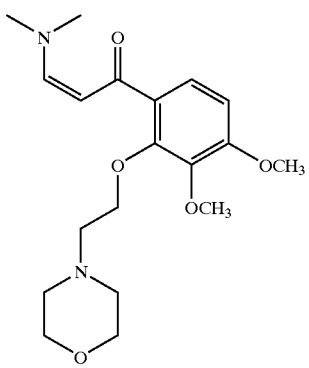

7

1-[3,4-Dimethoxy-2-(2-morpholin-4-yl-ethoxy)phenyl-3-dimethylamino-propenone (7): In a vial, 0.95 g of 6 was treated with 2 mL (excess) of dimethylformamide dimethyl acetal. The reaction was heated to 100° C. overnight. The reaction was concentrated to an oil and flash-chromatographed on a silica gel column with an eluent of 5% MeOH/CH$_2$Cl$_2$ to afford 0.57 g (51%) of the enaminone 7.

Example 10

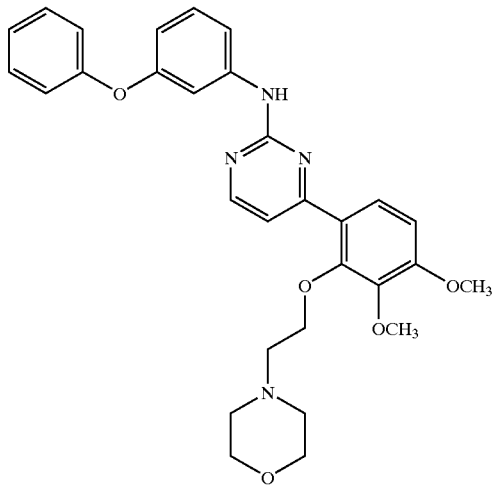

II-21

(4-[3,4-Dimethoxy-2-(2-morpholin-4-yl-ethoxy)phenyl-pyrimidin-2-yl)-(3-phenoxyphenyl)-amine (II-21): In a heavy-walled screw-top glass tube, 50 mg of the enaminone 7 was combined with 3-phenoxyguanidine and 2 mL of acetonitrile. The reaction tube was sealed and heated to 100° C. for two days. The solvent was evaporated in vacuo and the remaining material recrystallized from diethyl ether/hexane to afford pure II-21 as a white solid. $^1$H-NMR (CDCl$_3$, 500 MHz) δ 8.32 (d, 1H), 7.62 (d, 1H), 7.60 (s, 1H), 7.48 (d, 1H), 7.32–7.22 (m, 5H), 7.19 (s, 1H), 7.09–7.05 (m, 2H), 6.69–6.63 (m, 2H), 4.05 (t, 2H), 3.94 (s, 3H), 3.91 (s, 3H), 3.68 (t, 4H), 2.62 (t, 2H), 2.42 (br s, 4H).

Example 11

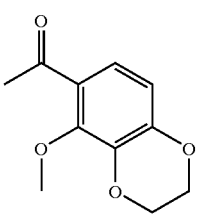

8

1-(5-Methoxy-2,3-dihydro-1,4-benzodioxin-6-yl)ethan-1-one (8): In a round-bottomed flask, 500 mg of 1-(5-Hydroxy-2,3-dihydro-1,4-benzodioxin-6-yl)ethan-1-one was dissolved in 1 mL of DMF. To this solution was added, 414 mg of K$_2$CO$_3$, and methyl iodide (1 mL, excess). The reaction was heated to 80° C. overnight. The reaction was poured into water and extracted with diethyl ether. The organic extract was washed with brine, dried (Na$_2$SO$_4$), filtered, and concentrated to afford 0.38 g (70%) of the acetophenone 8.

Example 12

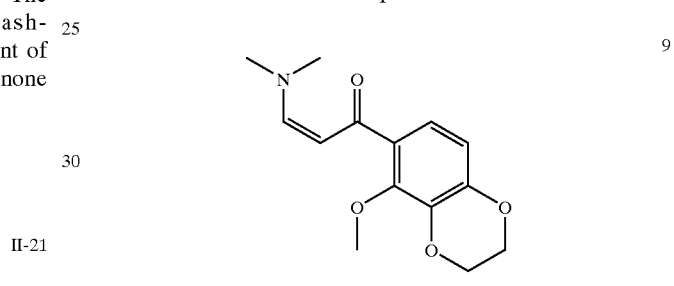

9

3-Dimethylamino-1-(5-methoxy-2,3-dihydro-benzo[1,4]dioxin-6-yl)-propenone (9): In a vial, 0.38 g (1.8 mmol) of 8 was dissolved in 1 mL of acetonitrile. Dimethylformamide dimethyl acetal (321 mg, 2.7 mmol). The vial was sealed and heated to 90° C. overnight. The reaction mixture was poured directly onto a silica gel column which was then eluted with 70% ethyl acetate/hexane. Evaporation of the appropriate fractions afforded 0.30 g (61%) of the pure enaminone 9.

Example 13

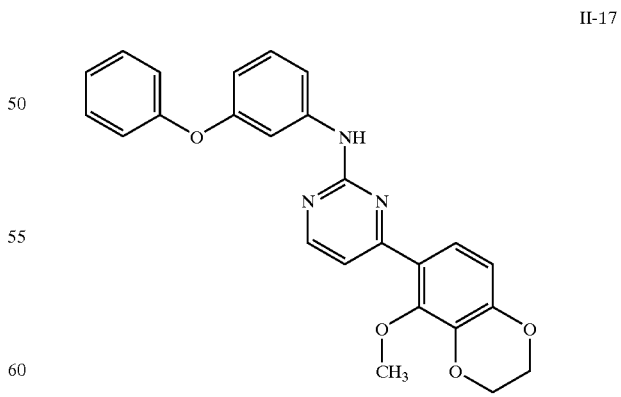

II-17

[4-(5-Methoxy-2,3-dihydro-benzo[1,4]dioxin-6-yl)-pyrimidin-2-yl]-(3-phenoxyphenyl)-amine (II-17): The enaminone 9 was dissolved in 2 mL of acetonitrile in a small vial. An excess of 3-phenoxyphenyl guanidine was added, the vial was sealed, and the mixture was heated to reflux overnight. The reaction mixture was poured directly onto a silica gel column which was then eluted with 50% ethyl acetate/hexane. The appropriate fractions were combined and evaporated in vacuo to give the crude pyrimidine II-17. The pyrimidine was recrystallized from diethyl ether/hexane to afford pure II-17. $^1$H-NMR (CDCl$_3$, 500 MHz) δ 9.78 (s, 1H), 8.45 (d, 1H), 7.75 (s, 1H), 7.48 (d, 1H), 7.35 (m, 2H), 7.23 (m, 3H), 7.08 (t, 1H), 6.96 (d, 2H), 6.62 (d, 1H), 6.52 (d, 1H), 4.30 (s, 4H), 3.70 (s, 3H).

Example 14

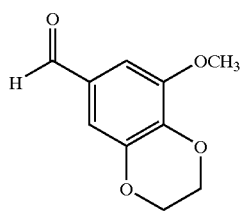

10

8-Methoxy-2,3-dihydro-benzo[1,4]dioxine-6-carbaldehyde (10): In a vial was placed 0.5 g (3.0 mmol) of 3,4-dihydroxy-5-methoxybenzaldehyde, 414 mg (3.0 mmol) of K2CO3, and 3 mL of anhydrous DMF. To this mixture was added, 0.56 g (3.0 mmol) of 1,2-dibromoethane dropwise. The vial was sealed and heated to 100° C. overnight. Water was added to the reaction and the mixture was extracted with diethyl ether. The organic extract was washed with brine, dried (Na$_2$SO$_4$), filtered, and concentrated to give the crude product. The material was purified by silica gel chromatography using 50% ethyl acetate/hexane as the eluent to afford 0.25 g (43%) of the pure aldehyde 10.

Example 15

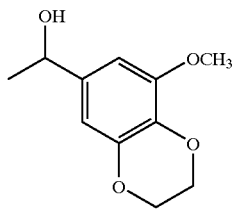

11

1-(8-Methoxy-2,3-dihydro-benzo[1,4]dioxin-6-yl)-ethanol (11): In a 250 mL round-bottomed flask, 0.60 g (3.1 mmol) of 10 was dissolved in 15 mL of anhydrous tetrahydrofuran. The solution was cooled to 0° C. and treated with 1.1 mL (3.3 mmol) of 3M methyl magnesium chloride in THF. The reaction was stirred for a few minutes then quenched with a 1N HCl solution. The mixture was extracted with ethyl acetate. The organic extract was washed with brine, dried (Na$_2$SO$_4$), filtered, and evaporated in vacuo to afford the alcohol 11.

Example 16

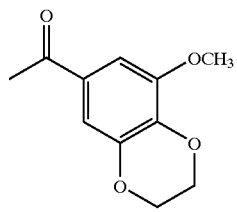

12

1-(8-methoxy-2,3-dihydro-benzo[1,4]dioxin-6-yl)-ethanone (12): In a round-bottomed flask, 0.65 g (3.1 mmol) of the alcohol 11 was dissolved in dichloromethane. To this solution was added an excess of manganese oxide. The suspension was heated to reflux overnight. The mixture was cooled and filtered through Celite. The filtrate was evaporated in vacuo to afford 0.61 g (85%) of 12 as a yellow oil.

Example 17

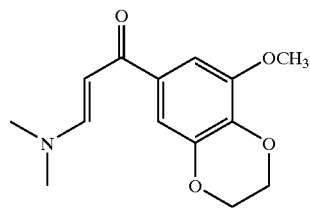

13

3-Dimethylamino-1-(8-methoxy-2,3-dihydro-benzo[1,4] dioxin-6-yl)-propenone (13): In a vial, 548 mg (2.6 mmol) of 12 was combined with 2 mL of dimethylformamide dimethyl acetal. The vial was sealed and heated to 100° C. overnight. The reaction was concentrated to dryness and the crude product was recrystallized from ethyl acetate/hexane to afford 0.5 g (73%) of the pure enaminone 13.

Example 18

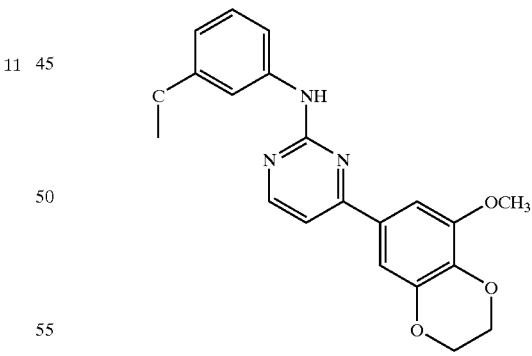

I-77

[4-(8-Methoxy-2,3-dihydro-benzo[1,4]dioxin-6-yl)-pyrimidin-2-yl]-(3-chlorophenyl)-amine (I-77): In a vial, 0.45 g (0.170 mmol) of the enaminone 13 was combined with 40 mg (excess) of 3-chlorophenyl guanidine. Acetonitrile (1 mL) was added and the mixture was heated to 100° C. overnight. The reaction was diluted with water and extracted with dichloromethane. The organic extract was dried (Na$_2$SO$_4$) and concentrated. The concentrated solution was poured directly onto a silica gel column which was eluted with 50% ethyl acetate/hexane. The appropriate fractions were combined and evaporated in vacuo to afford the pure pyrimidine I-77. $^1$H-NMR (CDCl$_3$, 500 MHz) δ 8.42 (m, 1H), 8.13 (s, 1H), 7.48 (s, 1H), 7.32–7.20 (m, 5H), 7.10 (m, 1H), 7.0 (d, 1H), 4.49 (m, 2H), 4.30 (m, 2H), 4.03 (s, 3H).

Example 19

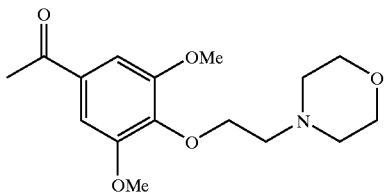

14

1-[3,5-Dimethoxy-4-(2-morpholin-4-yl-ethoxy)-phenyl]ethanone (14): In a vial, 500 mg (2.5 mmol) of 3',5'-dimethoxy-4'-hydroxyacetophenone was combined with 4-(2-chloroethyl)morpholine hydrochloride (600 mg, 3.2 mmol), and powdered potassium carbonate (1.5 g, excess). Dimethylformamide (2 mL) was added, the vial was sealed, and the rxn was heated to 80° C. overnight. The reaction was diluted with water and extracted with diethyl ether. The organic extract was washed with brine, dried (Na2SO4), and evaporated in vacuo to afford 540 mg (67%) of 14 as a white solid.

Example 20

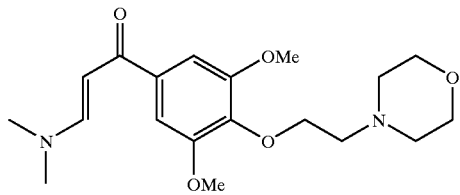

15

1-[3,5-Dimethoxy-4-(2-morpholin-4-yl-ethoxy)-phenyl]-3-dimethylamino-propenone (15): In a vial, 540 mg (1.7 mmol) of 14 was combined with 2 mL (excess) of dimethylformamide dimethylacetal. The reaction was sealed and heated to 130° C. overnight. The reaction was concentrated to dryness and the residue was triturated with diethyl ether/hexane to afford the pure enaminone 15.

Example 21

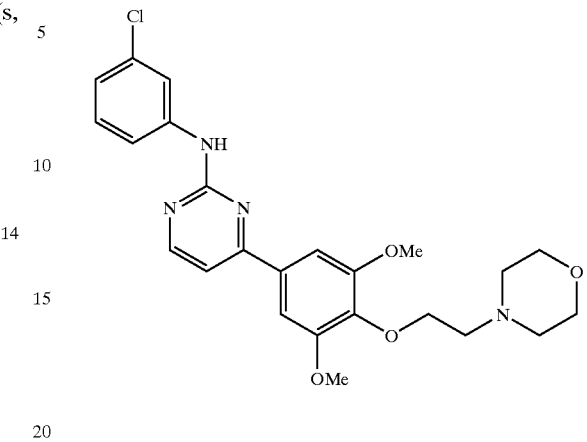

I-39

(3-Chlorophenyl)-(4[3,5-dimethoxy-4-(2-morpholin-4-yl-ethoxy)phenyl]pyrimidin-2-yl)-amine (I-39): In a vial, 60 mg of 3-chlorophenyl guanidine was combined with 40 mg of 15. Acetonitrile (0.25 mL) was added, the vial was sealed, and the reaction was heated to 80° C. for three days. The reaction was diluted with ethyl acetate and washed with brine. The organic phase was separated, dried (Na2SO4), and evaporated in vacuo. The crude product was purified by flash chromatography on silica gel using 50% ethyl acetate/methylene chloride as the eluent to afford pure I-39. $^1$H-NMR (CDCl$_3$, 500 MHz) δ 8.48 (d, 1H), 8.22 (s, 1H), 7.38 (s, 2H), 7.25–7.16 (m, 4H), 7.00 (d, 1H), 4.18 (br s, 2H), 3.98 (s, 6H), 3.77 (br s, 2H), 2.80 (br s, 2H), 2.59 (br s, 2H).

Example 22

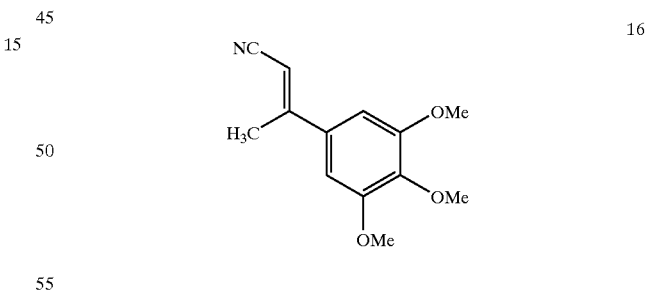

16

3-(3,4,5-Trimethoxyphenyl)-but-2-enenitrile (16): To a slurry of 60% NaH (1.46 g, 61.1 mmol) in THF at 0° C. was added 10.0 g (56.4 mmol) of ethyl(cyanomethyl) phosphate. A solution of 9.88 g (47.0 mmol) of 3,4,5-trimethoxyacetophenone in THF was added precipitating a yellow solid. The mixture was stirred at room temperature for 30 minutes, quenched with water, and extracted with ethyl acetate. The organic extract was washed with brine, dried (MgSO$_4$), and evaporated in vacuo to afford 9.32 g (85%) of 16 as a yellow oil.

Example 23

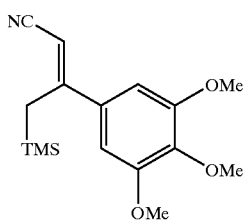

17

3-(3,4,5)-Trimethoxyphenyl)-4-(trimethylsilanyl)-but-2-enenitrile (17): To a solution of 16 (3.82 g, 16.3 mmol) in THF was added chlorotrimethylsilane (19.6 mL, 49.17 mmol). To this solution was added a solution of lithium hexamethyldisilazide in THF (24.6 mL of 1.0M, 24.6 mmol). The solution was stirred for 1 hour, quenched with water, and extracted with dichloromethane. The organic extract was dried (MgSO$_4$), and evaporated in vacuo to afford a yellow oil. The oil was purified by column chromatography on silica gel using an eluent of 10–15% ethyl acetate/hexane to afford 2.6 g (52%) of 17 as a white solid.

Example 24

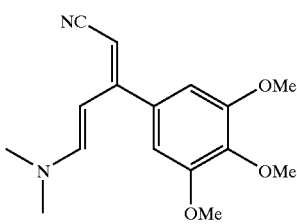

18

5-Dimethylamino-3-(3,4,5-trimethoxyphenyl)penta-2,4-dienenitrile (18): To a solution of 17 (5.8 g, 19.01 mmol) in 30 mL of toluene was added 30 mL (excess) of dimethylformamide dimethylacetal. The slurry was heated to reflux overnight. The mixture was cooled to room temperature and extracted with dichloromethane. The organic extract was washed with brine, dried (MgSO$_4$), and evaporated in vacuo to afford a yellow oil. The oil was purified using column chromatography on silica gel using an eluent of 20–30% ethyl acetate/hexane to afford 3.6 g (83%) of 18 as a yellow oil.

Example 25

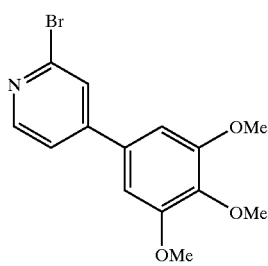

19

2-Bromo-4-(3,4,5-trimethoxyphenyl)pyridine (19): Gaseous HBr was bubbled into a solution of 18 (3.6 g, 16.1 mmol) in chloroform for 15 minutes. The reaction was diluted with dichloromethane, washed with water, washed with brine, dried (MgSO$_4$), and evaporated in vacuo to afford 3.2 g (62%) of 19 as an off-white solid.

Example 26

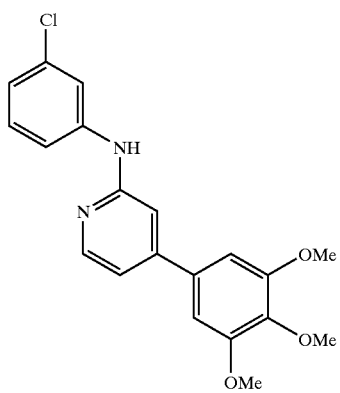

I-146

(3-Chlorophenyl)-[4-(3,4,5-trimethoxyphenyl)-pyridin-2-yl]-amine (I-146): To a solution of 19 (50 mg) in 3 mL of DMF was added 2 equivalents of aniline, 2 equivalents of NaH and Pd(PPh3)4. The mixture was heated to 80° C. overnight, cooled, poured into water, and extracted with ethyl acetate. The organic extract was washed with brine, dried (Na$_2$SO$_4$), and evaporated in vacuo to afford an brown oil. The oil was purified by prep HPLC to afford pure I-146. Expected Mass=7370.1084; Found Mass (M+1)=371.0. Retention time=3.25 minutes.

We have prepared other compounds of formula I by methods substantially similar to those described in the above Examples 1–26 and those illustrated in Schemes I–IV. The characterization data for these compounds is summarized in Table 4 below and includes LC/MS (observed), HPLC, and $^1$H NMR data.

As used herein in Table 4 below, "Y" designates the indicated data is available and was found to be consistent with structure. Compound numbers correspond to the compound numbers listed in Tables 1, 2, and 3.

The term "R$_t$" refers to the retention time, in minutes, associated with the compound.

TABLE 4

Characterization Data for Selected Compounds

| Compound No | M + 1 (obs) | $^1$H NMR | R$_t$ |
|---|---|---|---|
| I-26 | — | Y | — |
| I-27 | — | Y | — |
| I-28 | — | Y | — |
| I-29 | — | Y | — |
| I-30 | — | Y | — |
| I-31 | — | Y | — |
| I-32 | — | Y | — |
| I-33 | — | Y | — |
| I-39 | — | Y | — |
| I-39 | Y | Y | Y |
| I-40 | Y | Y | Y |
| I-41 | Y | Y | Y |
| I-42 | Y | Y | Y |
| I-43 | Y | Y | Y |
| I-44 | Y | Y | Y |
| I-45 | Y | Y | Y |
| I-46 | Y | Y | Y |
| I-47 | Y | Y | Y |
| I-48 | Y | Y | Y |
| I-49 | Y | Y | Y |
| I-50 | Y | Y | Y |
| I-51 | Y | Y | Y |
| I-52 | Y | Y | Y |
| I-53 | Y | Y | Y |

TABLE 4-continued

Characterization Data for Selected Compounds

| Compound No | M + 1 (obs) | ¹H NMR | R$_t$ |
|---|---|---|---|
| I-54 | Y | Y | Y |
| I-55 | Y | Y | Y |
| I-56 | Y | — | Y |
| I-57 | Y | — | Y |
| I-58 | Y | — | Y |
| I-59 | Y | — | Y |
| I-60 | Y | — | Y |
| I-61 | Y | — | Y |
| I-62 | Y | — | Y |
| I-63 | Y | — | Y |
| I-64 | Y | — | Y |
| I-65 | Y | — | Y |
| I-66 | Y | — | Y |
| I-67 | Y | — | Y |
| I-68 | Y | — | Y |
| I-69 | Y | — | Y |
| I-70 | Y | — | Y |
| I-71 | Y | — | Y |
| I-72 | Y | — | Y |
| I-73 | Y | — | Y |
| I-74 | Y | Y | Y |
| I-75 | Y | Y | Y |
| I-76 | Y | Y | Y |
| I-77 | Y | Y | Y |
| I-78 | Y | Y | Y |
| I-79 | Y | Y | Y |
| I-80 | Y | Y | Y |
| I-81 | Y | Y | Y |
| I-82 | Y | Y | Y |
| I-83 | Y | Y | Y |
| I-84 | Y | Y | Y |
| I-85 | Y | Y | Y |
| I-86 | Y | Y | Y |
| I-87 | Y | Y | Y |
| I-88 | Y | Y | Y |
| I-89 | Y | Y | Y |
| I-144 | Y | — | Y |
| I-145 | Y | — | Y |
| I-146 | Y | — | Y |
| I-147 | Y | — | Y |
| I-148 | Y | — | Y |
| I-149 | Y | — | Y |
| I-150 | Y | — | Y |
| I-151 | Y | — | Y |
| I-152 | Y | — | Y |
| I-153 | Y | — | Y |
| I-154 | Y | — | Y |
| I-155 | Y | — | Y |
| I-156 | Y | — | Y |
| I-157 | Y | — | Y |
| I-158 | Y | — | Y |
| I-159 | Y | — | Y |
| I-160 | Y | — | Y |
| II-1 | — | — | Y |
| II-2 | — | — | Y |
| II-3 | — | — | Y |
| II-4 | — | — | Y |
| II-5 | — | — | Y |
| II-6 | — | — | Y |
| II-7 | — | — | Y |
| II-8 | — | — | Y |
| II-9 | — | — | Y |
| II-10 | — | — | Y |
| II-11 | — | — | Y |
| II-12 | — | — | Y |
| II-13 | — | — | Y |
| II-14 | Y | Y | Y |
| II-15 | Y | Y | Y |
| II-16 | Y | Y | Y |
| II-17 | Y | Y | Y |
| II-18 | Y | Y | Y |
| II-19 | Y | Y | Y |
| II-20 | Y | Y | Y |
| II-21 | Y | Y | Y |
| II-22 | Y | Y | Y |
| II-23 | Y | — | Y |
| II-24 | Y | — | Y |
| II-25 | Y | — | Y |
| II-44 | Y | — | Y |
| II-45 | Y | — | Y |
| II-46 | Y | — | Y |
| II-47 | Y | — | Y |
| II-48 | Y | — | Y |
| II-49 | Y | — | Y |
| II-50 | Y | — | Y |
| II-51 | Y | — | Y |
| II-52 | Y | — | Y |
| II-53 | Y | — | Y |
| II-54 | Y | — | Y |
| II-55 | Y | — | Y |
| II-57 | Y | — | Y |
| II-58 | Y | — | Y |
| II-59 | Y | — | Y |
| II-60 | Y | — | Y |
| II-61 | Y | — | Y |
| II-64 | Y | — | Y |
| II-65 | Y | — | Y |
| II-66 | Y | — | Y |
| II-67 | Y | — | Y |
| II-68 | Y | — | Y |
| II-69 | Y | — | Y |

The following examples demonstrate how the compounds of this invention may be tested as inhibitors of JNK3, Src, Lck, GSK3, and CDK2 kinases.

Example 27

Cloning, Expression and Purification of JNK3 Protein

A BLAST search of the EST database using the published JNK3α1 cDNA as a query identified an EST clone (#632588) that contained the entire coding sequence for human JNK3α1. Polymerase chain reactions (PCR) using pfu polymerase (Strategene) were used to introduce restriction sites into the cDNA for cloning into the pET-15B expression vector at the NcoI and BamHI sites. The protein was expressed in *E. coli*. Due to the poor solubility of the expressed full-length protein (Met 1-Gln 422), an N-terminally truncated protein starting at Ser residue at position 40 (Ser 40) was produced. This truncation corresponds to Ser 2 of JNK1 and JNK2 proteins, and is preceded by a methionine (initiation) and a glycine residue. The glycine residue was added in order to introduce an NcoI site for cloning into the expression vector. In addition, systematic C-terminal truncations were performed by PCR to identify a construct that give rise to diffraction-quality crystals. One such construct encodes amino acid residues Ser40-Glu402 of JNK3α1 and is preceded by Met and Gly residues.

The construct was prepared by PCR using deoxyoligonucleotides:
5' GCTCTAGAGCTCC ATGGGCAGCAAAAGCAAAGTTGACAA 3' (forward primer with initiation codon underlined)(SEQ ID NO:1) and
5' TAGCGGATCC TCATTCTGAATTCATTACTTCCTTGTA 3' (reverse primer with stop codon underlined)(SEQ ID NO:2) as primers and was confirmed by DNA sequencing. Control experiments indicated that the truncated JNK3 protein had an equivalent kinase activity towards myelin basic protein when activated with an upstream kinase MKK7 in vitro.

E. coli strain BL21 (DE3) (Novagen) was transformed with the JNK3 expression construct and grown at 30° C. in LB supplemented with 100 µg/ml carbenicillin in shaker flasks until the cells were in log phase (OD$_{600}$~0.8). Isopropylthio-β-D-galactosidase (IPTG) was added to a final concentration of 0.8 mM and the cells were harvested 2 hours later by centrifugation.

E. coli cell paste containing JNK3 was resuspended in 10 volumes/g lysis buffer (50 mM HEPES, pH 7.2, containing 10% glycerol (v/v), 100 mM NaCl, 2 mM DTT, 0.1 mM PMSF, 2 µg/ml Pepstatin, 1 µg/ml each of E-64 and Leupeptin). Cells were lysed on ice using a microfluidizer and centrifuged at 100,000×g for 30 min at 4° C. The 100,000×g supernatant was diluted 1:5 with Buffer A (20 mM HEPES, pH 7.0, 10% glycerol (v/v), 2 mM DTT) and purified by SP-Sepharose (Pharmacia) cation-exchange chromatography (column dimensions: 2.6×20 cm) at 4° C. The resin was washed with 5 column volumes of Buffer A, followed by 5 column volumes of Buffer A containing 50 mM NaCl. Bound JNK3 was eluted with a 7.5 column volume linear gradient of 50–300 mM NaCl. JNK3 eluted between 150–200 mM NaCl.

Example 28

Activation of JNK3

5 mg of JNK3 was diluted to 0.5 mg/ml in 50 mM HEPES buffer, pH 7.5, containing 100 mM NaCl, 5 mM DTT, 20 mM MgCl$_2$, and 1 mM ATP. GST-MKK7(DD) was added at a molar ratio of 1:2.5 GST-MKK7:JNK3. After incubation for 30 minutes at 25° C., the reaction mixture was concentrated 5-fold by ultrafiltration in a Centriprep-30 (Amicon, Beverly, Mass.), diluted to 10 ml and an additional 1 mM ATP added. This procedure was repeated three times to remove ADP and replenish ATP. The final addition of ATP was 5 mM and the mixture incubated overnight at 4° C.

The activated JNK3/GST-MKK7(DD) reaction mixture was exchanged into 50 mM HEPES buffer, pH 7.5, containing 5 mM DTT and 5% glycerol (w/v) by dialysis or ultrafiltration. The reaction mixture was adjusted to 1.1 M potassium phosphate, pH 7.5, and purified by hydrophobic interaction chromatography (at 25° C.) using a Rainin Hydropore column. GST-MKK7 and unactivated JNK3 do not bind under these conditions such that when a 1.1 to 0.05 M potassium phosphate gradient is developed over 60 minutes at a flow rate of 1 ml/minute, doubly phosphorylated JNK3 is separated from singly phosphorylated JNK. Activated JNK3 (i.e. doubly phosphorylated JNK3) was stored at −70° C. at 0.25–1 mg/ml.

Example 29

JNK Inhibition Assay

Compounds were assayed for the inhibition of JNK3 by a spectrophotometric coupled-enzyme assay. In this assay, a fixed concentration of activated JNK3 (10 nM) was incubated with various concentrations of a potential inhibitor dissolved in DMSO for 10 minutes at 30° C. in a buffer containing 0.1 M HEPES buffer, pH 7.5, containing 10 mM MgCl$_2$, 2.5 mM phosphoenolpyruvate, 200 µM NADH, 150 µg/mL pyruvate kinase, 50 µg/mL lactate dehydrogenase, and 200 µM EGF receptor peptide. The EGF receptor peptide has the sequence KRELVEPLTPSGEAPNQALLR, and is a phosphoryl acceptor in the JNK3-catalyzed kinase reaction. The reaction was initiated by the addition of 10 µM ATP and the assay plate is inserted into the spectrophotometer's assay plate compartment that was maintained at 30° C. The decrease of absorbance at 340 nm was monitored as a function of time. The rate data as a function of inhibitor concentration was fitted to competitive inhibition kinetic model to determine the $K_i$.

Table 5 shows the results of the activity of selected compounds of this invention in the JNK inhibition assay. The compound numbers correspond to the compound numbers in Tables 1, 2, and 3. Compounds having a $K_i$ less than 0.1 micromolar (µM) are rated "A", compounds having a $K_i$ between 0.1 and 1 µM are rated "B" and compounds having a $K_i$ greater than 1 µM are rated "C". Activity ratings "D", "E", and "F" correspond to percent inhibition at a 2 µM inhibitor concentration. Compounds having an activity designated as "D" provided a percent inhibition less than or equal to 33%; compounds having an activity designated as "E" provided a percent inhibition of between 24% and 66%; and compounds having an activity designated as "F" provided a provided a percent inhibition of between 67% and 100%.

TABLE 5

Activity in the JNK3 Inhibition Assay.

| No. | Activity | No. | Activity | No. | Activity |
|---|---|---|---|---|---|
| I-1 | B | I-2 | B | I-3 | A |
| I-4 | B | I-5 | B | I-6 | A |
| I-7 | B | I-8 | C | I-9 | A |
| I-10 | B | I-11 | A | I-12 | A |
| I-13 | A | I-14 | C | I-15 | A |
| I-16 | A | I-17 | A | I-18 | A |
| I-19 | A | I-20 | A | I-21 | A |
| I-22 | A | I-23 | A | I-24 | B |
| I-25 | A | I-26 | B | I-27 | C |
| I-28 | B | I-29 | B | I-30 | C |
| I-31 | C | I-32 | B | I-33 | B |
| I-34 | A | I-35 | A | I-36 | A |
| I-37 | C | I-38 | A | I-39 | A |
| I-40 | A | I-41 | B | I-42 | A |
| I-43 | B | I-44 | A | I-45 | A |
| I-46 | B | I-47 | A | I-48 | B |
| I-49 | A | I-50 | A | I-51 | A |
| I-52 | A | I-53 | A | I-54 | A |
| I-55 | A | I-56 | C | I-57 | A |
| I-58 | A | I-59 | A | I-60 | A |
| I-61 | A | I-62 | A | I-63 | A |
| I-64 | F | I-65 | D | I-66 | A |
| I-67 | D | I-68 | E | I-69 | D |
| I-70 | E | I-71 | D | I-72 | E |
| I-73 | A | I-74 | A | I-75 | A |
| I-76 | A | I-77 | A | I-78 | A |
| I-79 | A | I-80 | A | I-81 | A |
| I-82 | A | I-83 | C | I-84 | C |
| I-85 | B | I-86 | C | I-87 | B |
| I-88 | B | I-89 | B | I-94 | A |
| I-146 | B | I-147 | B | I-151 | B |
| I-154 | B | I-155 | B | II-32 | A |
| II-33 | C | — | — | — | — |

Example 30

Src Inhibition Assay

The compounds were assayed as inhibitors of full length recombinant human Src kinase (from Upstate Biotechnology, cat. no. 14-117) expressed and purified from baculo viral cells. Src kinase activity was monitored by following the incorporation of $^{33}$P from ATP into the tyrosine of a random poly Glu-Tyr polymer substrate of composition, Glu:Tyr=4:1 (Sigma, cat. no. P-0275). The following were the final concentrations of the assay components: 0.05 M HEPES, pH 7.6, 10 mM $MgCl_2$, 2 mM DTT, 0.25 mg/ml BSA, 10 μM ATP (1–2 μCi $^{33}$P-ATP per reaction), 5 mg/ml poly Glu-Tyr, and 1–2 units of recombinant human Src kinase. In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 min before initiating the reaction with $^{33}$P-ATP. After 20 min of reaction, the reactions were quenched with 150 μl of 10% trichloroacetic acid (TCA) containing 20 mM $Na_3PO_4$. The quenched samples were then transferred to a 96-well filter plate (Whatman, UNI-Filter GF/F Glass Fiber Filter, cat no. 7700-3310) installed on a filter plate vacuum manifold. Filter plates were washed four times with 10% TCA containing 20 mM $Na_3PO_4$ and then 4 times with methanol. 200 μl of scintillation fluid was then added to each well. The plates were sealed and the amount of radioactivity associated with the filters was quantified on a TopCount scintillation counter.

Table 6 shows the results of the activity of selected compounds of this invention in the SRC inhibition assay. The compound numbers correspond to the compound numbers in Tables 1, 2, and 3. Compounds having a $K_i$ less than 0.1 micromolar (μM) are rated "A", compounds having a $K_i$ between 0.1 and 1 μM are rated "B" and compounds having a $K_i$ greater than 1 μM are rated "C". Activity ratings "D", "E", and "F" correspond to percent inhibition at a 2 μM inhibitor concentration. Compounds having an activity designated as "D" provided a percent inhibition less than or equal to 33%; compounds having an activity designated as "E" provided a percent inhibition of between 24% and 66%; and compounds having an activity designated as "F" provided a provided a percent inhibition of between 67% and 100%.

TABLE 6

Activity in the SRC Inhibition Assay.

| No. | Activity | No. | Activity | No. | Activity |
|---|---|---|---|---|---|
| I-1 | C | I-3 | D | I-4 | C |
| I-12 | D | I-13 | E | I-34 | C |
| I-48 | E | I-50 | F | I-57 | E |
| I-58 | E | I-59 | F | I-60 | F |
| I-61 | D | I-62 | D | I-63 | E |
| I-64 | F | I-67 | D | I-68 | D |
| I-69 | D | I-70 | D | I-71 | D |
| I-72 | D | I-73 | E | I-74 | E |
| I-75 | F | I-76 | E | I-77 | F |
| I-78 | E | I-79 | E | I-80 | E |
| I-81 | F | I-82 | D | II-1 | A |
| II-24 | A | II-62 | B | II-63 | A |
| II-64 | A | II-65 | B | II-66 | C |
| II-67 | A | II-68 | B | II-69 | A |

Example 31

Lck Inhibition Assay

The compounds were assayed as inhibitors of Lck kinase purified from bovine thymus (from Upstate Biotechnology, cat. no. 14-106). Lck kinase activity was monitored by following the incorporation of $^{33}$P from ATP into the tyrosine of a random poly Glu-Tyr polymer substrate of composition, Glu:Tyr=4:1 (Sigma, cat. no. P-0275). The following were the final concentrations of the assay components: 0.05 M HEPES, pH 7.6, 10 mM $MgCl_2$, 2 mM DTT, 0.25 mg/ml BSA, 10 μM ATP (1–2 μCi $^{33}$P-ATP per reaction), 5 mg/ml poly Glu-Tyr, and 1–2 units of lck kinase. In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 min before initiating the reaction with $^{33}$P-ATP. After 20 min of reaction, the reactions were quenched with 150 μl of 10% trichloroacetic acid (TCA) containing 20 mM Na3PO4. The quenched samples were then transferred to a 96-well filter plate (Whatman, UNI-Filter GF/F Glass Fiber Filter, cat no. 7700-3310) installed on a filter plate vacuum manifold. Filter plates were washed four times with 10% TCA containing 20 mM $Na_3PO_4$ and then 4 times with methanol. 200 μl of scintillation fluid was then added to each well. The plates were sealed and the amount of radioactivity associated with the filters was quantified on a TopCount scintillation counter.

Table 7 shows the results of the activity of selected compounds of this invention in the Lck inhibition assay. The compound numbers correspond to the compound numbers in Tables 1, 2, and 3. Compounds having a $K_i$ less than 0.1 micromolar (μM) are rated "A", compounds having a $K_i$ between 0.1 and 1 μM are rated "B" and compounds having a $K_i$ greater than 1 μM are rated "C". Activity ratings "D", "E", and "F" correspond to percent inhibition at a 5 μM inhibitor concentration. Compounds having an activity designated as "D" provided a percent inhibition less than or equal to 33%; compounds having an activity designated as "E" provided a percent inhibition of between 24% and 66%; and compounds having an activity designated as "F" provided a provided a percent inhibition of between 67% and 100%.

TABLE 7

Activity in the Lck Inhibition Assay.

| No. | Activity | No. | Activity | No. | Activity |
|---|---|---|---|---|---|
| I-3 | C | I-34 | C | I-57 | B |
| I-66 | E | I-68 | D | I-85 | B |
| I-89 | B | I-94 | B | — | — |
| II-1 | A | II-2 | B | II-3 | D |
| II-4 | B | II-5 | C | II-6 | B |
| II-7 | E | II-8 | E | II-9 | D |
| II-10 | C | II-11 | E | II-12 | B |
| II-14 | F | II-15 | B | II-16 | B |
| II-17 | C | II-18 | C | II-19 | C |
| II-20 | C | II-21 | C | II-22 | C |
| II-23 | A | II-24 | B | II-25 | A |
| II-26 | A | II-27 | B | II-31 | A |
| II-32 | C | II-33 | C | II-34 | C |
| II-35 | A | II-36 | A | II-37 | A |
| II-38 | B | II-39 | A | II-40 | A |
| II-41 | B | II-42 | B | II-43 | A |
| II-44 | B | II-45 | B | II-46 | B |
| II-47 | B | II-48 | B | II-49 | A |
| II-50 | B | II-51 | B | II-52 | B |
| II-53 | B | II-54 | B | II-55 | A |
| II-57 | C | II-58 | C | II-59 | B |
| II-60 | B | II-61 | B | II-62 | C |
| II-63 | B | II-70 | B | II-71 | B |
| II-72 | C | II-73 | A | II-74 | A |
| II-75 | A | II-76 | A | — | — |

Example 32

GSK-3 Inhibition Assay

Compounds were screened in the following manner for their ability to inhibit Glycogen Synthase Kinase 3 (GSK-3)

using a standard coupled enzyme assay (Fox et al (1998) *Protein Sci* 7, 2249). To an assay stock buffer solution containing 0.1M HEPES 7.5, 10 mM $MgCl_2$, 25 mM NaCl, 2.5 mM phosphoenolpyruvate, 300 μM NADH, 1 mM DTT, 30 μg/mL pyruvate kinase, 10 μg/mL lactate dehydrogenase, 300 μM peptide (HSSPHQp-SEDEEE, American Peptide, Sunnyvale, Calif.), and 60 nM GSK-3, was added a 30 μM solution of the compound in DMSO and the resulting mixture incubated at 30° C. for 5 min. The reaction was initiated by the addition of 10 μM ATP. The rates of reaction were obtained by monitoring absorbance at 340 nM over a 5 minute read time at 30° C. using a Molecular Devices plate reader (Sunnyvale, Calif.). The $IC_{50}$ was determined from the rate data as a function of inhibitor concentration.

Table 8 shows the results of the activity of selected compounds of this invention in the GSK-3 inhibition assay. The compound numbers correspond to the compound numbers in Tables 1, 2, and 3. Compounds having a $K_i$ less than 0.1 micromolar (μM) are rated "A", compounds having a $K_i$ between 0.1 and 1 μM are rated "B" and compounds having a $K_i$ greater than 1 μM are rated "C".

TABLE 8

GSK-3 Inhibitory Activity of Selected Compounds

| No. | Activity | No. | Activity | No. | Activity |
|---|---|---|---|---|---|
| I-1 | C | I-3 | F | I-4 | C |
| I-5 | C | I-9 | B | I-10 | B |
| I-12 | B | I-18 | A | I-20 | B |
| I-22 | C | I-34 | B | I-35 | A |
| I-37 | C | I-38 | A | I-39 | B |
| I-41 | B | I-42 | C | I-43 | B |
| I-48 | B | I-49 | B | I-50 | E |
| I-51 | B | I-52 | B | I-57 | B |
| I-59 | A | I-62 | B | I-64 | B |
| I-65 | A | I-66 | A | I-68 | E |
| I-75 | A | I-83 | C | I-87 | C |
| I-88 | C | I-158 | C | I-159 | B |
| I-160 | C | II-18 | C | II-25 | A |
| II-26 | A | II-32 | B | II-33 | C |
| II-44 | C | II-45 | C | II-46 | C |
| II-47 | B | II-48 | B | II-64 | C |
| II-65 | C | II-66 | C | II-67 | A |
| II-68 | A | II-69 | A | II-70 | B |
| II-71 | C | II-72 | C | II-73 | A |
| II-74 | A | II-75 | A | II-76 | B |

Example 33

CDK2 Inhibition Assay

Compounds were screened in the following manner for their ability to inhibit CDK2 using a standard coupled enzyme assay (Fox et al (1998) *Protein Sci* 7, 2249).

To an assay stock buffer solution containing 0.1M HEPES 7.5, 10 mM $MgCl_2$, 1 mM DTT, 25 mM NaCl, 2.5 mM phosphoenolpyruvate, 300 mM NADH, 30 mg/ml pyruvate kinase, 10 mg/ml lactate dehydrogenase, 100 mM ATP, and 100 μM peptide (MAHHHRSPRKRAKKK, American Peptide, Sunnyvale, Calif.) was added a DMSO solution of a compound of the present invention to a final concentration of 30 μM. The resulting mixture was incubated at 30° C. for 10 minutes.

The reaction was initiated by the addition of 10 μL of CDK-2/Cyclin A stock solution to give a final concentration of 25 nM in the assay. The rates of reaction were obtained by monitoring absorbance at 340 nm over a 5-minute read time at 30° C. using a BioRad Ultramark plate reader (Hercules, Calif.). The $K_i$ values were determined from the rate data as a function of inhibitor concentration.

Table 9 shows the results of the activity of selected compounds of this invention in the CDK2 inhibition assay. The compound numbers correspond to the compound numbers in Tables 1, 2, and 3. Compounds having a $K_i$ less than 2 micromolar (μM) are rated "A", compounds having a $K_i$ between 2 and 5 μM are rated "B" and compounds having a $K_i$ greater than 5 μM are rated "C".

TABLE 9

CDK2 Inhibitory Activity of Selected Compounds

| No. | Activity | No. | Activity | No. | Activity |
|---|---|---|---|---|---|
| I-1 | C | I-2 | C | I-3 | C |
| I-4 | C | I-5 | C | I-6 | C |
| I-7 | C | I-8 | C | I-9 | C |
| I-10 | C | I-11 | C | I-12 | C |
| I-13 | C | I-15 | C | I-16 | C |
| I-18 | C | I-19 | C | I-20 | C |
| 1-21 | C | I-22 | C | I-23 | C |
| I-24 | C | I-26 | C | I-32 | C |
| I-33 | C | I-34 | C | I-35 | C |
| I-36 | C | I-38 | C | I-39 | C |
| I-40 | C | I-41 | C | I-42 | C |
| I-43 | C | I-44 | C | I-45 | C |
| I-46 | C | I-49 | C | I-51 | C |
| I-53 | C | I-54 | C | I-55 | C |
| I-56 | C | I-57 | C | I-59 | C |
| I-60 | C | I-61 | C | I-65 | C |
| I-66 | A | I-68 | E | II-44 | C |
| II-45 | C | II-46 | C | II-47 | C |
| II-48 | C | II-49 | C | II-50 | C |
| II-51 | C | II-52 | C | II-53 | C |
| II-54 | C | II-55 | C | II-56 | C |
| II-57 | C | II-58 | C | II-59 | C |
| II-60 | C | II-61 | C | II-62 | C |
| II-70 | C | II-71 | C | II-72 | C |
| II-73 | C | II-74 | C | II-75 | C |
| II-76 | C | | | | |

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

We claim:

1. A compound of formula I or II:

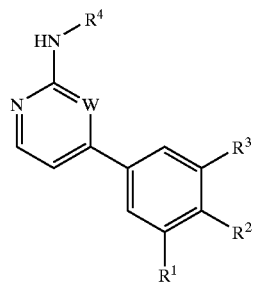

I

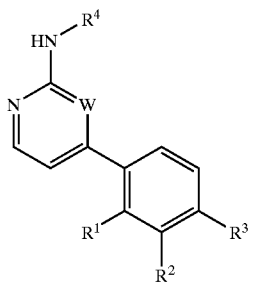

II or a pharmaceutically acceptable salt thereof, wherein:
each W is nitrogen;
each $R^1$, $R^2$, and $R^3$ is independently selected from halogen, QR, $Q_{(n)}$CN, $Q_{(n)}NO_2$, or $Q_{(n)}Ar^2$; wherein:
$R^1$ and $R^2$ or $R^2$ and $R^3$ are optionally taken together to form a 4–8 membered saturated, partially unsaturated, or fully unsaturated ring having 0–3 heteroatoms independently selected from nitrogen, oxygen, or sulfur;
n is zero or one;
Q is a $C_{1-4}$ alkylidene chain wherein one methylene unit of Q is optionally replaced by O, S, NR, NRCO, NRCONR, $NRCO_2$, CO, $CO_2$, CONR, OC(O)NR, $SO_2$, $SO_2NR$, $NRSO_2$, $NRSO_2NR$, C(O)C(O), or C(O)$CH_2$C(O);
each R is independently selected from hydrogen or an optionally substituted $C_1$–$C_4$ aliphatic, wherein:

two R bound to the same nitrogen atom are optionally taken together with the nitrogen atom to form a 3–7 membered saturated, partially unsaturated, or fully unsaturated ring having 1–2 additional heteroatoms independently selected from nitrogen, oxygen, or sulfur;
$R^4$ is $Ar^1$, T-$Ar^2$, or $T_{(n)}$-$Ar^3$;
T is a $C_{1-2}$ alkylidene chain wherein one methylene unit of T is optionally replaced by O, NR, NRCO, NRCONR, $NRCO_2$, CO, $CO_2$, CONR, OC(O)NR, $SO_2$, $SO_2NR$, $NRSO_2$, $NRSO_2NR$, C(O)C(O), or C(O)$CH_2$C(O);
$Ar^1$ is a 5–6 membered monocyclic or 8–10 membered bicyclic saturated, partially unsaturated, or fully unsaturated ring system; wherein:
$Ar^1$ is optionally substituted with up to five substituents, wherein the first substituent is selected from $R^x$ or $R^5$ and wherein any additional substituents are independently selected from $R^5$;
each $R^x$ is independently selected from a 5–6 membered aryl ring having 0–3 heteroatoms selected from nitrogen, oxygen, or sulfur, wherein:
$R^x$ is optionally substituted with 1–3 $R^5$;
each $R^5$ is independently selected from R, halogen, $NO_2$, CN, OR, SR, $N(R)_2$, NRC(O)R, NRC(O)N(R)$_2$, $NRCO_2R$, C(O)R, $CO_2R$, C(O)N(R)$_2$, OC(O)N(R)$_2$, SOR, $SO_2R$, $SO_2N(R)_2$, $NRSO_2R$, $NRSO_2N(R)_2$, C(O)C(O)R, or C(O)$CH_2$C(O)R, wherein when the $R^4$ group of said compound of formula II is $Ar^1$, each $R^5$ is independently selected from R, halogen, $NO_2$, OR, or $N(R)_2$;
$Ar^2$ is a 5–6 membered saturated, partially unsaturated, or fully unsaturated monocyclic ring having 0–3 heteroatoms independently selected from nitrogen, oxygen, or sulfur, or an 8–10 membered saturated, partially unsaturated, or fully unsaturated bicyclic ring system having 0–5 heteroatoms independently selected from nitrogen, oxygen, or sulfur; wherein:

$Ar^2$ is optionally substituted with up to five substituents, wherein the first substituent is selected from $R^x$ or $R^5$ and wherein any additional substituents are independently selected from $R^5$;

$Ar^3$ is a 6-membered aryl ring having 0–2 nitrogens, wherein:

$Ar^3$ is substituted with one $Z-R^6$ group and optionally substituted with 1–3 $R^5$;

Z is a $C_1$–$C_6$ alkylidene chain wherein up to two non-adjacent methylene units of Z are optionally replaced by $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and $R^6$ is selected from $Ar^2$, R, halogen, $NO_2$, CN, OR, SR, $N(R)_2$, NRC(O)R, $NRC(O)N(R)_2$, $NRCO_2R$, C(O)R, $CO_2R$, OC(O)R, $C(O)N(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$;

provided that:

(i) when $R^4$ is phenyl substituted with at least two OR, wherein R is not hydrogen, then the at least two OR occupy positions on the phenyl ring other than simultaneously meta and para; and (ii) said compound is other than a compound of formula III

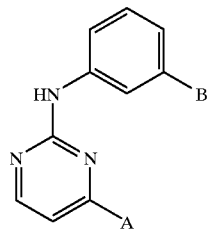

III wherein:

A is a phenyl ring substituted with one or more groups selected from halogen, CN, $OC(O)NH_2$, $CO_2R^{10}$, $COR^{10}$, $SO_2N(R^{10})_2$, $N(R^{10})_2$, $OR^{10}$, or fluoro-alkyl, wherein each $R^{10}$ is independently selected from hydrogen or a $C_1$–$C_7$ alkyl group optionally substituted with $NH_2$, $NH(C_1$–$C_7$ alkyl), or $N(C_1$–$C_7$ alkyl)$_2$; and B is selected from halogen, CN, $OC(O)NH_2$, $CO_2R^{10}$, $COR^{10}$, $SO_2N(R^{10})_2$, $N(R^{10})_2$, $OR^{10}$, fluoro-($C_1$–$C_7$ alkoxy), or fluoro-($C_1$–$C_7$ alkyl).

2. The compound according to claim 1, wherein:

$R^1$, $R^2$, and $R^3$ are independently selected from halogen, QR or $QAr^2$;

Q is a $C_{1-3}$ alkylidene chain wherein one methylene unit of Q is optionally replaced by —O—, —S—, —NHCO—, or —NR—; and $Ar^2$ is an optionally substituted 5–6 membered saturated, partially unsaturated, or fully unsaturated ring having 0–2 heteroatoms independently selected from nitrogen, oxygen, or sulfur.

3. The compound according to claim 2, wherein:

$R^1$, $R^2$, and $R^3$ are independently selected from OH, $OCH_3$, $OCH_2CH_3$, NHCOMe, $NH_2$, $NH(C_{1-4}$ aliphatic), $N(C_{1-4}$ aliphatic)$_2$, $O(CH_2)_2$morpholin-4-yl, $O(CH_2)_2NH_2$, $O(CH_2)_2NH(C_{1-4}$ aliphatic), $O(CH_2)_2N(C_{1-4}$ aliphatic)$_2$, bromo, chloro, or fluoro; or $R^1$ and $R^2$ or $R^2$ and $R^3$ are taken together to form

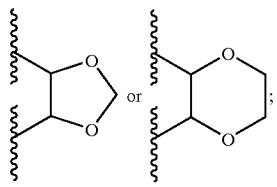

and $Ar^2$ is selected from morpholin-4-yl, pyrrolidin-1-yl, piperidin-1-yl, thiomorpholin-4-yl, pyrazol-1-yl, or imidazol-1-yl.

4. The compound according to claim 1, wherein:

$R^4$ is selected from:

(a) an optionally substituted 6-membered saturated, partially unsaturated, or aryl ring having 0–3 nitrogens;

(b) an optionally substituted 9–10 membered bicyclic aryl ring having 0–2 nitrogens; or (c) an optionally substituted 5 membered heteroaryl ring having 2–3 heteroatoms independently selected from nitrogen, oxygen, or sulfur.

5. The compound according to claim 4, wherein said ring is substituted with 1–3 groups independently selected from $R^x$, R, halogen, $NO_2$, OR, $N(R)_2$, or $Z-R^6$.

6. The compound according to claim 5, wherein $R^x$ is selected from a phenyl, pyridyl, or pyrimidinyl ring optionally substituted with 1–2 $R^5$.

7. The compound according to claim 5, wherein Z is a $C_{1-4}$ alkylidene chain wherein one methylene unit of Z is optionally replaced by —O—, —S—, —$SO_2$—, or —NH—.

8. The compound according to claim 4, wherein said ring is selected from a substituted phenyl, cyclohexyl, naphthyl, pyridyl, pyrimidinyl, triazinyl, thiazolyl, thiadiazolyl, pyrazolyl, isoxazolyl, indazolyl, or benzimidazolyl ring.

9. The compound according to claim 8, wherein said ring is optionally substituted with 1–2 groups independently selected from chloro, fluoro, bromo, methyl, ethyl, t-butyl, isopropyl, cyclopropyl, nitro, OMe, OEt, $CF_3$, $NH_2$, benzyl, benzyloxy, OH, methylene dioxy, $SO_2NH_2$, phenoxy, O-pyridinyl, $SO_2$phenyl, nitrophenoxy, aminophenoxy, S-dimethylpyrimidine, NHphenyl, NH-methoxyphenyl, pyridinyl, aminophenyl, phenol, chloro-fluoro-phenyl, dimethylaminophenyl, $CF_3$-phenyl, dimethylphenyl, chlorophenyl, fluorophenyl, methoxyphenyl, chlorophenoxy, ethoxyphenoxy, or fluorophenoxy.

10. A compound according to claim 1, selected from the following compounds of formulae I and II:

Compounds of Formula I
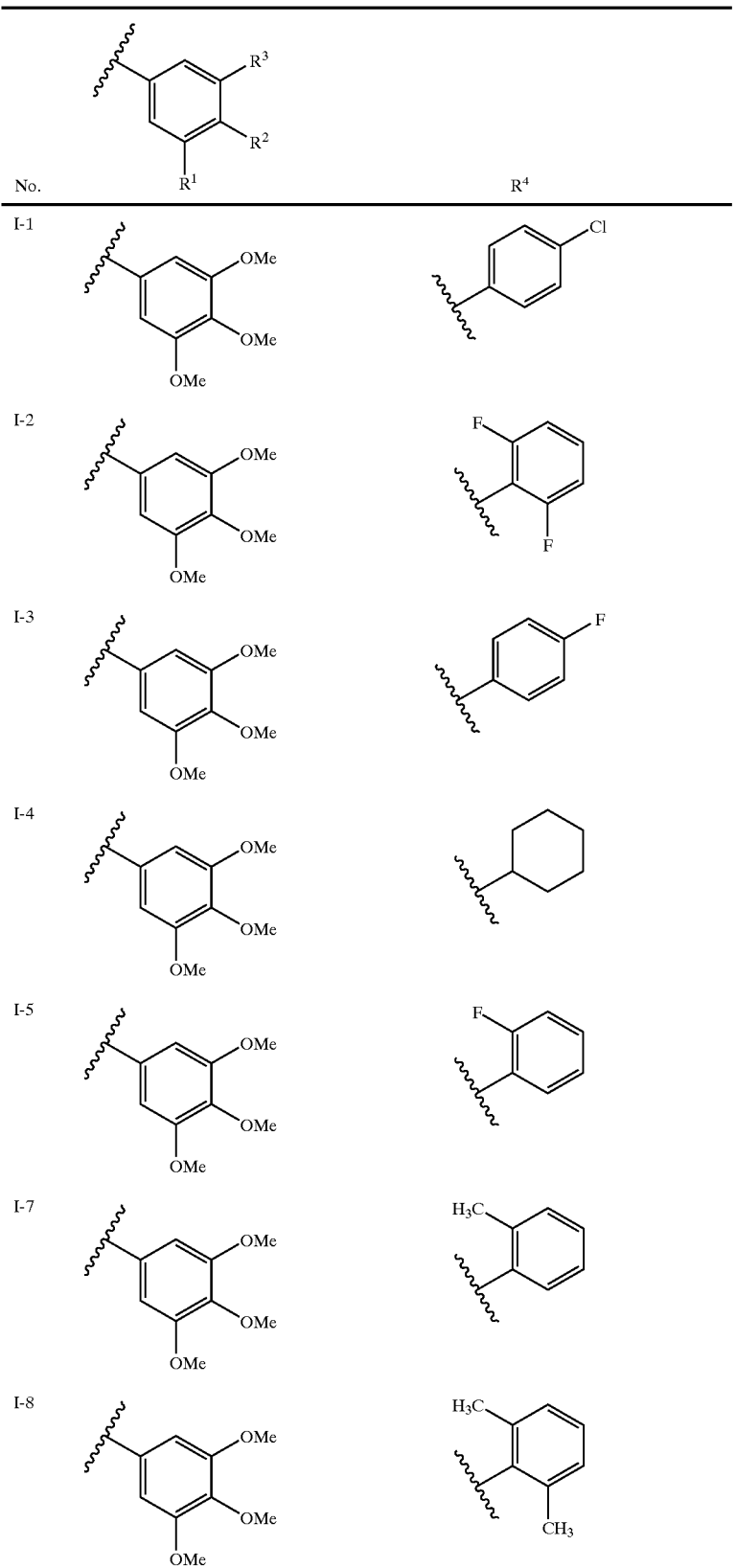

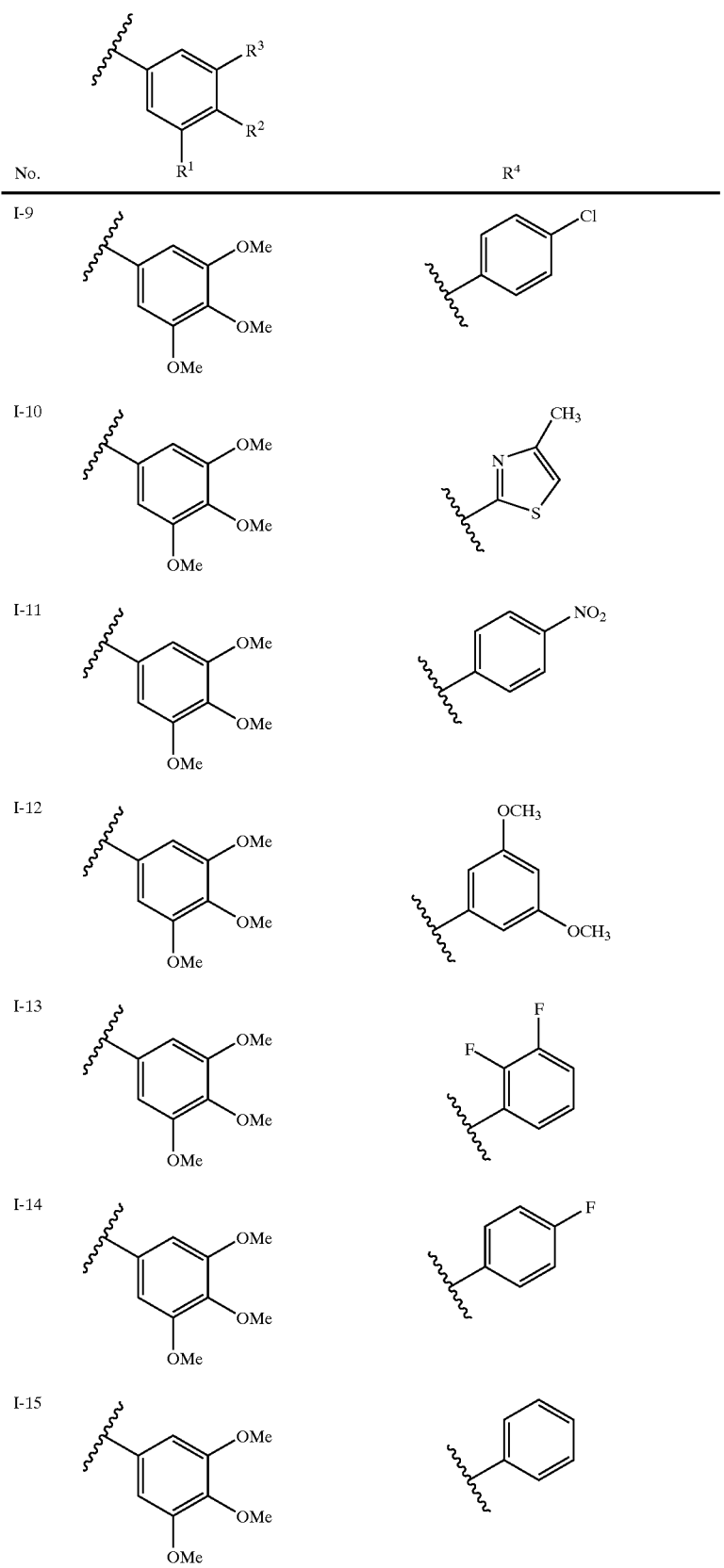

-continued

| No. | ![R1,R2,R3 phenyl] | R⁴ |
|---|---|---|
| I-16 | 3,4,5-tri-OMe phenyl | 2-methylphenyl |
| I-17 | 3,4,5-tri-OMe phenyl | 4-methylphenyl |
| I-21 | 3,4,5-tri-OMe phenyl | 4-methoxyphenyl |
| I-22 | 3,4,5-tri-OMe phenyl | 3,4,5-trifluorophenyl |
| I-23 | 3,4,5-tri-OMe phenyl | 3,5-dichlorophenyl |
| I-24 | 3,4,5-tri-OMe phenyl | 3,5-dimethylphenyl |
| I-25 | 3,4,5-tri-OMe phenyl | 3,4-dimethylphenyl |

-continued

| No. | R¹, R², R³ (phenyl substitution pattern) | R⁴ |
|---|---|---|
| I-26 | 4-OMe-benzo[1,3]dioxol-5-yl | phenyl |
| I-27 | 4-OMe-benzo[1,3]dioxol-5-yl | 3-methylphenyl |
| I-28 | 4-OMe-benzo[1,3]dioxol-5-yl | 4-methylphenyl |
| I-29 | 4-OMe-benzo[1,3]dioxol-5-yl | 3-fluorophenyl |
| I-30 | 4-OMe-benzo[1,3]dioxol-5-yl | 3-chlorophenyl |
| I-31 | 4-OMe-benzo[1,3]dioxol-5-yl | 3-CF₃-phenyl |
| I-32 | 4-OMe-benzo[1,3]dioxol-5-yl | 3-OCH₃-phenyl |

-continued
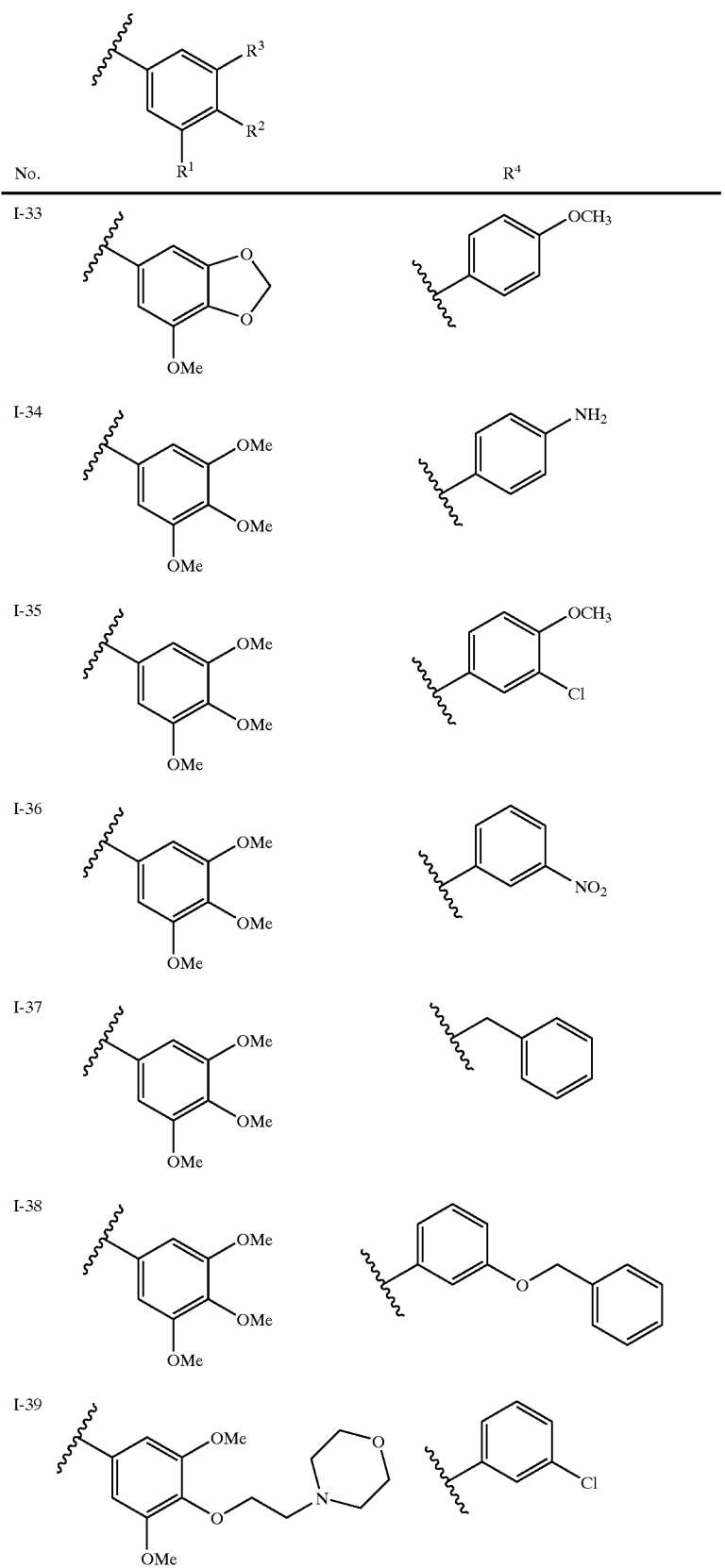

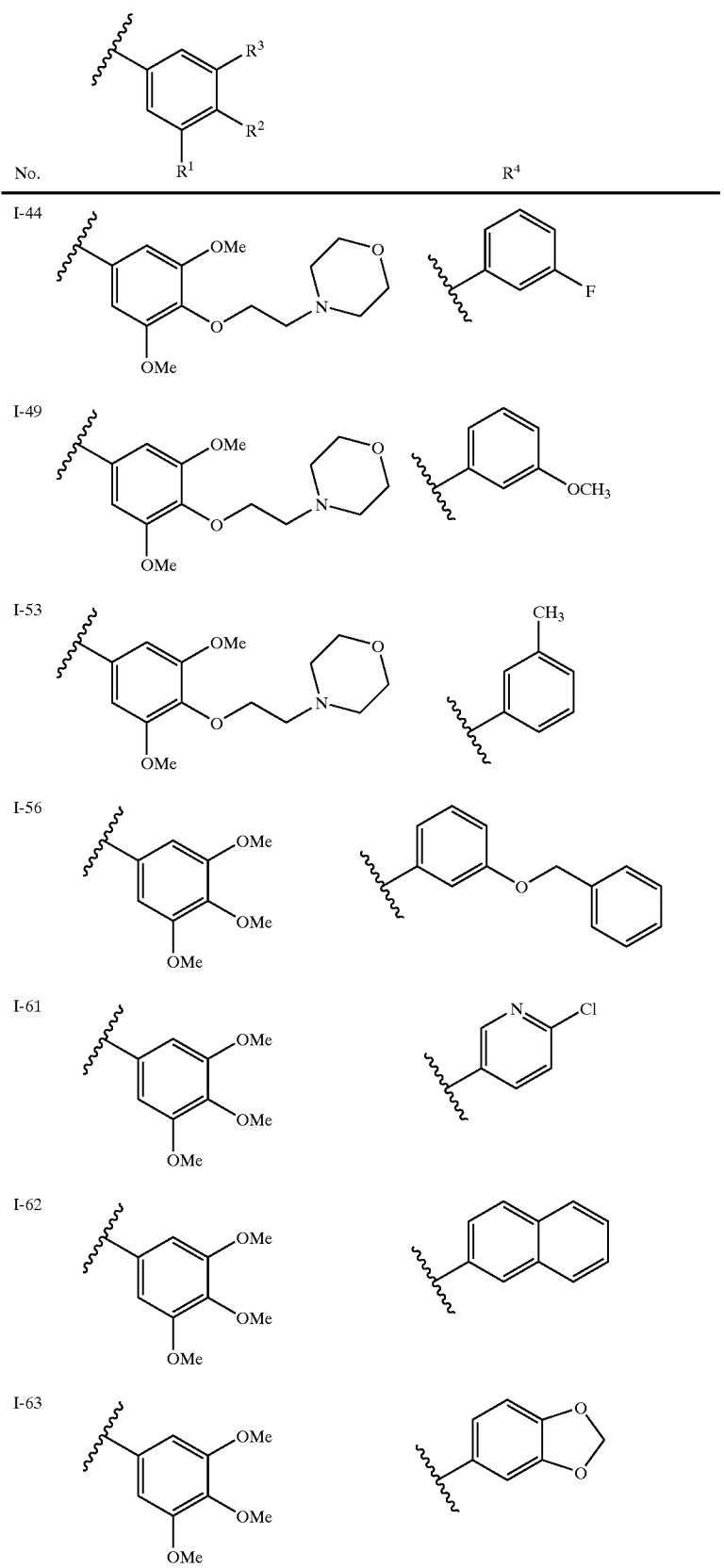

-continued
| No. | 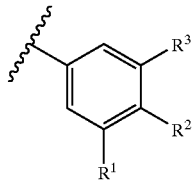 R¹, R², R³ | R⁴ |
|---|---|---|
| I-65 | 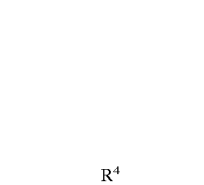 3,4,5-tri-OMe | 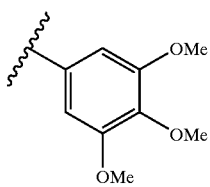 benzimidazol-2-yl |
| I-66 | 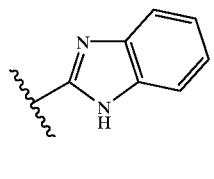 3,4,5-tri-OMe | 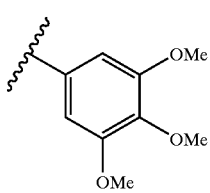 4-sulfamoylphenyl |
| I-67 | 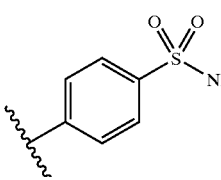 | 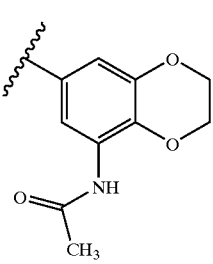 |
| I-68 | 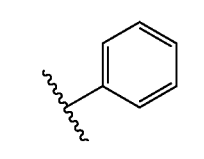 | 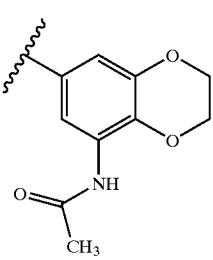 |
| I-69 | 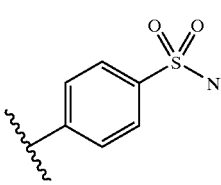 | 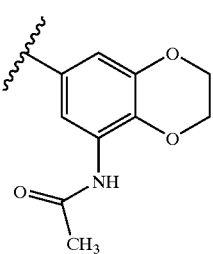 |
| I-70 | 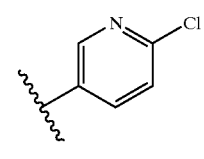 | 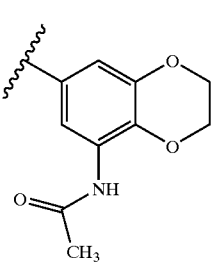 |

-continued
| No. | 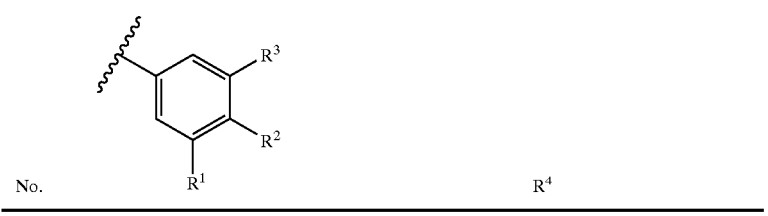 | R⁴ |
|---|---|---|
| I-71 | 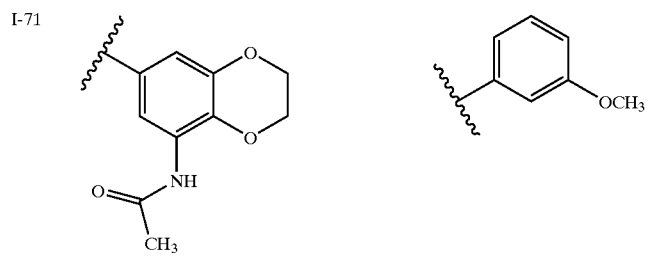 | |
| I-72 | 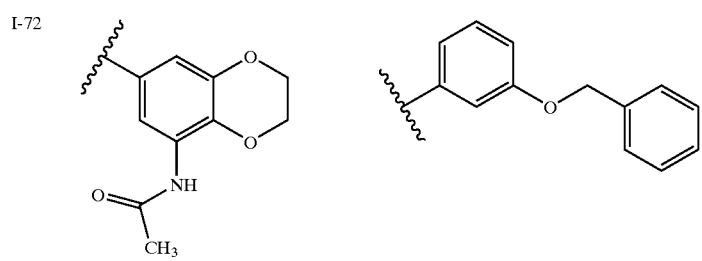 | |
| I-73 | 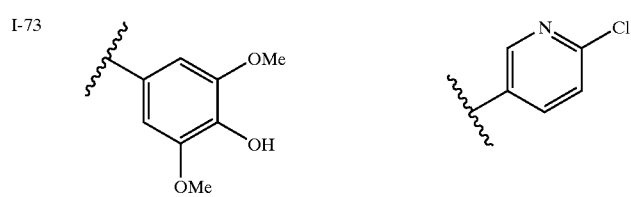 | |
| I-74 | 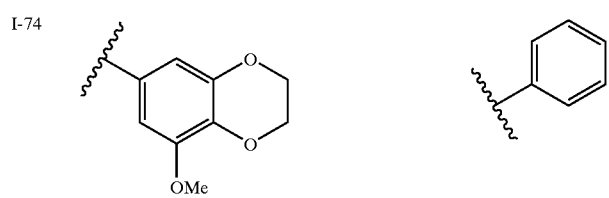 | |
| I-75 | 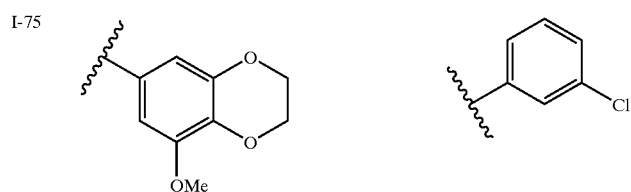 | |
| I-76 | 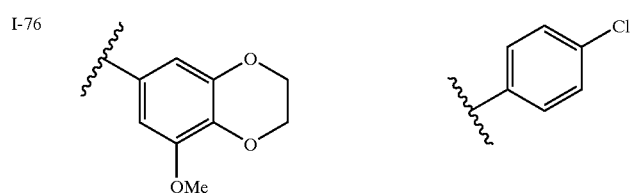 | |

| No. | 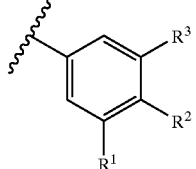 R¹, R², R³ | R⁴ |
|---|---|---|
| I-77 |  | 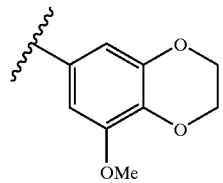 |
| I-78 | 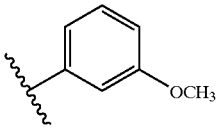 | 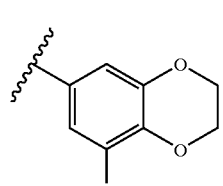 |
| I-79 | 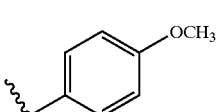 | 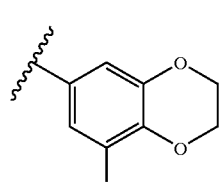 |
| I-81 | 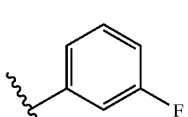 | 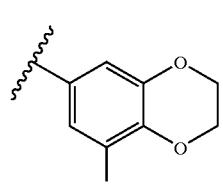 |
| I-82 | 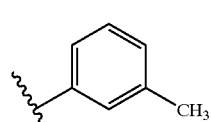 | 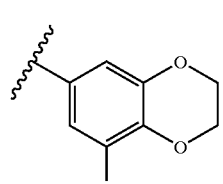 |
| I-83 | 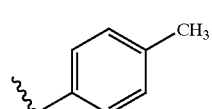 | 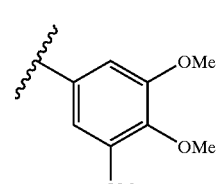 |
| I-84 | 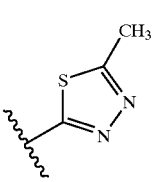 | 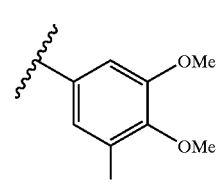 |

-continued
| No. | 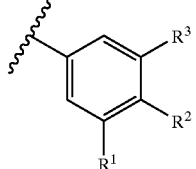 R¹, R², R³ | R⁴ |
|---|---|---|
| I-85 | 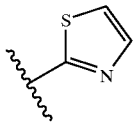 3,4,5-tri-OMe | 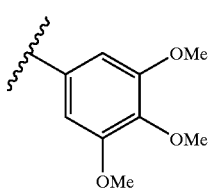 thiazol-2-yl |
| I-86 | 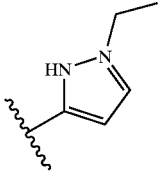 3,4,5-tri-OMe | 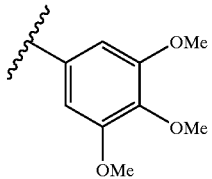 1-ethyl-1H-pyrazol-3-yl |
| I-87 | 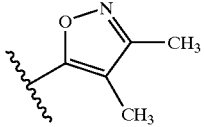 3,4,5-tri-OMe | 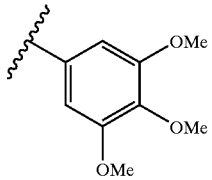 3,4-dimethylisoxazol-5-yl |
| I-88 | 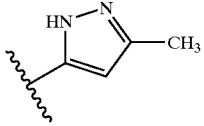 3,4,5-tri-OMe | 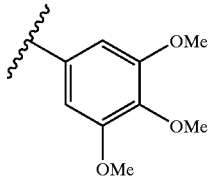 3-methyl-1H-pyrazol-5-yl |
| I-89 | 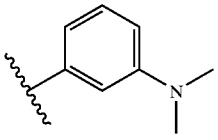 3,4,5-tri-OMe | 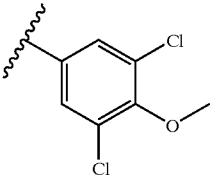 3-(dimethylamino)phenyl |
| I-90 | 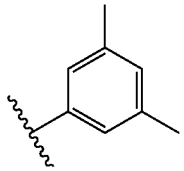 3,5-dichloro-4-OMe | 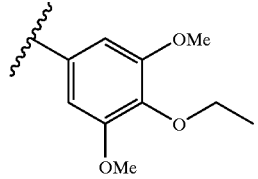 3,5-dimethylphenyl |
| I-91 | 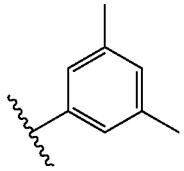 3,5-di-OMe-4-OEt | 3,5-dimethylphenyl |

| No. | ![R1,R2,R3 phenyl] | R⁴ |
|---|---|---|
| I-92 | 3,5-diCl, 4-OMe phenyl | 3,5-diOMe phenyl |
| I-93 | 3,5-diOMe, 4-OEt phenyl | 3,5-diOMe phenyl |
| I-94 | 3,4,5-triOMe phenyl | 3-SO₂NH₂ phenyl |

Compounds of Formula II

| No. | ![R1,R2,R3 phenyl] | R⁴ |
|---|---|---|
| II-1 | 2,3,4-tri(OCH₃) phenyl | 3-phenoxy phenyl |
| II-2 | 2,3,4-tri(OCH₃) phenyl | 3-benzyloxy phenyl |

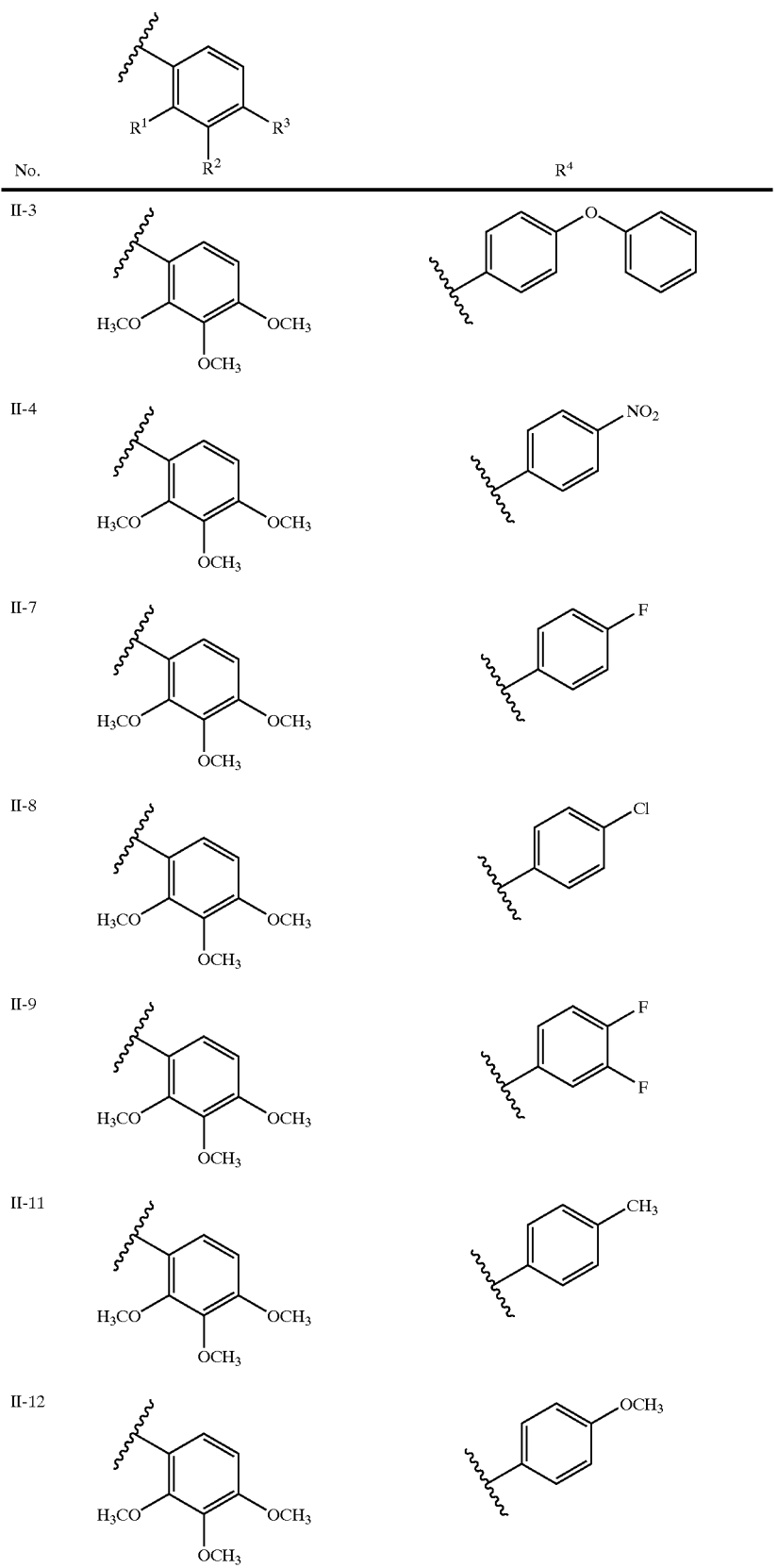

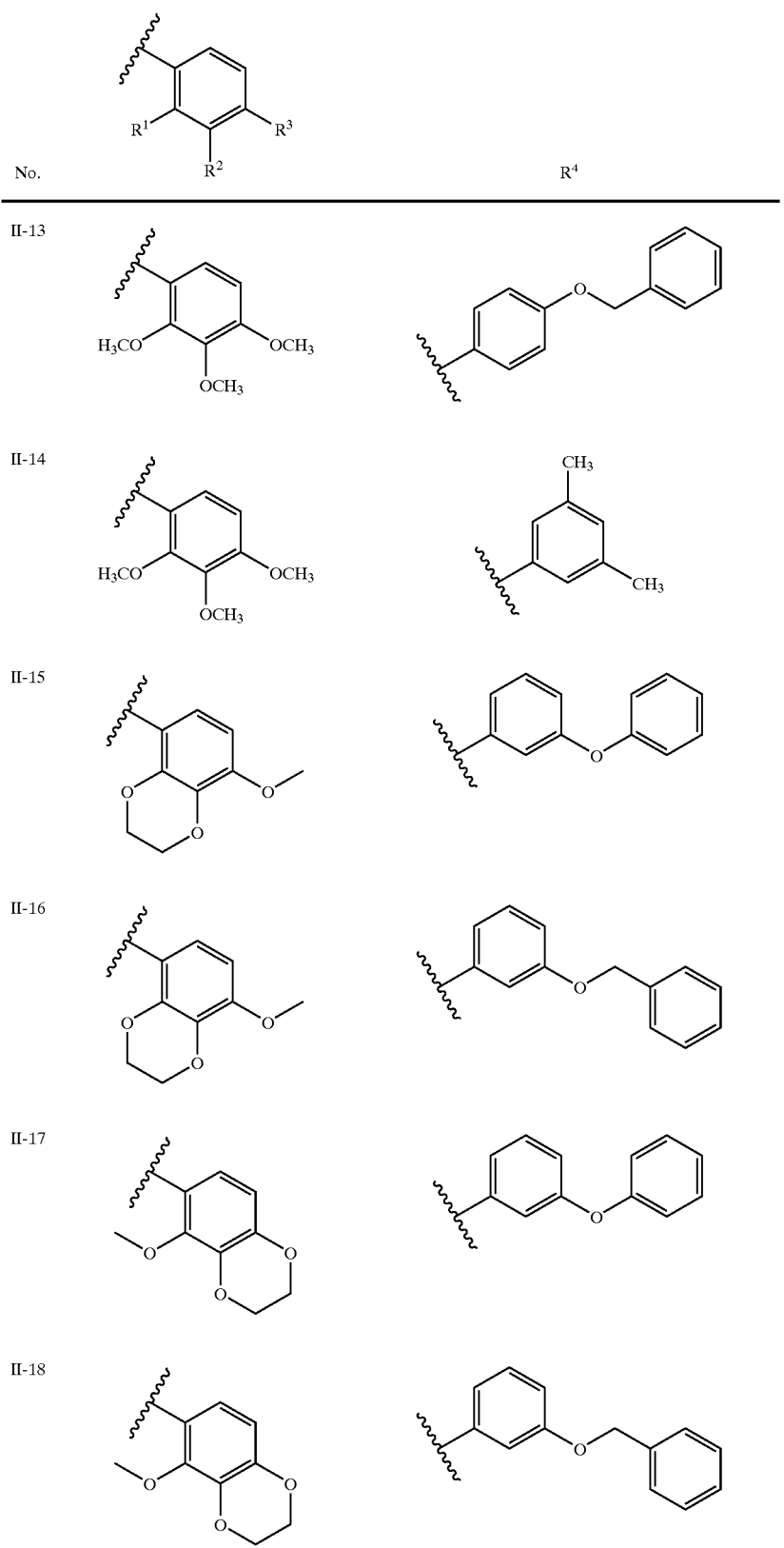

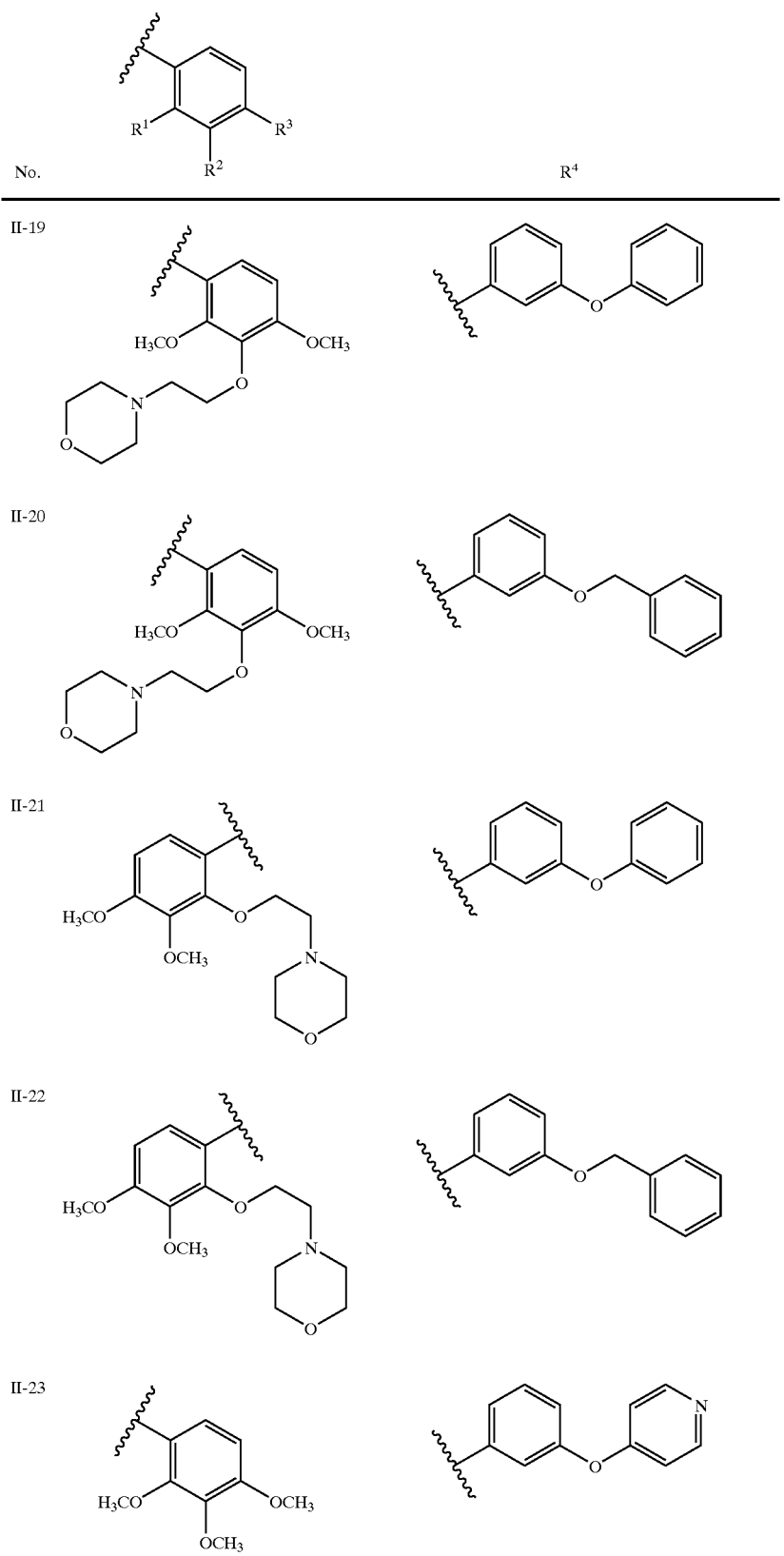

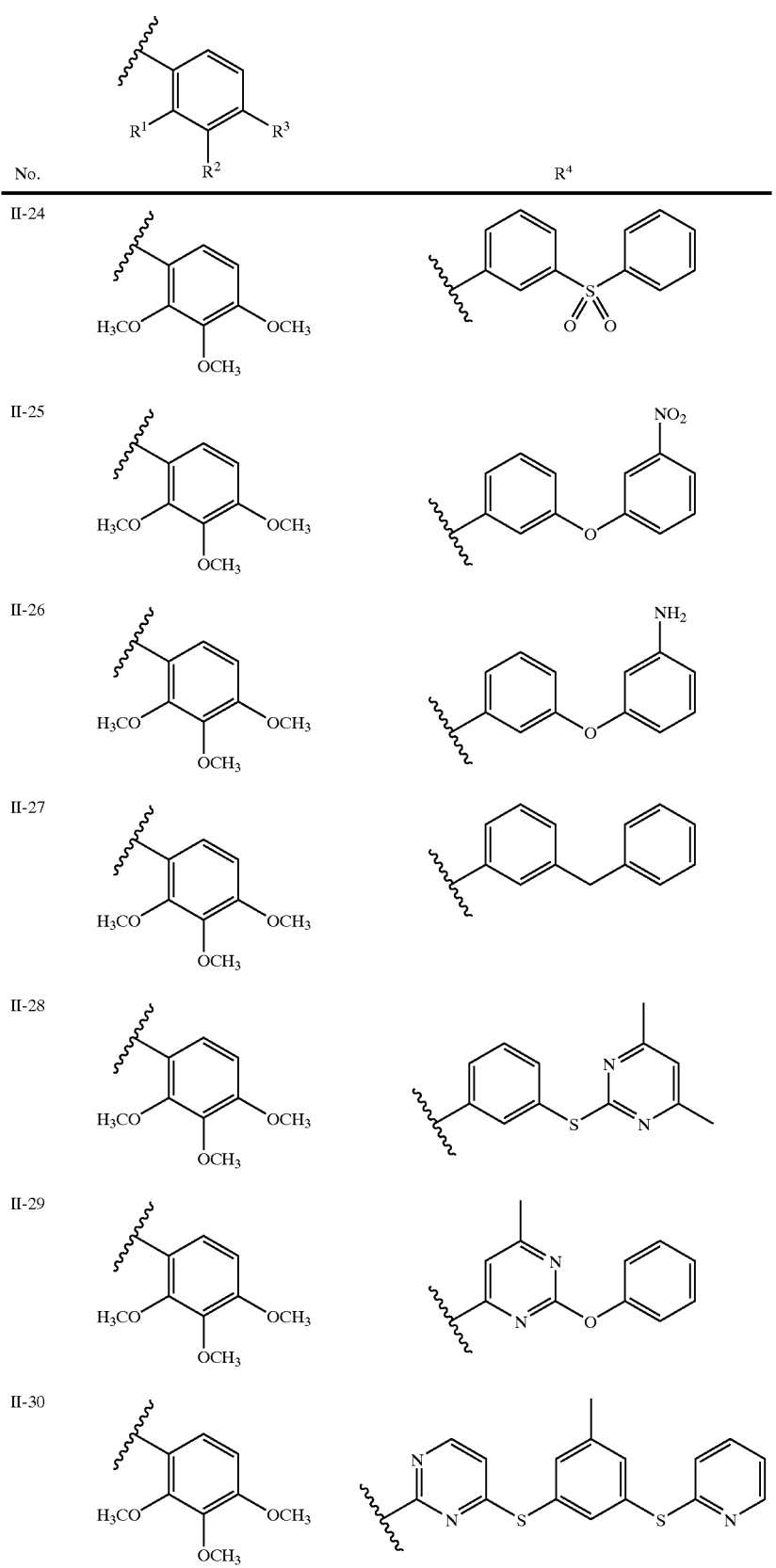

-continued
| No. | | $R^4$ |
|---|---|---|
| II-31 | 3,4-di-OCH₃, 2-... (R¹=H, R²=OCH₃, R³=OCH₃) | 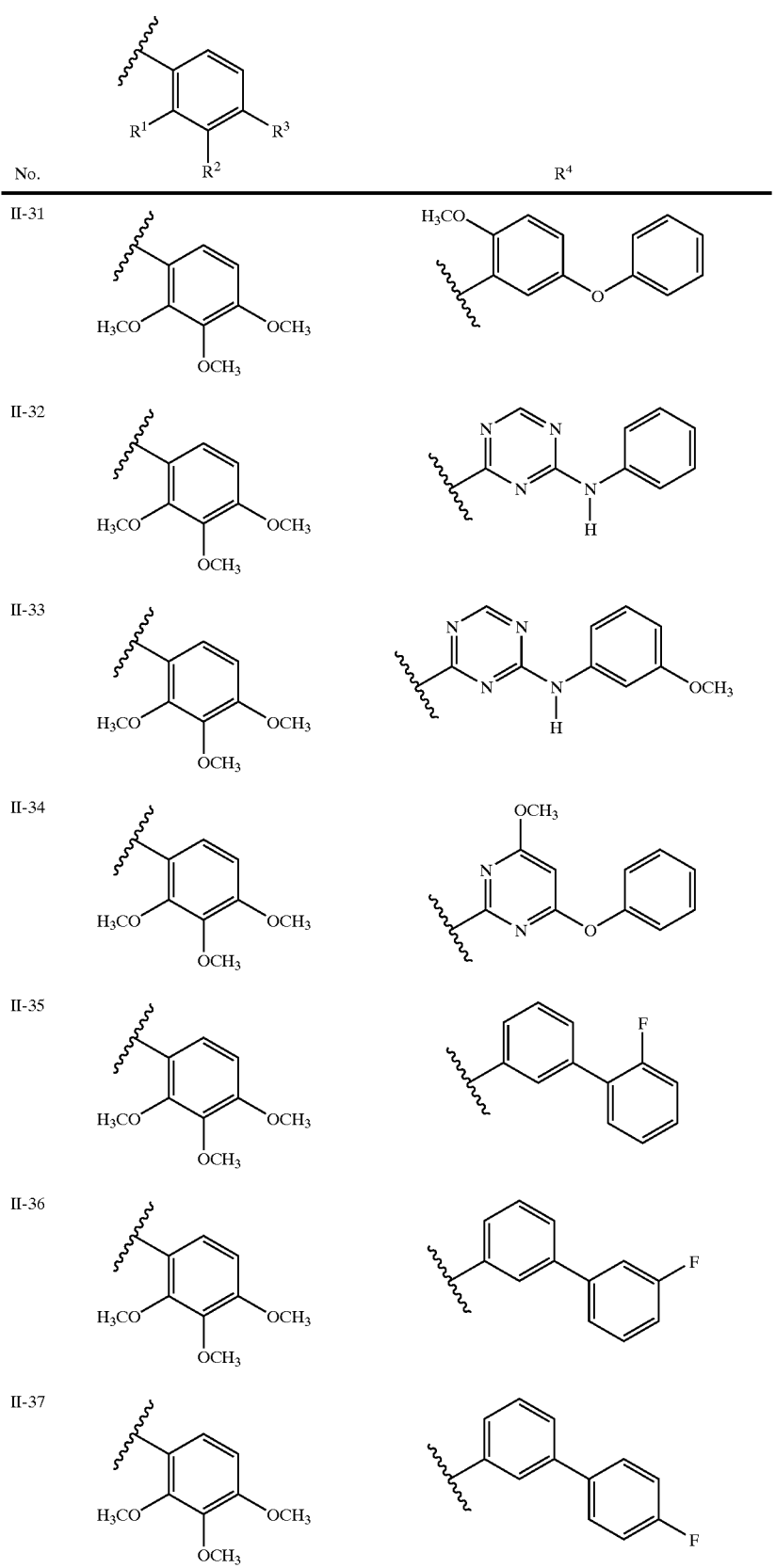 |
| II-32 | | |
| II-33 | | |
| II-34 | | |
| II-35 | | |
| II-36 | | |
| II-37 | | |

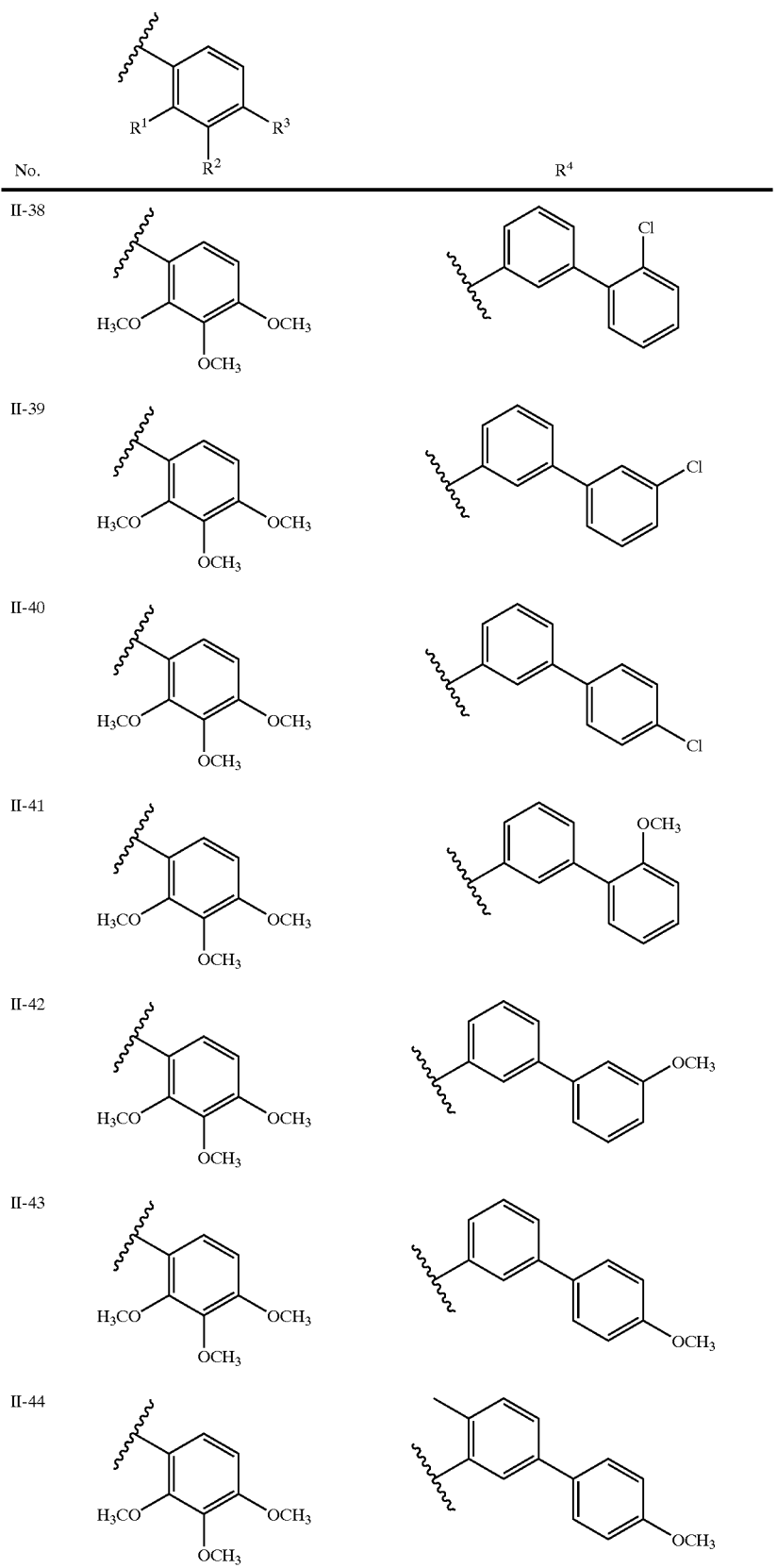

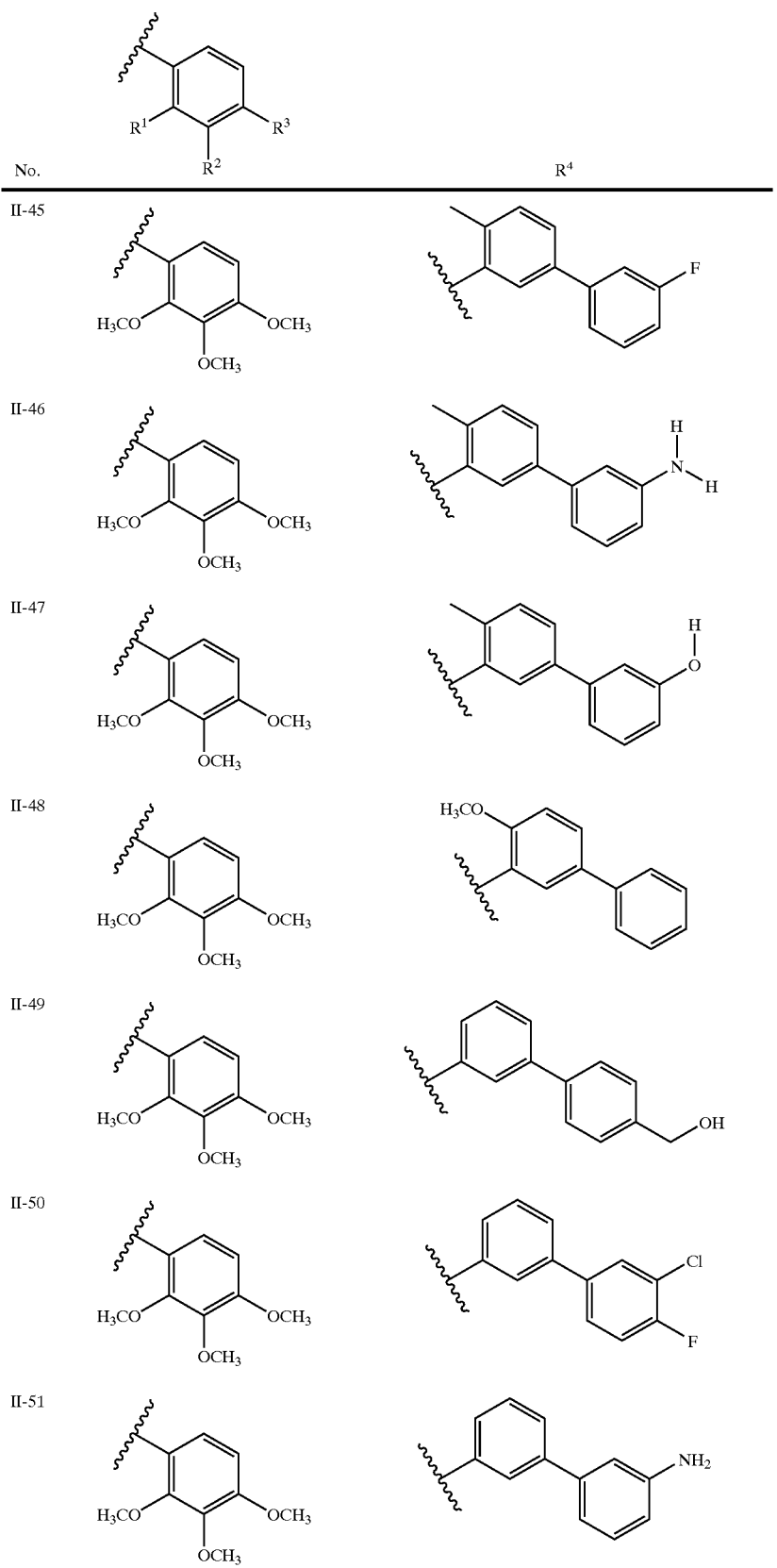

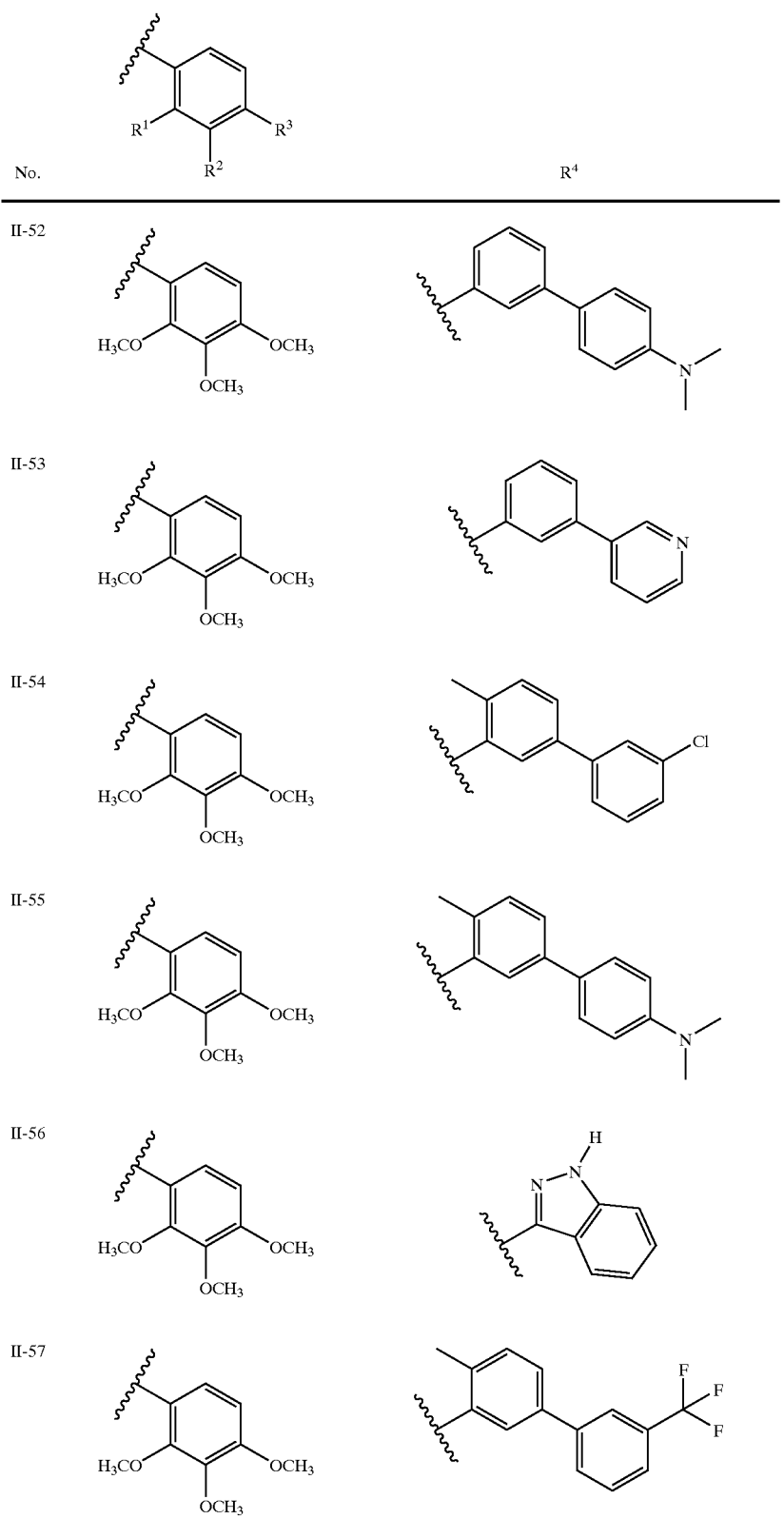

-continued
| No. | 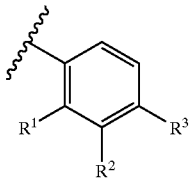 | R⁴ |
|---|---|---|
| II-58 | 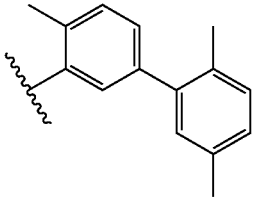 | 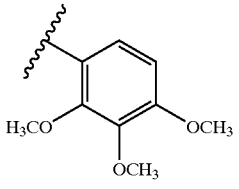 |
| II-59 | 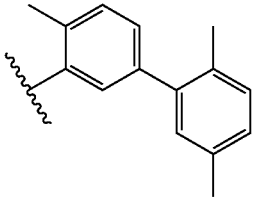 | 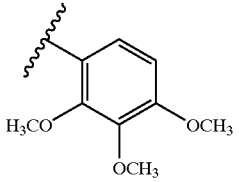 |
| II-60 | 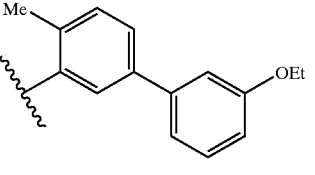 | 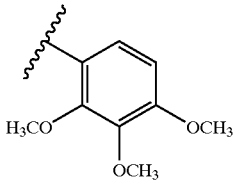 |
| II-61 | 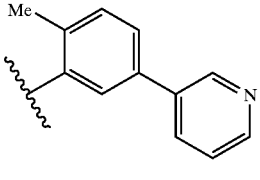 | 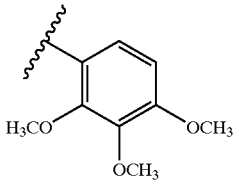 |
| II-62 | 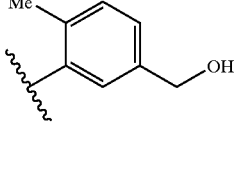 | 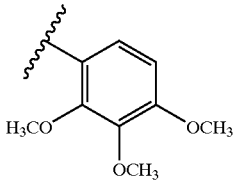 |
| II-63 | 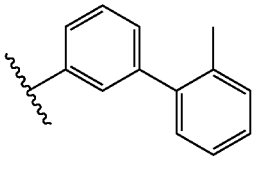 | 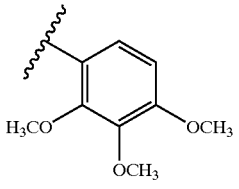 |
| II-64 | 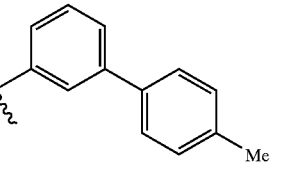 | 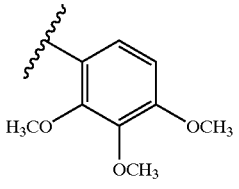 |

-continued
| No. | 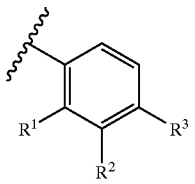 R¹ R² R³ | R⁴ |
|---|---|---|
| II-65 | 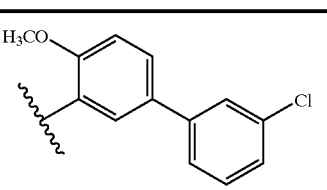 H₃CO, OCH₃, OCH₃ | 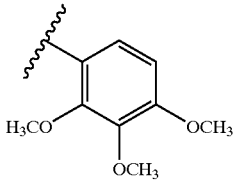 H₃CO, Cl |
| II-66 | 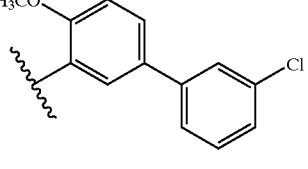 H₃CO, OCH₃, OCH₃ | 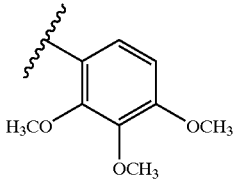 F, Cl |
| II-67 | 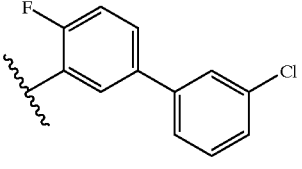 H₃CO, OCH₃, OCH₃ | 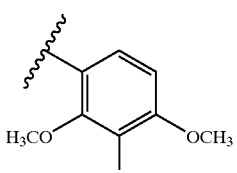 OCH₃, Cl |
| II-68 | 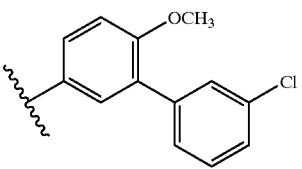 H₃CO, OCH₃, OCH₃ | 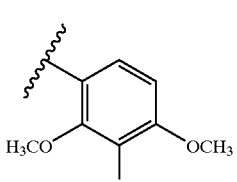 OCH₃, Cl |
| II-69 | 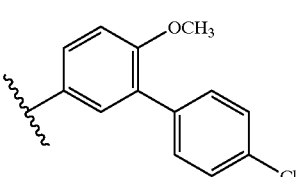 H₃CO, OCH₃, OCH₃ | 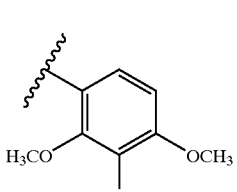 OCH₃, F |
| II-70 | 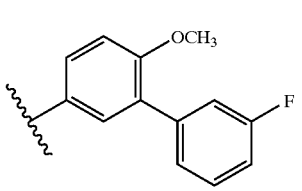 H₃CO, OCH₃, OCH₃ | 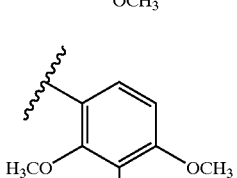 OCH₃, OH |
| II-71 | 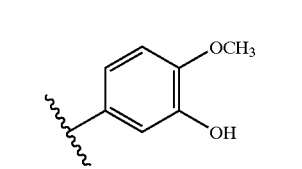 H₃CO, OCH₃, OCH₃ | 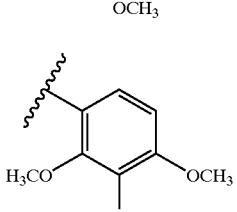 OCH₃, NO₂ |

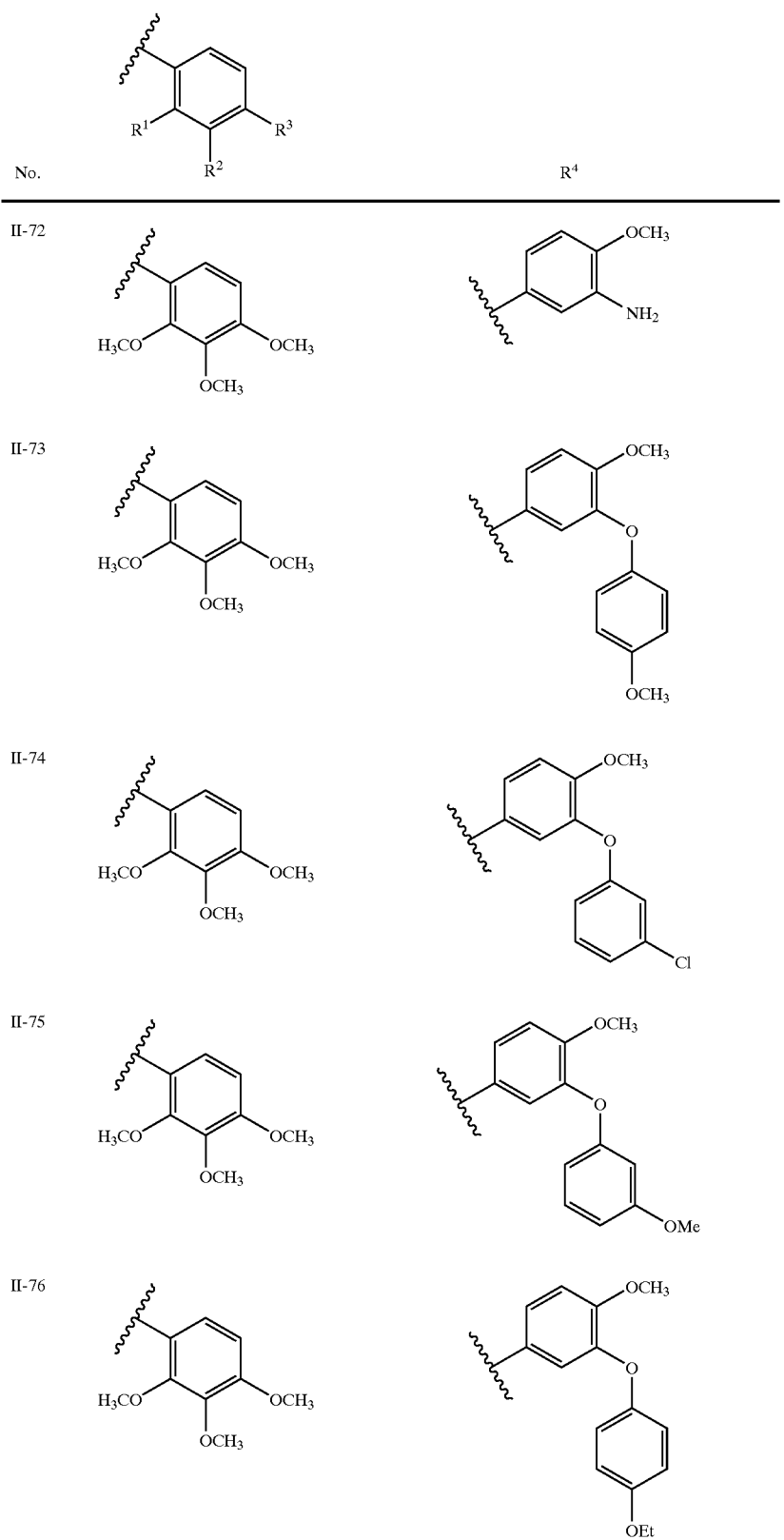

| No. | 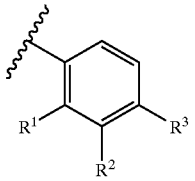 | R⁴ |
|---|---|---|
| II-77 | 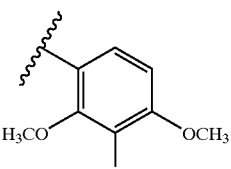 |  |
| II-78 | 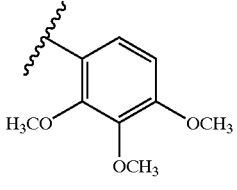 | 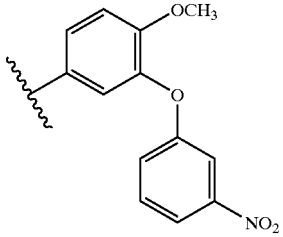 |
| II-79 | 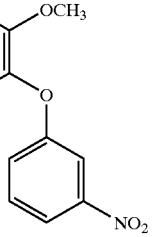 | 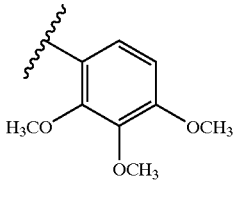 |
| II-80 | 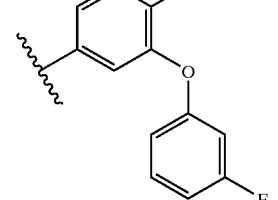 | 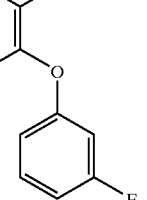 |
| II-81 | 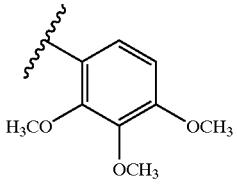 | 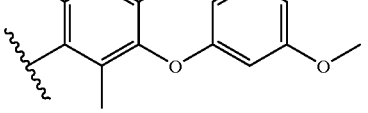 |
| II-82 |  | 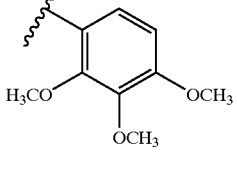 |

-continued

| No. | 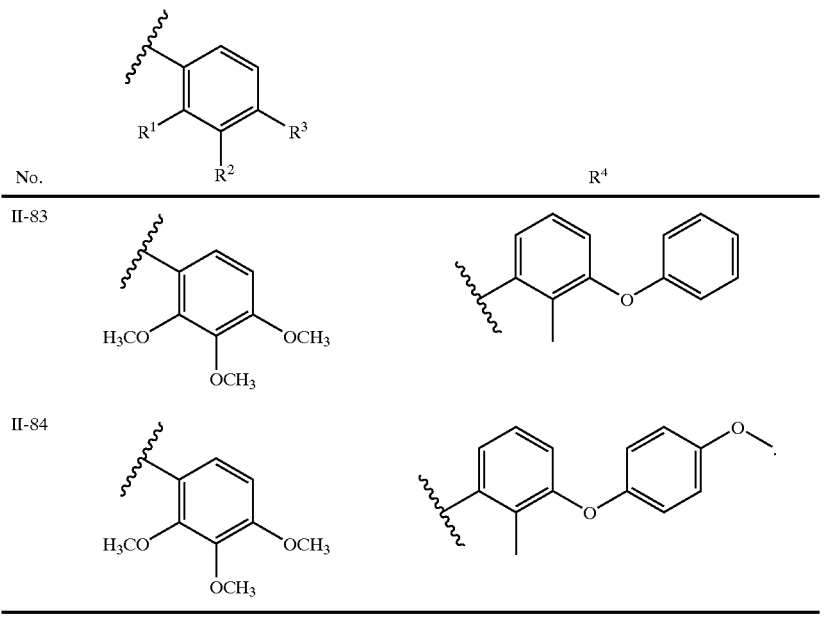 | $R^4$ |
|---|---|---|
| II-83 | | |
| II-84 | | |

11. A composition comprising a compound according to any of claims 1–10 and a pharmaceutically acceptable carrier, adjuvant, or vehicle.

12. The composition according to claim 11, additionally comprising an additional therapeutic agent selected from an anti-proliferative agent, an anti-inflammatory agent, an immunomodulatory agent, a neurotrophic factor, an agent for treating cardiovascular disease, an agent for treating liver disease, an anti-viral agent, an agent for treating blood disorders, an agent for treating diabetes, or an agent for treating immunodeficiency disorders.

13. A compound of formula I or II:

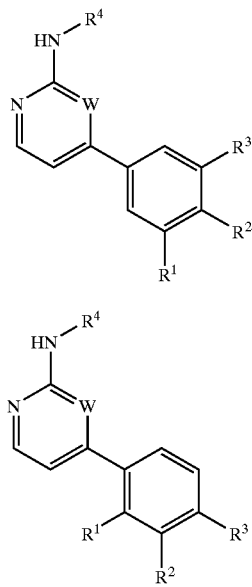

or a pharmaceutically acceptable salt thereof, wherein:

W is nitrogen;

each $R^1$, $R^2$, and $R^3$ is independently selected from halogen, QR, $Q_{(n)}CN$, $Q_{(n)}NO_2$, or $Q_{(n)}Ar^2$; wherein:

$R^1$ and $R^2$ or $R^2$ and $R^3$ are optionally taken together to form a 4–8 membered saturated, partially unsaturated, or fully unsaturated ring having 0–3 heteroatoms independently selected from nitrogen, oxygen, or sulfur;

n is zero or one;

Q is a $C_{1-4}$ alkylidene chain wherein one methylene unit of Q is optionally replaced by O, S, NR, NRCO, NRCONR, $NRCO_2$, CO, $CO_2$, CONR, OC(O)NR, $SO_2$, $SO_2NR$, $NRSO_2$, $NRSO_2NR$, C(O)C(O), or C(O)$CH_2C(O)$;

each R is independently selected from hydrogen or an optionally substituted $C_1-C_4$ aliphatic, wherein:

two R bound to the same nitrogen atom are optionally taken together with the nitrogen atom to form a 3–7 membered saturated, partially unsaturated, or fully unsaturated ring having 1–2 additional heteroatoms independently selected from nitrogen, oxygen, or sulfur;

$R^4$ is $Ar^1$, $T-Ar^2$, or $T_{(n)}-Ar^3$;

T is a $C_{1-2}$ alkylidene chain wherein one methylene unit of T is optionally replaced by O, NR, NRCO, NRCONR, $NRCO_2$, CO, $CO_2$, CONR, OC(O)NR, $SO_2$, $SO_2NR$, $NRSO_2$, $NRSO_2NR$, C(O)C(O), or C(O)$CH_2C(O)$;

$Ar^1$ is a 5–6 membered monocyclic or 8–10 membered bicyclic saturated, partially unsaturated, or fully unsaturated ring system; wherein:

$Ar^1$ is optionally substituted with up to five substituents, wherein the first substituent is selected from $R^x$ or $R^5$ and wherein any additional substituents are independently selected from $R^5$;

each $R^x$ is independently selected from a 5–6 membered aryl ring having 0–3 heteroatoms selected from nitrogen, oxygen, or sulfur, wherein:

$R^x$ is optionally substituted with 1–3 $R^5$;

each $R^5$ is independently selected from R, halogen, $NO_2$, CN, SR, $N(R)_2$, NRC(O)R, $NRC(O)N(R)_2$, $NRCO_2R$, C(O)R, CO₂R, OC(O)N(R)₂, SOR, SO₂R, SO₂N(R)₂, NRSO₂R, NRSO₂N(R)₂, C(O)C(O)R, or C(O)CH₂C(O)R;

Ar² is a 5–6 membered saturated, partially unsaturated, or fully unsaturated monocyclic ring having 0–3 heteroatoms independently selected from nitrogen, oxygen, or sulfur or an 8–10 membered saturated, partially unsaturated, or fully unsaturated bicyclic ring system having 0–5 heteroatoms independently selected from nitrogen, oxygen, or sulfur; wherein:

Ar² is optionally substituted with up to five substituents, wherein the first substituent is selected from $R^x$ or $R^5$ and wherein any additional substituents are independently selected from $R^5$;

Ar³ is a 6-membered aryl ring having 0–2 nitrogens, wherein:

Ar³ is substituted with one Z-$R^6$ group and optionally substituted with 1–3 $R^5$;

Z is a $C_1$-$C_6$ alkylidene chain wherein up to two non-adjacent methylene units of Z are optionally replaced by CO₂, COCO, CONR, OCONR, NRNR, NRNRCO, NRCO, NRCO₂, NRCONR, SO, SO₂, NRSO₂, SO₂NR, NRSO₂NR, S, or NR; and $R^6$ is selected from Ar², R, halogen, NO₂, CN, OR, SR, N(R)₂, NRC(O)R, NRC(O)N(R)₂, NRCO₂R, C(O)R, CO₂R, OC(O)R, C(O)N(R)₂, OC(O)N(R)₂, SOR, SO₂R, SO₂N(R)₂, NRSO₂R, NRSO₂N(R)₂, C(O)C(O)R, or C(O)CH₂C(O)R;

provided that:

(i) when $R^4$ is phenyl substituted with two OR, wherein R is not hydrogen, the two OR occupy positions on the phenyl ring other than simultaneously meta and para; and (ii) said compound is other than a compound of formula III

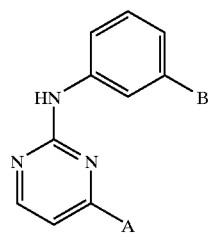

III wherein:

A is a phenyl ring substituted with one or more groups selected from halogen, CN, OC(O)NH₂, CO₂$R^{10}$, COR¹⁰, SO₂N($R^{10}$)₂, N($R^{10}$)₂, O$R^{10}$, or fluoro-alkyl, wherein each $R^{10}$ is independently selected from hydrogen or a $C_1$-$C_7$ alkyl group optionally substituted with NH₂, NH($C_1$-$C_7$ alkyl), or N($C_1$-$C_7$ alkyl)₂; and B is selected from halogen, CN, OC(O)NH₂, CO₂$R^{10}$, COR¹⁰, SO₂N($R^{10}$)₂, N($R^{10}$)₂, O$R^{10}$, or fluoro-($C_1$-$C_7$ alkyl).

14. The compound according to claim 13, wherein:

$R^1$, $R^2$, and $R^3$ are independently selected from halogen, QR or QAr²;

Q is a $C_{1-3}$ alkylidene chain wherein one methylene unit of Q is optionally replaced by —O—, —S—, —NHCO—, or —NR—; and Ar² is an optionally substituted 5–6 membered saturated, partially unsaturated, or fully unsaturated ring having 0–2 heteroatoms independently selected from nitrogen, oxygen, or sulfur.

15. The compound according to claim 14, wherein:

$R^1$, $R^2$, and $R^3$ are independently selected from OH, OCH₃, OCH₂CH₃, NHCOMe, NH₂, NH($C_{1-4}$ aliphatic), N($C_{1-4}$ aliphatic)₂, O(CH₂)₂morpholin-4-yl, O(CH₂)₂NH₂, O(CH₂)₂NH($C_{1-4}$ aliphatic), O(CH₂)₂N($C_{1-4}$ aliphatic)₂, bromo, chloro, or fluoro; or $R^1$ and $R^2$ or $R^2$ and $R^3$ are taken together to form

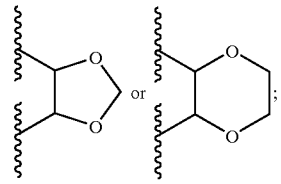

and

Ar² is selected from morpholin-4-yl, pyrrolidin-1-yl, piperidin-1-yl, thiomorpholin-4-yl, pyrazol-1-yl, or imidazol-1-yl.

16. The compound according to claim 15, wherein:

$R^4$ is selected from:

(a) an optionally substituted 6-membered saturated, partially unsaturated, or aryl ring having 0–3 nitrogens;

(b) an optionally substituted 9–10 membered bicyclic aryl ring having 0–2 nitrogens; or (c) an optionally substituted 5 membered heteroaryl ring having 2–3 heteroatoms independently selected from nitrogen, oxygen, or sulfur.

17. The compound according to claim 16, wherein said ring is substituted with 1–3 groups independently selected from $R^x$, R, halogen, NO₂, N(R)₂, or Z-$R^6$.

18. The compound according to claim 17, wherein $R^x$ is selected from a phenyl, pyridyl, or pyrimidinyl ring optionally substituted with 1–2 $R^5$.

19. A composition comprising a compound according to claim 13 and a pharmaceutically acceptable carrier, adjuvant, or vehicle.

20. The composition according to claim 19, additionally comprising an additional therapeutic agent selected from an anti-proliferative agent, an anti-inflammatory agent, an immunomodulatory agent, a neurotrophic factor, an agent for treating cardiovascular disease, an agent for treating liver disease, an anti-viral agent, an agent for treating blood disorders, an agent for treating diabetes, or an agent for treating immunodeficiency disorders.

21. A compound of formula I or II:

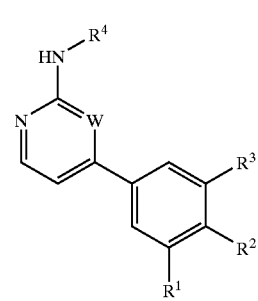

I

-continued

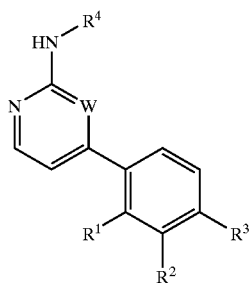

or a pharmaceutically acceptable salt thereof, wherein:

W is nitrogen;

each $R^1$, $R^2$, and $R^3$ is independently selected from halogen, QR, $Q_{(n)}CN$, $Q_{(n)}NO_2$, or $Q_{(n)}Ar^2$; wherein:

$R^1$ and $R^2$ or $R^2$ and $R^3$ are optionally taken together to form a 4–8 membered saturated, partially unsaturated, or fully unsaturated ring having 0–3 heteroatoms independently selected from nitrogen, oxygen, or sulfur;

n is zero or one;

Q is a $C_{1-4}$ alkylidene chain wherein one methylene unit of Q is optionally replaced by O, S, NR, NRCO, NRCONR, NRCCO$_2$, CO, CO$_2$, CONR, OC(O)NR, SO$_2$, SO$_2$NR, NRSO$_2$, NRSO$_2$NR, C(O)C(O), or C(O)CH$_2$C(O);

each R is independently selected from hydrogen or an optionally substituted $C_1$–$C_4$ aliphatic, wherein:

two R bound to the same nitrogen atom are optionally taken together with the nitrogen atom to form a 3–7 membered saturated, partially unsaturated, or fully unsaturated ring having 1–2 additional heteroatoms independently selected from nitrogen, oxygen, or sulfur;

$R^4$ selected from:

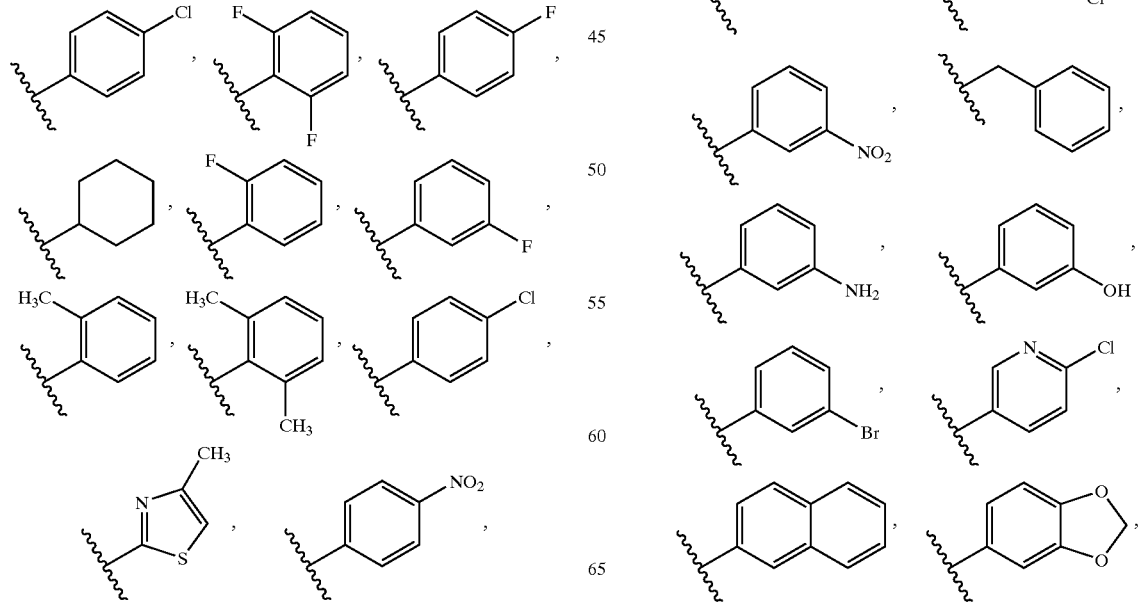

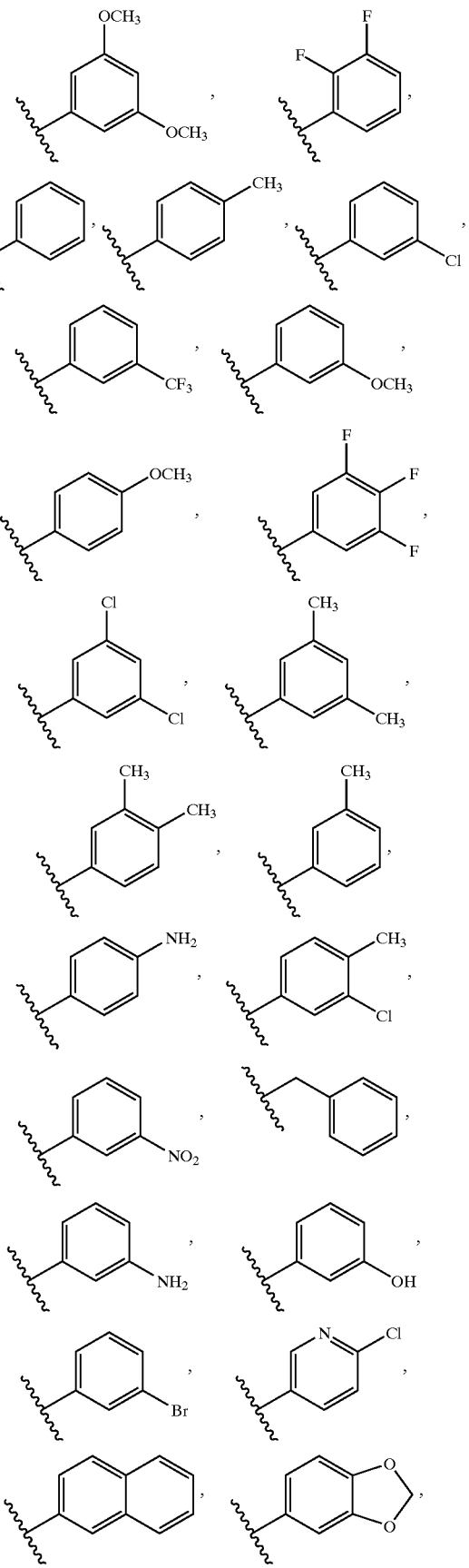

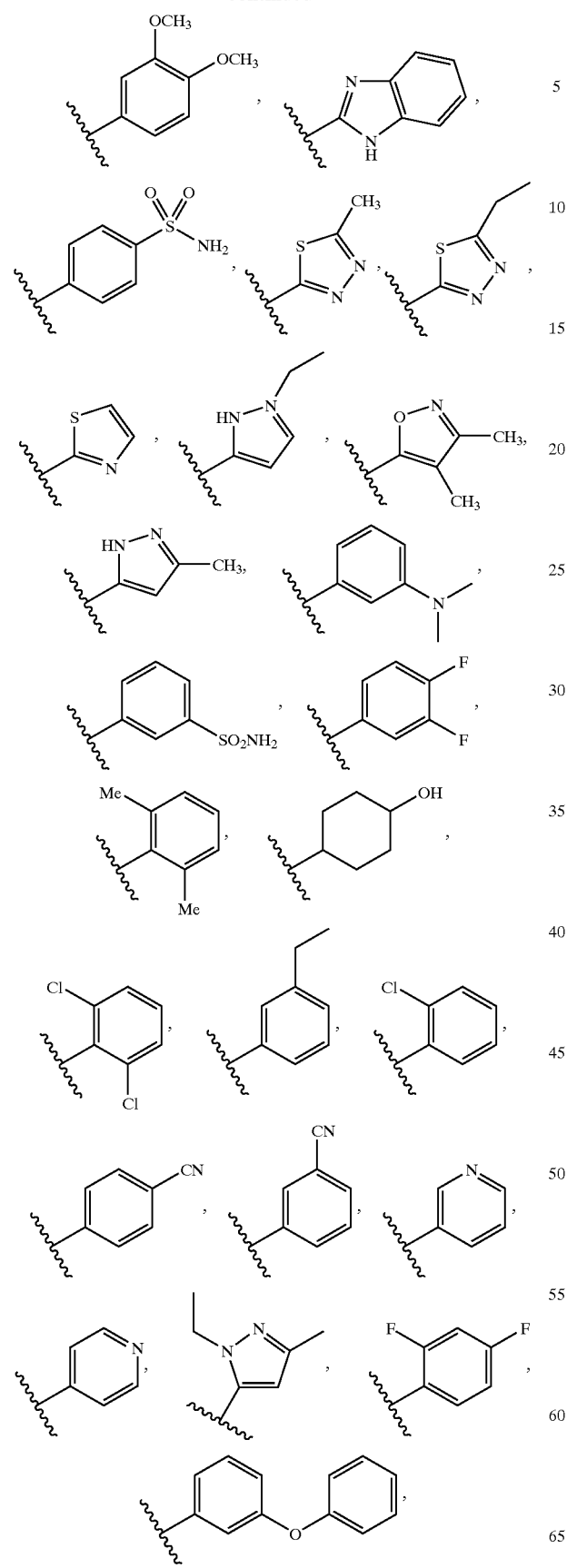
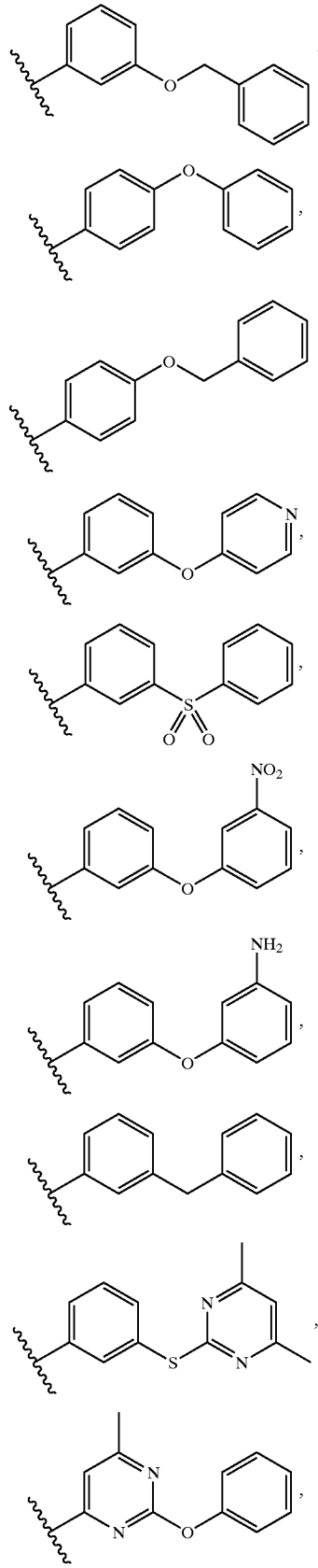

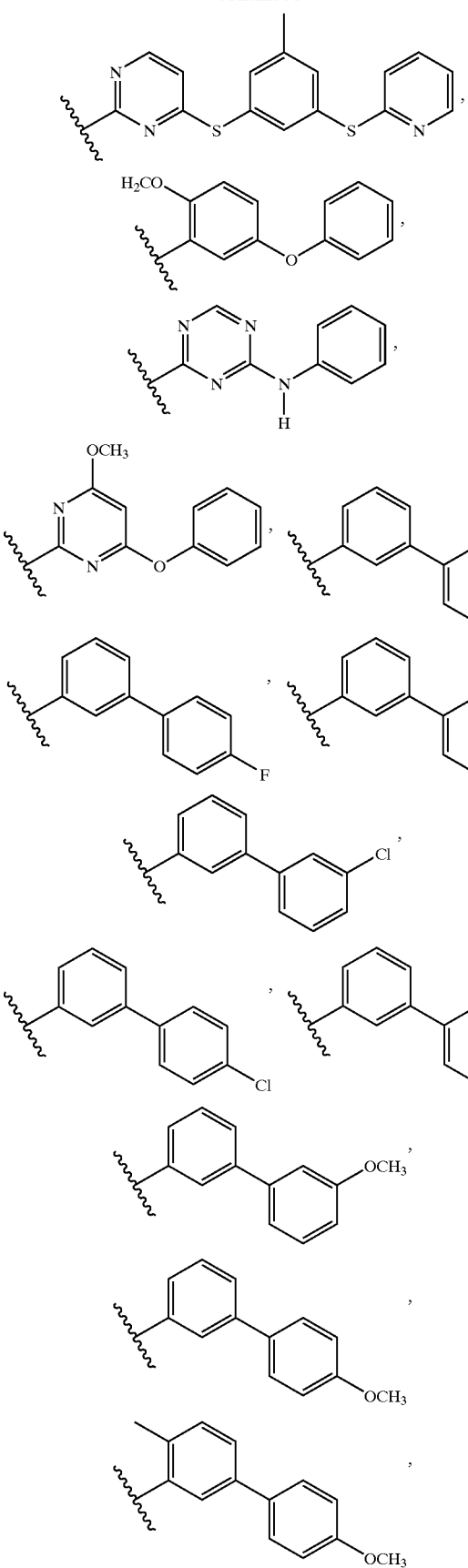
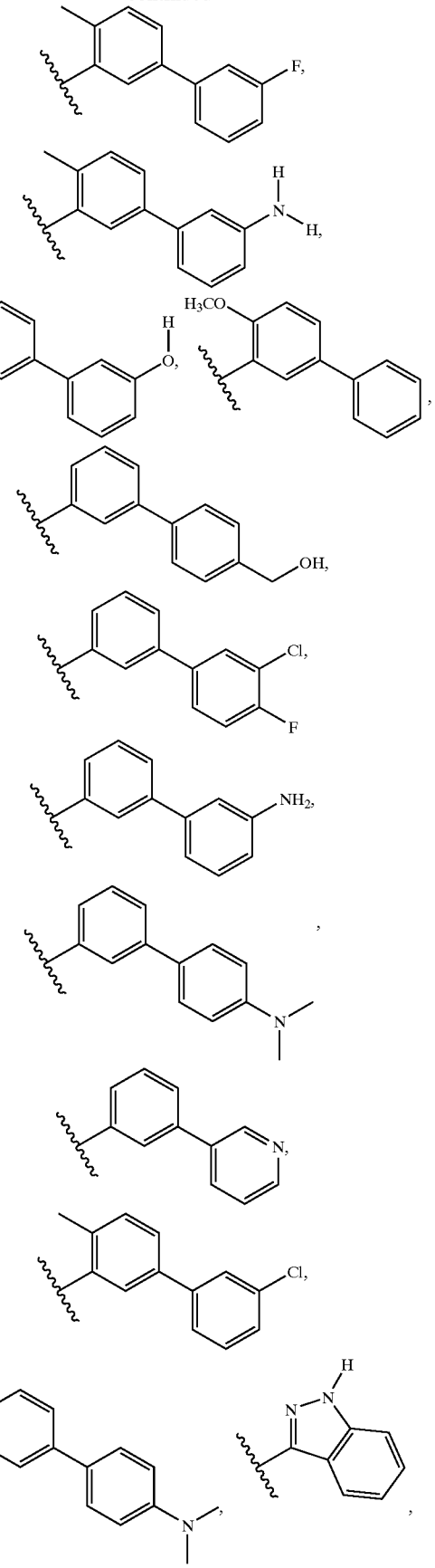

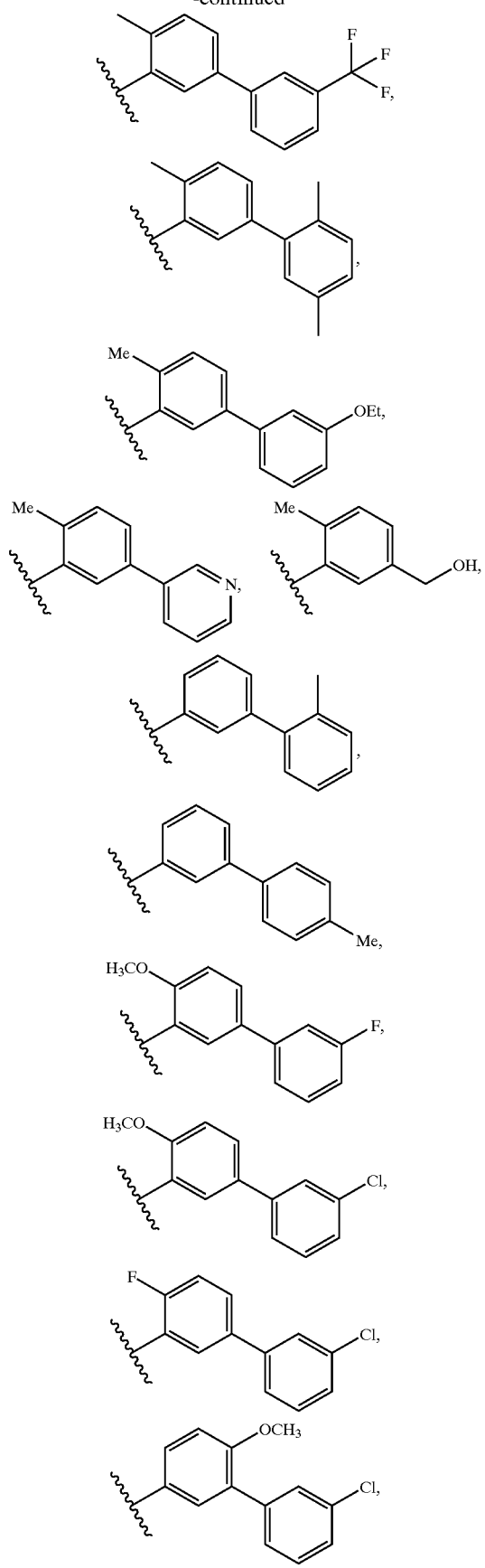
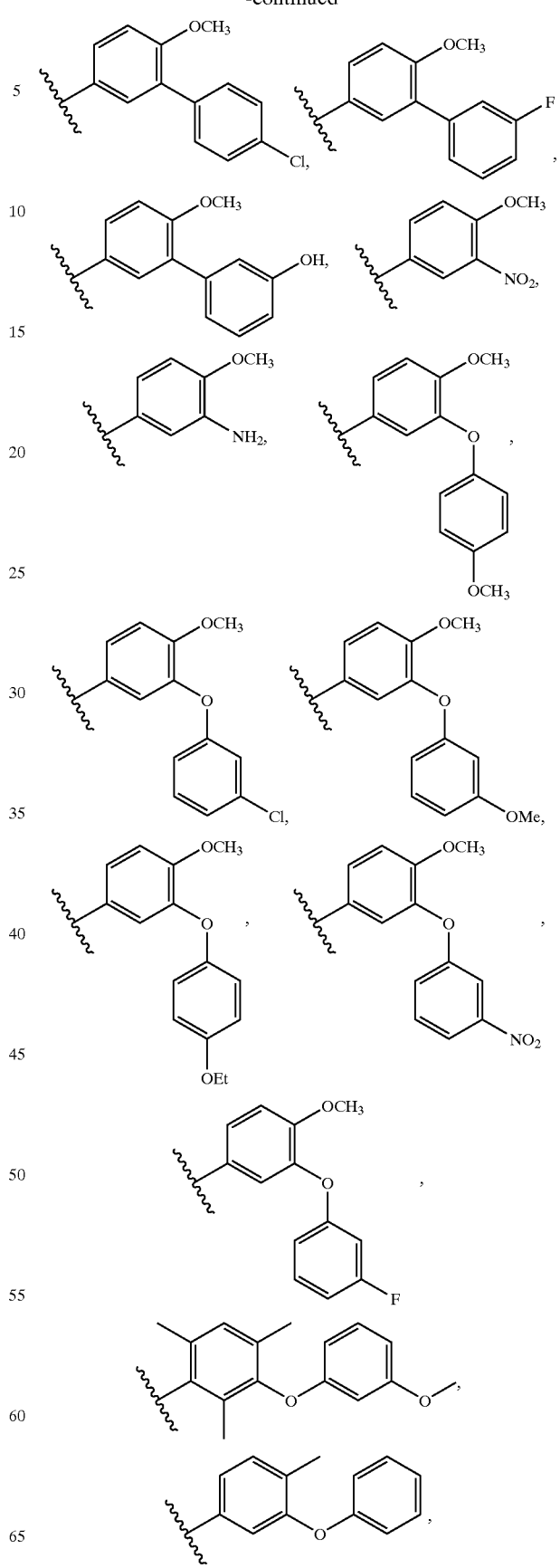

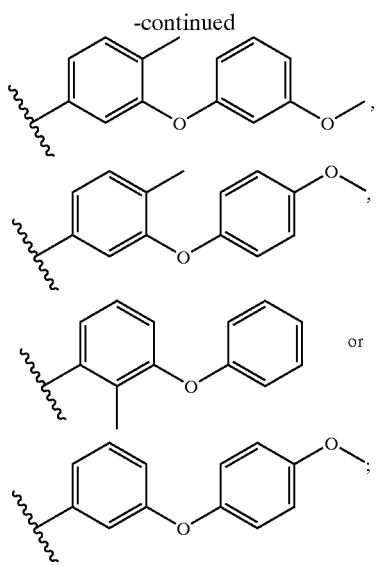

Ar² is a 5–6 membered saturated, partially unsaturated, or fully unsaturated monocyclic ring having 0–3 heteroatoms independently selected from nitrogen, oxygen, or sulfur, or an 8–10 membered saturated, partially unsaturated, or fully unsaturated bicyclic ring system having 0–5 heteroatoms independently selected from nitrogen, oxygen, or sulfur; wherein:

Ar² is optionally substituted with up to five substituents, wherein the first substituent is selected from $R^x$ or $R^5$ and wherein any additional substituents are independently selected from $R^5$;

each $R^x$ is independently selected from a 5–6 membered aryl ring having 0–3 heteroatoms selected from nitrogen, oxygen, or sulfur, wherein:

$R^x$ is optionally substituted with 1–3 $R^5$;

each $R^5$ is independently selected from R, halogen, $NO_2$, CN, SR, $N(R)_2$, NRC(O)R, NRC(O)N(R)$_2$, $NRCO_2R$, C(O)R, $CO_2R$, OC(O)N(R)$_2$, SOR, $SO_2R$, $SO_2N(R)_2$, $NRSO_2R$, $NRSO_2N(R)_2$, C(O)C(O)R, or C(O)CH$_2$C(O)R;

provided that:

(i) when $R^4$ is phenyl substituted with two OR, wherein R is not hydrogen, the two OR occupy positions on the phenyl ring other than simultaneously meta and para; and (ii) said compound is other than a compound of formula III

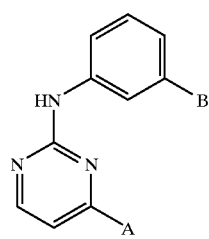

III wherein:

A is a phenyl ring substituted with one or more groups selected from halogen, CN, OC(O)NH$_2$, $CO_2R^{10}$, $COR^{10}$, $SO_2N(R^{10})_2$, $N(R^{10})_2$, $OR^{10}$, or fluoro-alkyl, wherein each $R^{10}$ is independently selected from hydrogen or a $C_1$–$C_7$ alkyl group optionally substituted with $NH_2$, NH($C_1$–$C_7$ alkyl), or N($C_1$–$C_7$ alkyl)$_2$; and B is selected from halogen, CN, OC(O)NH$_2$, $CO_2R^{10}$, $COR^{10}$, $SO_2N(R^{10})_2$, $N(R^{10})_2$, $OR^{10}$, or fluoro-($C_1$–$C_7$ alkyl).

22. The compound according to claim 21, wherein:

$R^1$, $R^2$, and $R^3$ are independently selected from halogen, QR or QAr²;

Q is a $C_{1-3}$ alkylidene chain wherein one methylene unit of Q is optionally replaced by —O—, —S—, —NHCO—, or —NR—; and Ar² is an optionally substituted 5–6 membered saturated, partially unsaturated, or fully unsaturated ring having 0–2 heteroatoms independently selected from nitrogen, oxygen, or sulfur.

23. The compound according to claim 22, wherein:

$R^1$, $R^2$, and $R^3$ are independently selected from OH, $OCH_3$, $OCH_2CH_3$, NHCOMe, $NH_2$, NH($C_{1-4}$ aliphatic), N($C_{1-4}$ aliphatic)$_2$, O(CH$_2$)$_2$morpholin-4-yl, O(CH$_2$)$_2$NH$_2$, O(CH$_2$)$_2$NH($C_{1-4}$ aliphatic), O(CH$_2$)$_2$N ($C_{1-4}$ aliphatic)$_2$, bromo, chloro, or fluoro; or $R^1$ and $R^2$ or $R^2$ and $R^3$ are taken together to form

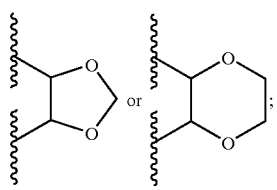

and

Ar² is selected from morpholin-4-yl, pyrrolidin-1-yl, piperidin-1-yl, thiomorpholin-4-yl, pyrazol-1-yl, or imidazol-1-yl.

24. A composition comprising a compound according to claim 21 and a pharmaceutically acceptable carrier, adjuvant, or vehicle.

25. The composition according to claim 24, additionally comprising an additional therapeutic agent selected from anti-proliferative agent, an anti-inflammatory agent, an immunomodulatory agent, a neurotrophic factor, an agent for treating cardiovascular disease, an agent for treating liver disease, an anti-viral agent, an agent for treating blood disorders, an agent for treating diabetes, or an agent for treating immunodeficiency disorders.

* * * * *